(12) United States Patent
Arista et al.

(10) Patent No.: US 11,160,797 B2
(45) Date of Patent: Nov. 2, 2021

(54) PYRIDINONE DERIVATIVES AND THEIR USE AS SELECTIVE ALK-2 INHIBITORS

(71) Applicant: NOVARTIS AG, Basel (CH)

(72) Inventors: Luca Arista, Riehen (CH); Sylvie Chamoin, Saint-Louis (FR); Pier Luca D'Alessandro, Hegenheim (FR); Mika Lindvall, Oakland, CA (US); Dimitrios Lizos, Basel (CH); Nikolaus Johannes Stiefl, Lörrach (DE); Sylvie Teixeira-Fouchard, Basel (CH); Thomas Ullrich, Bottmingen (CH); Sven Weiler, Lörrach (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/766,114

(22) PCT Filed: Nov. 24, 2017

(86) PCT No.: PCT/IB2017/057389
§ 371 (c)(1),
(2) Date: May 21, 2020

(87) PCT Pub. No.: WO2019/102256
PCT Pub. Date: May 31, 2019

(65) Prior Publication Data
US 2020/0360357 A1   Nov. 19, 2020

(51) Int. Cl.
| | |
|---|---|
| *A61K 31/444* | (2006.01) |
| *A61P 19/08* | (2006.01) |
| *A61K 31/497* | (2006.01) |
| *A61K 31/501* | (2006.01) |
| *C07D 401/14* | (2006.01) |
| *C07D 403/14* | (2006.01) |
| *C07D 405/14* | (2006.01) |
| *C07D 417/14* | (2006.01) |
| *C07D 471/04* | (2006.01) |

(52) U.S. Cl.
CPC .......... *A61K 31/444* (2013.01); *A61K 31/497* (2013.01); *A61K 31/501* (2013.01); *A61P 19/08* (2018.01); *C07D 401/14* (2013.01); *C07D 403/14* (2013.01); *C07D 405/14* (2013.01); *C07D 417/14* (2013.01); *C07D 471/04* (2013.01)

(58) Field of Classification Search
CPC combination set(s) only.
See application file for complete search history.

(56) References Cited

U.S. PATENT DOCUMENTS 8,697,715 B2   4/2014   Blake et al.

FOREIGN PATENT DOCUMENTS

| WO | 2016/054406 A1 | 4/2016 |
| WO | 2016/165808 A1 | 10/2016 |

OTHER PUBLICATIONS

International Search Report and Written Opinion for International Patent Application No. PCT/IB2017/057389, dated Dec. 2, 2018.

*Primary Examiner* — Heidi Reese
(74) *Attorney, Agent, or Firm* — Jana A. Dailey

(57) ABSTRACT

The invention relates to a compound of Formula I or a pharmaceutically acceptable salt thereof, a method for manufacturing the compounds of the invention, and its therapeutic uses. The present invention further provides a combination of pharmacologically active agents and a pharmaceutical composition.

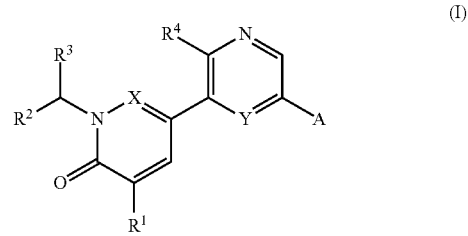

(I)

18 Claims, 8 Drawing Sheets

PYRIDINONE DERIVATIVES AND THEIR USE AS SELECTIVE ALK-2 INHIBITORS

RELATED APPLICATIONS

This application is a U.S. National Phase filing of International Application Serial No. PCT/IB2017/057389 filed 24 Nov. 2017, which is incorporated in its entirety herein.

BACKGROUND OF THE INVENTION

ALK-2, also known as activin A receptor, type I (ACVR1) or as serine threonine protein kinase receptor $R^1$ (SKR1) is a protein kinase which in humans is encoded by the ACVR1 gene.

ALK-2 is a type I BMP receptor which is widely expressed. It comprises an extracellular ligand binding domain and a regulated intracellular serine/threonine kinase domain, both required for signal transduction.

Bone morphogenic proteins (BMPs) are multi-functional growth factors that are members of the transforming growth factor β (TGFβ) superfamily. BMP signaling plays a role in heart, neural, and cartilage development as well as in postnatal bone formation. BMPs ectopically induce endochondral bone formation and play a critical role in skeletal and joint morphogenesis (Urist, Science 110:893-899 (1965); Olsen et al, Annu. Rev. Cell Dev. Biol. 16:191-220 (2000); Kronenberg, Nature 423:332-336 (2003); Thomas et al, Nat. Genet. 12:315-317 (1996); Thomas et al, Nat. Genet. 17:58-64 (1997); Polinkowsky et al, Nat. Genet. 17:18-19 (1997); Storm et al., Nature 368:639-643 (1994); and Wozney, Prog. Growth Factor Res. 1:267-280 (1989)).

BMP signaling is controlled at many levels, including via extracellular antagonists such as noggin (Massague, Nat. Rev. Mol. Cell. Biol. 1:169-178 (2000)). It has been suggested that untimely or unwanted activation of signaling pathways fundamental for normal development may promote disease processes such as spondyloarthropathies. The effects of BMP signaling on initiation and progression of arthritis by gene transfer of noggin have also been described (Lories et al, J. Clin. Invest., 115, 1571-1579 (2005)). The physiological roles of BMPs and BMP receptor signaling in normal bone formation, including skeletal and limb development, have been studied and reviewed in Zhao, Genetics 35:43-56 (2003).

Experiments with BMP antagonists demonstrate that regulation of BMP signaling proteins is central to bone formation in vivo (Devlin et al., Endocrinology 144:1972-1978 (2003) and Wu et al., J. Clin. Invest., 112: 924 (2003)).

Fibrodysplasia ossificans progressiva (FOP) is a rare and disabling genetic disorder characterized by congenital malformations of the great toes and by progressive heterotopic endochodral ossification in predictable anatomical patterns. Ectopic expression of BMP4 has been found in FOP patients (Gannon et al., Hum. Pathol. 28:339-343 (1997) and Xu et al, Clin. Genet. 58:291-298 (2000)). It has been shown that patients with FOP have activating mutations in ALK-2 (Shore et al., Nat. Genet., 38(5):525-7 (2006)).

It has been established that excessive BMP signaling leads to a number of conditions described above. WO2008033408 and WO2009114180 describe inhibitors of the BMP signaling pathway. There is still however a constant need to find alternative ways in which BMP signaling can be regulated.

Such a need can be met by designing selective ALK-2 inhibitors.

Specific ALK-2 antibodies are described for instance in WO1994011502 and WO2008030611. Osteogenic proteins that bind to ALK-2 are described in WO2012023113 and WO2012077031.

WO2007123896 describes a method of treating a pathology associated with heterotopic ossification by administering siRNA specific against a nucleic acid encoding a mutated ALK-2.

SUMMARY OF THE INVENTION

There is a continuing need to develop new ALK-2 inhibitors that are good drug candidates. Such candidates would find applications inter alia in the treatment of fibrodysplasia ossificans progressiva (FOP), non-hereditary heterotopic ossification (HO), anemia of chronic disease (ACD), osteoporosis or pulmonary arterial hypertension.

The invention provides compounds, pharmaceutically acceptable salts thereof, pharmaceutical compositions thereof and combinations thereof, which compounds are ALK-2 inhibitors. The invention further provides methods of treating, preventing, or ameliorating fibrodysplasia ossificans progressiva (FOP), non-hereditary heterotopic ossification (HO) and anemia of chronic disease (ACD), osteoporosis or pulmonary arterial hypertension comprising administering to a subject in need thereof an effective amount of an ALK-2 inhibitor.

Various embodiments of the invention are described herein.

Within certain aspects, provided herein is a compound of Formula (I) or a pharmaceutically acceptable salt thereof:

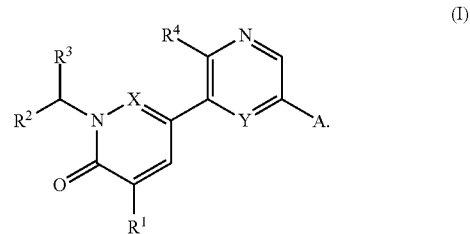

In another embodiment, the invention provides a pharmaceutical composition comprising a therapeutically effective amount of a compound according to the definition of formula (I), or a pharmaceutically acceptable salt thereof, or subformulae thereof (Ia), (Ia-1), (Ib), (Ib-1), (Ic), (Ic-1), (Id), (Id-1), (Ie), (Ie-1) and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof (Ia), (Ia-1), (Ib), (Ib-1), (Ic), (Ic-1), (Id), (Id-1), (Ie), (Ie-1) and one or more therapeutically active agent.

In a further aspect, the invention relates to a method of inhibiting ALK-2 receptor activity in a subject, wherein the method comprises administering to the subject a therapeutically effective amount of the compound of formula (I) as defined herein or a pharmaceutically acceptable salt thereof.

In yet another aspect, the invention relates to a method of treating a disorder or disease selected from anaemia of chronic disease, heterotopic ossification, fibrodysplasia ossificans progressiva, comprising administering to the subject a therapeutically effective amount of the compound of formula (I) as defined herein or a pharmaceutically acceptable salt thereof.

DETAILED DESCRIPTION OF THE INVENTION

Figure 1:
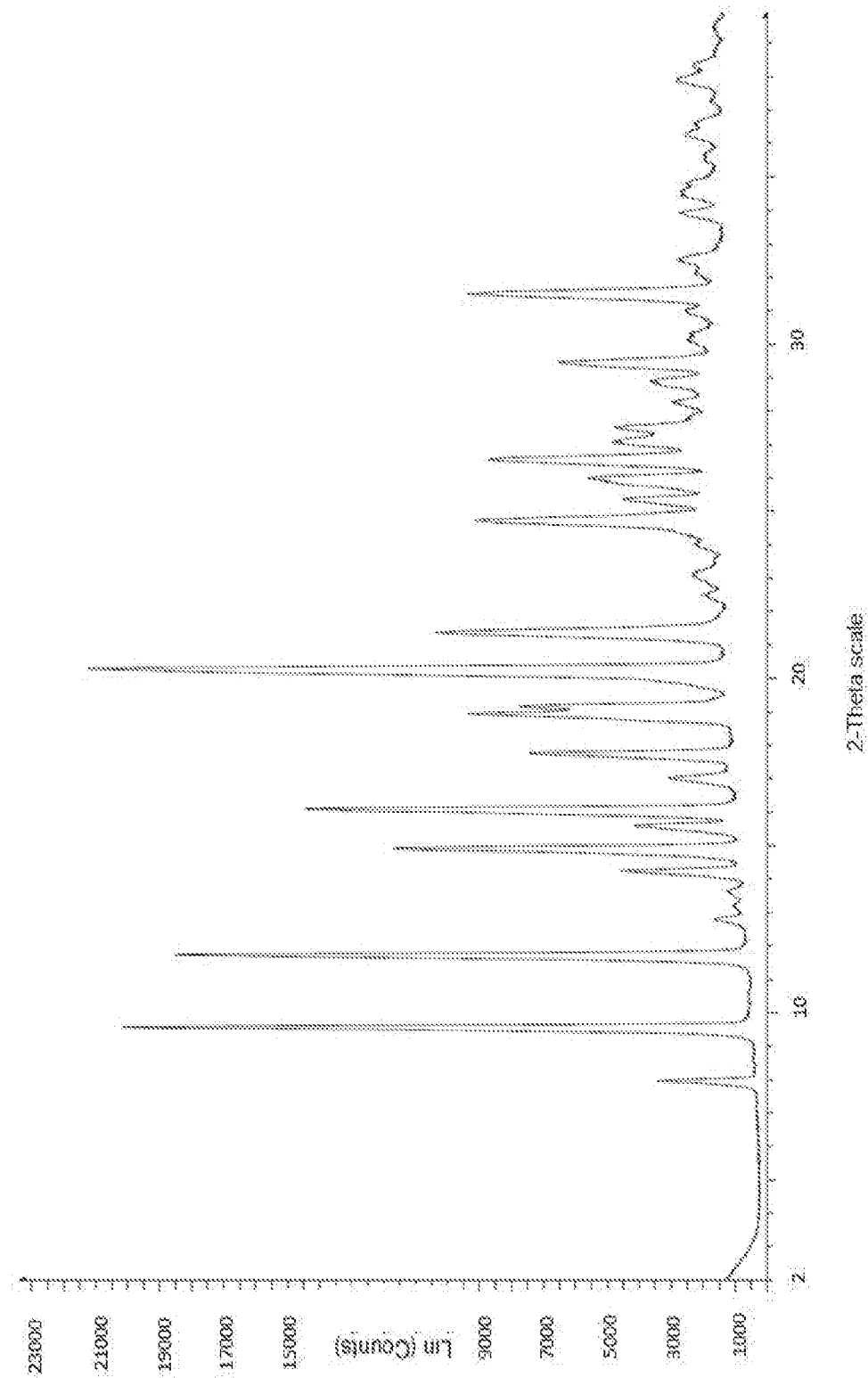
FIG. 1 shows the X-ray powder diffraction pattern of crystalline 5-(1'-isopropyl-6'-oxo-1',6'-dihydro-[3,3'-bipyridin]-5-yl)-1-methylindolin-2-one monohydrate.

In particular, the invention relates to a compound of formula (I), or a pharmaceutically acceptable salt thereof,

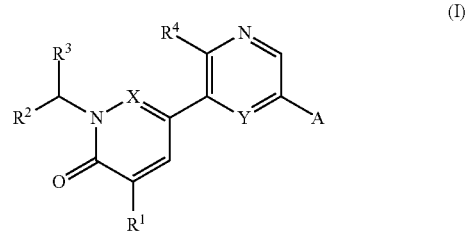

(I)

wherein
A represents

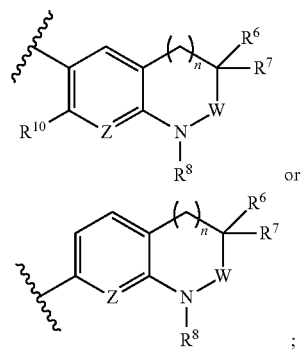

;

$R^1$ represents hydrogen, $C_{1-4}$alkyl or $C_{1-4}$alkoxy;
$R^2$ and $R^3$ independently represent hydrogen, $C_{1-6}$alkyl, $C_{1-6}$haloalkyl, $C_{1-6}$alkoxy, $C_{3-6}$cycloalkyl or $R^2$ and $R^3$ together with the carbon atom to which they are attached form a 3- to 6-membered ring which may contain one heteroatom;
X is N or —CH;
$R^4$ represents hydrogen or amino;
Y is N or —$CR^5$;
$R^5$ is hydrogen or fluorine;
Z is N or —$CR^9$;
n is 0, 1 or 2;
W is —C(=O)— or —S(O)$_2$—;
$R^6$ and $R^7$ independently represent hydrogen, fluorine or $C_{1-4}$alkyl;
$R^8$ represents hydrogen, $C_{1-8}$alkyl, $C_{3-6}$cycloalkyl$C_{1-6}$alkyl, $C_{1-4}$alkoxy$C_{1-6}$alkyl, hydroxy$C_{1-6}$alkyl;
$R^9$ represents hydrogen, halogen or $C_{1-4}$alkyl; and
$R^{10}$ represents hydrogen or halogen.

Unless specified otherwise, the term "compounds of the present invention" or "compounds of the invention" refers to compounds of formula (I), (Ia), (Ia-1), (Ib), (Ib-1), (Ic), (Ic-1), (Id), (Id-1), (Ie), (Ie-1) and pharmaceutically acceptable salts thereof, as well as all stereoisomers (including diastereoisomers and enantiomers), rotamers, tautomers and isotopically labeled compounds (including deuterium substitutions), as well as inherently formed moieties.

As used herein, the term "$C_{1-8}$alkyl" refers to a straight or branched hydrocarbon chain radical consisting solely of carbon and hydrogen atoms, containing no unsaturation, having from one to eight carbon atoms, and which is attached to the rest of the molecule by a single bond. The term "$C_{1-6}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

As used herein, the term "alkylene" refers to a divalent alkyl group, wherein the alkyl group may be "$C_{1-6}$alkyl" as defined above. Examples of alkylene include, but are not limited to, ethylene and propylene.

As used herein, the term "hydroxy$C_{1-6}$alkyl" refers to a radical of formula —$R_a$—OH, wherein $R_a$ is $C_{1-6}$ alkyl as defined above.

As used herein, the term "$C_{3-6}$cycloalkyl" refers to saturated monocyclic hydrocarbon groups of 3-6 carbon atoms. Examples of $C_{3-6}$cycloalkyl include cyclopropyl, cyclobutyl, cyclopentyl and cyclohexyl.

As used herein, the term "$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy.

As used herein, the term "$C_{1-4}$alkoxy$C_{1-6}$alkyl" refers to a radical of the formula —$R_b$—O—$R_a$ where $R_a$ is a $C_{1-4}$alkyl radical and $R_b$ is a $C_{1-6}$alkyl radical as defined above. The oxygen atom may be bonded to any carbon atom in either alkyl radical. Examples of $C_{1-4}$alkoxy$C_{1-6}$alkyl include, but are not limited to, methoxy-methyl, methoxy-ethyl, ethoxy-ethyl, 1-ethoxy-propyl and 2-methoxy-butyl.

As used herein, the term "$C_{3-6}$cycloalkyl$C_{1-6}$alkyl" refers to a stable non-aromatic monocyclic hydrocarbon radical consisting solely of carbon and hydrogen atoms, having from three to six carbon atoms, and which is saturated and attached to the rest of the molecule by a $C_{1-6}$alkyl radical as defined above. Examples of $C_{3-6}$cycloalkyl$C_{1-6}$alkyl include, but are not limited to, cyclopropyl-methyl, cyclobutyl-ethyl, cyclopentyl-propyl.

"Halogen" or "halo" refers to bromo, chloro, fluoro or iodo.

As used herein, a "3- to 6-membered ring which may contain one heteroatom" refers to a 3-, 4-, 5-, or 6-membered carbocycle or a 3-, 4-, 5- or 6-membered heterocycle comprising one heteroatom selected from N, O or S. Examples of 3-, 4-, 5-, or 6-membered carbocycle include, but are not limited to, cyclopropyl, cyclobutyl, cyclopentyl, cyclohexyl. 3-, 4-, 5- or 6-membered heterocycle include, but are not limited to, tetrahydropyran.

As used herein, the term "halogen$C_{1-6}$alkyl" or "halo$C_{1-6}$alkyl" refers to $C_{1-6}$alkyl radical, as defined above, substituted by one or more halo radicals, as defined above. Examples of halogen$C_{1-6}$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "ALK-2" refers to activin A receptor, type I (ACVRI), also known as ACVRLK2; SKR1; ACVR1A; Activin receptor type I; Activin receptor-like kinase 2; Serine/threonine-protein kinase receptor R1; TGF-B superfamily receptor type I; ACTRI; TSRI; activin A receptor, type II-like kinase 2; activin receptor type-1; hydroxyalkyl-protein kinase; ACTR-I; TSR-I.

Various embodiments of the invention are described herein. It will be recognized that features specified in each embodiment may be combined with other specified features to provide further embodiments of the present invention.

Embodiment 1. A compound of the formula (I), or a pharmaceutically acceptable salt thereof, as described above. A particular variant of this embodiment is a compound of the formula (I), or a pharmaceutically acceptable salt thereof, wherein
A represents

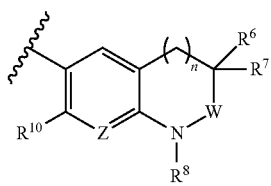

$R^1$ represents hydrogen;
$R^2$ and $R^3$ represent $C_{1-6}$alkyl;
X is —CH;
$R^4$ represents hydrogen;
Y is —$CR^5$;
$R^5$ is hydrogen;
Z is —$CR^9$;
n is 0;
W is —C(=O)—;
$R^6$ and $R^7$ represent hydrogen;
$R^8$ represents $C_{1-6}$alkyl, $C_{3-6}$cycloalkyl$C_{1-6}$alkyl or $C_{1-4}$alkoxy$C_{1-6}$alkyl;
$R^9$ represents hydrogen; and
$R^{10}$ represents hydrogen.

Embodiment 2. A compound of the formula (I), or a pharmaceutically acceptable salt thereof, wherein the A group is a 5-yl-indolin-2-one group.

Embodiment 3. A compound of the formula (I), or a pharmaceutically acceptable salt thereof, wherein the A group is a 6-yl-indolin-2-one group.

Embodiment 4. A compound of the formula (I), or a pharmaceutically acceptable salt thereof, wherein the A group is a 5-yl-pyrrolo[2,3-b]pyridine-2(3H)-one group.

Embodiment 5. A compound of the formula (I), or a pharmaceutically acceptable salt thereof, wherein the A group is a 6-yl-3,4-dihydroquinoline-2(1H)-one group.

Embodiment 6. A compound of the formula (I), or a pharmaceutically acceptable salt thereof, wherein the A group is a 6-yl-3,4-dihydro-1,8-naphthyridin-2(1H)-one group.

Embodiment 7. A compound of the formula (I), or a pharmaceutically acceptable salt thereof, wherein the A group is a 7-yl-4,5-dihydro-1H-benzo[b]azepin-2(3H)-one group.

Embodiment 8. A compound according to any of embodiments 1 to 7 or a pharmaceutically acceptable salt thereof, wherein $R^1$ is hydrogen.

Embodiment 9. A compound according to any of embodiments 1 to 8 or a pharmaceutically acceptable salt thereof wherein $R^2$ and $R^3$ independently represent hydrogen or $C_{1-6}$alkyl, especially each is hydrogen.

Embodiment 10. A compound according to any of embodiments 1 to 9 or a pharmaceutically acceptable salt thereof wherein $R^2$ and $R^3$ are both methyl.

Embodiment 11. A compound according to any of embodiments 1 to 8 or a pharmaceutically acceptable salt thereof wherein $R^2$ and $R^3$ together with the carbon atom to which they are attached form a cyclopropyl, cyclobutyl, cyclopentyl, cyclohexyl or tetrahydropyranyl ring.

Embodiment 12. A compound according to any of embodiments 1 to 11 or a pharmaceutically acceptable salt thereof wherein $R^4$ is hydrogen.

Embodiment 13. A compound according to any of embodiments 1 to 12 or a pharmaceutically acceptable salt thereof wherein X is —CH.

Embodiment 14. A compound according to any of embodiments 1 to 12 or a pharmaceutically acceptable salt thereof wherein X is N.

Embodiment 15. A compound according to any of embodiments 1 to 14 or a pharmaceutically acceptable salt thereof wherein Y is —CH.

Embodiment 16. A compound according to any of embodiments 1 to 14 or a pharmaceutically acceptable salt thereof wherein Y is —CF.

Embodiment 17. A compound according to any of embodiments 1 to 14 or a pharmaceutically acceptable salt thereof wherein Y is N.

Embodiment 18. A compound according to any of embodiments 1 to 17 or a pharmaceutically acceptable salt thereof wherein Z is —CH.

Embodiment 19. A compound according to any of embodiments 1 to 17 or a pharmaceutically acceptable salt thereof wherein Z is N.

Embodiment 20. A compound according to any of embodiments 1 to 19 or a pharmaceutically acceptable salt thereof wherein n is 0.

Embodiment 21. A compound according to any of embodiments 1 to 19 or a pharmaceutically acceptable salt thereof wherein n is 1.

Embodiment 22. A compound according to any of embodiments 1 to 19 or a pharmaceutically acceptable salt thereof wherein n is 2.

Embodiment 23. A compound according to any of embodiments 1 to 22 or a pharmaceutically acceptable salt thereof wherein W is —C(=O)—.

Embodiment 24. A compound according to any of embodiments 1 to 22 or a pharmaceutically acceptable salt thereof wherein W is —S(O)$_2$—.

Embodiment 25. A compound according to any of embodiment 1 to 24 or a pharmaceutically acceptable salt thereof wherein $R^6$ and $R^7$ independently represent hydrogen or fluorine.

Embodiment 26. A compound according to any of embodiments 1 to 25 or a pharmaceutically acceptable salt thereof wherein $R^8$ is hydrogen or $C_{1-6}$alkyl.

Embodiment 27. A compound according to any of embodiments 1 to 26 or a pharmaceutically acceptable salt thereof wherein $R^8$ is methyl or in particular 2-methylpropyl, cyclobutylmethyl or 3-methoxypropyl.

Embodiment 28. A compound according to any of embodiments 1 to 27 or a pharmaceutically acceptable salt thereof wherein $R^9$ is hydrogen.

Embodiment 29. A compound according to any of embodiments 1 to 28 or a pharmaceutically acceptable salt thereof wherein $R^{10}$ is hydrogen.

Embodiment 30. A compound of formula (Ia), or a pharmaceutically acceptable salt thereof,

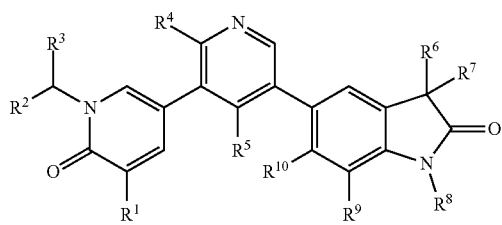

(Ia)

wherein $R^1$, $R^2$, $R^3$, $R^4$, $R^6$, $R^7$, $R^8$, $R^9$, $R^{10}$ are as defined in any of the preceding embodiments 8 to 12 and 25 to 29 and $R^5$ is hydrogen or fluorine.

Embodiment 31. A compound of formula (Ia-1), or a pharmaceutically acceptable salt thereof,

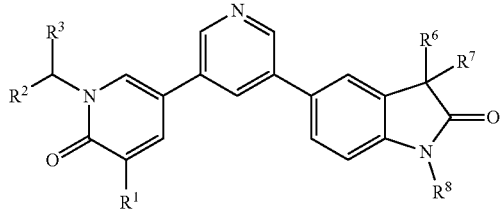

(Ia-1)

wherein $R^1$, $R^2$, $R^3$, $R^6$, $R^7$ and $R^8$ are as defined in any of the preceding embodiments 8 to 11 and 25 to 27; in particular $R^1$ is hydrogen; $R^2$ is methyl; $R^3$ is methyl; $R^6$ is hydrogen; $R^7$ is hydrogen; and $R^8$ is $C_{1-6}$alkyl, $C_{3-6}$cycloalkyl$C_{1-6}$alkyl, $C_{1-4}$alkoxy$C_{1-6}$alkyl, more particularly 2-methylpropyl (=isobutyl), 3-methoxypropyl or cyclobutylmethyl.

Embodiment 32. A compound of formula (Ia-1) according to embodiment 31 or a pharmaceutically acceptable salt thereof, wherein $R^1$ is hydrogen.

Embodiment 33. A compound of formula (Ia-1) according to embodiment 31 or 32 or a pharmaceutically acceptable salt thereof, wherein $R^2$ and $R^3$ independently represent hydrogen or $C_{1-6}$alkyl.

Embodiment 34. A compound of formula (Ia-1) according to any of embodiments 31 to 33 or a pharmaceutically acceptable salt thereof, wherein $R^6$ and $R^7$ both represent hydrogen.

Embodiment 35. A compound of formula (Ia-1) according to any of embodiments 31 to 34 or a pharmaceutically acceptable salt thereof, wherein $R^8$ represents hydrogen or $C_1$-$C_6$alkyl.

Embodiment 36. A compound of formula (Ib), or a pharmaceutically acceptable salt thereof,

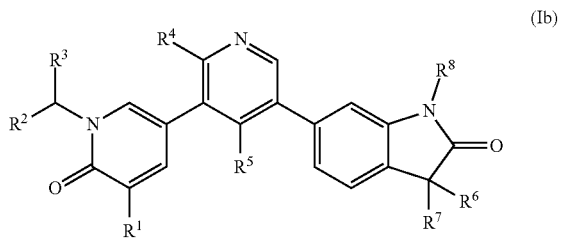

(Ib)

wherein $R^1$, $R^2$, $R^3$, $R^4$, $R^6$, $R^7$, $R^8$ are as defined in any of the preceding embodiments 8 to 12 and 25 to 29 and $R^5$ is hydrogen or fluorine.

Embodiment 37. A compound of formula (Ib-1), or a pharmaceutically acceptable salt thereof,

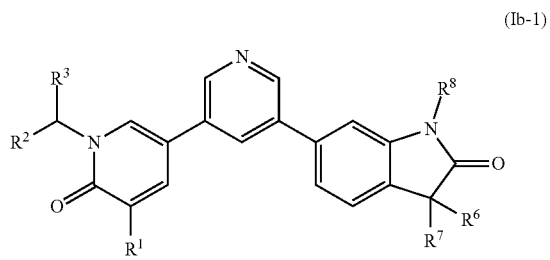

(Ib-1)

wherein $R^1$, $R^2$, $R^3$, $R^6$, $R^7$ and $R^8$ are as defined in any of the preceding embodiments 8 to 11 and 25 to 27.

Embodiment 38. A compound of formula (Ic) or a pharmaceutically acceptable salt thereof,

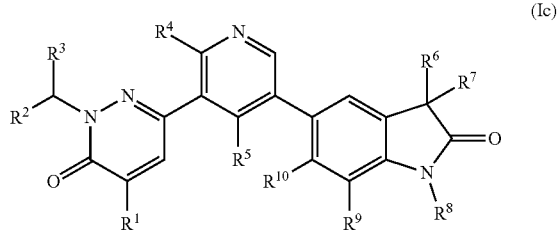

(Ic)

wherein $R^1$, $R^2$, $R^3$, $R^4$, $R^6$, $R^7$, $R^8$, $R^9$, $R^{10}$ are as defined in any of the preceding embodiments 8 to 12 and 25 to 29 and $R^5$ is hydrogen or fluorine.

Embodiment 39. A compound of formula (Ic-1), or a pharmaceutically acceptable salt thereof,

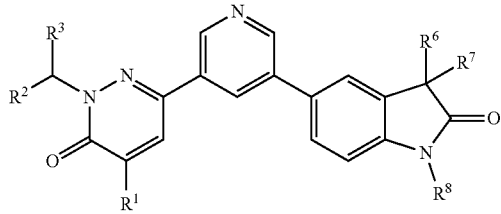
(Ic-1)

wherein $R^1$, $R^2$, $R^3$, $R^6$, $R^7$ and $R^8$ are as defined in any of the preceding embodiments 8 to 11 and 25 to 27.

Embodiment 40. A compound of formula (Id) or a pharmaceutically acceptable salt thereof,

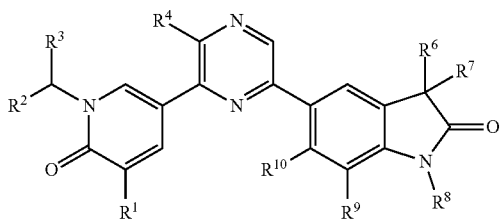
(Id)

wherein $R^1$, $R^2$, $R^3$, $R^4$, $R^6$, $R^7$, $R^8$, $R^9$, $R^{10}$ are as defined in any of the preceding embodiments 8 to 12 and 25 to 29.

Embodiment 41. A compound of formula (Id-1), or a pharmaceutically acceptable salt thereof,

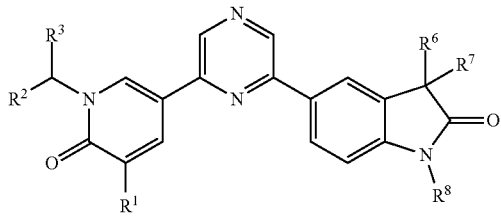
(Id-1)

wherein $R^1$, $R^2$, $R^3$, $R^6$, $R^7$ and $R^8$ are as defined in any of the preceding embodiments 8 to 11 and 25 to 27.

Embodiment 42. A compound of formula (Ie)

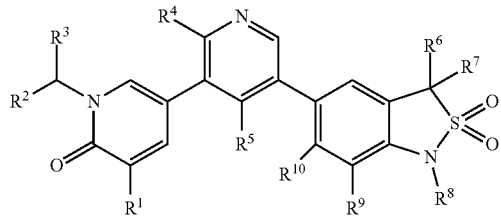
(Ie)

wherein $R^1$, $R^2$, $R^3$, $R^4$, $R^6$, $R^7$, $R^8$, $R^9$, $R^{10}$ are as defined in any of the preceding embodiments 8 to 12 and 25 to 29 and
$R^5$ is hydrogen or fluorine.

Embodiment 43. A compound of formula (Ie-1)

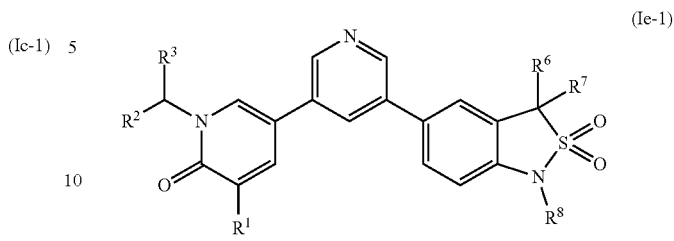
(Ie-1)

wherein $R^1$, $R^2$, $R^3$, $R^6$, $R^7$ and $R^8$ are as defined in any of the preceding embodiments 8 to 11 and 25 to 27.

Embodiment 44. A compound or a pharmaceutically acceptable salt thereof, which is selected from 5-(1'-isopropyl-6'-oxo-1',6'-dihydro-[3,3'-bipyridin]-5-yl)-1-methylindolin-2-one (compound A);

5-(1'-Isopropyl-5'-methoxy-6'-oxo-1',6'-dihydro-[3,3'-bipyridin]-5-yl)-1-methylindolin-2-one;

5-(5-(1-Isopropyl-5-methyl-6-oxo-1,6-dihydropyridin-3-yl)pyridin-3-yl)-1-methylindolin-2-one;

1-methyl-5-(6'-oxo-1'-(pentan-3-yl)-1',6'-dihydro-[3,3'-bipyridin]-5-yl)indolin-2-one;

5-(5'-Ethyl-1'-isopropyl-6'-oxo-1',6'-dihydro-[3,3'-bipyridin]-5-yl)-1-methylindolin-2-one;

5-(1'-Cyclobutyl-6'-oxo-1',6'-dihydro-[3,3'-bipyridin]-5-yl)-1-methylindolin-2-one;

5-(1'-(sec-butyl)-6'-oxo-1',6'-dihydro-[3,3'-bipyridin]-5-yl)-1-methylindolin-2-one;

5-(1'-cyclopentyl-6'-oxo-1',6'-dihydro-[3,3'-bipyridin]-5-yl)-1-methylindolin-2-one;

5-(1'-ethyl-6'-oxo-1',6'-dihydro-[3,3'-bipyridin]-5-yl)-1-methylindolin-2-one;

5-(1'-cyclopropyl-6'-oxo-1',6'-dihydro-[3,3'-bipyridin]-5-yl)-1-methylindolin-2-one;

5-(1'-(cyclobutylmethyl)-6'-oxo-1',6'-dihydro-[3,3'-bipyridin]-5-yl)-1-methylindolin-2-one;

1-methyl-5-(6'-oxo-1'-(2,2,2-trifluoroethyl)-1',6'-dihydro-[3,3'-bipyridin]-5-yl)indolin-2-one;

5-(1'-(2-ethylbutyl)-6'-oxo-1',6'-dihydro-[3,3'-bipyridin]-5-yl)-1-methylindolin-2-one;

5-(1'-isobutyl-6'-oxo-1',6'-dihydro-[3,3'-bipyridin]-5-yl)-1-methylindolin-2-one;

5-(1'-(methoxymethyl)-6'-oxo-1',6'-dihydro-[3,3'-bipyridin]-5-yl)-1-methylindolin-2-one;

1-methyl-5-(6'-oxo-1'-(3,3,3-trifluoropropyl)-1',6'-dihydro-[3,3'-bipyridin]-5-yl)indolin-2-one;

5-(1'-isopentyl-6'-oxo-1',6'-dihydro-[3,3'-bipyridin]-5-yl)-1-methylindolin-2-one;

1-methyl-5-(6'-oxo-1'-(tetrahydro-2H-pyran-2-yl)-1',6'-dihydro-[3,3'-bipyridin]-5-yl)indolin-2-one;

1-methyl-5-(1'-methyl-6'-oxo-1',6'-dihydro-[3,3'-bipyridin]-5-yl)indolin-2-one;

1-ethyl-5-(1'-isopropyl-6'-oxo-1',6'-dihydro-[3,3'-bipyridin]-5-yl)indolin-2-one;

1-Isopropyl-5-(1'-isopropyl-6'-oxo-1',6'-dihydro-[3,3'-bipyridin]-5-yl)indolin-2-one;

3-Ethyl-5-(1'-isopropyl-6'-oxo-1',6'-dihydro-[3,3'-bipyridin]-5-yl)-1-methylindolin-2-one;

3,3-Difluoro-5-(1'-isopropyl-6'-oxo-1',6'-dihydro-[3,3'-bipyridin]-5-yl)-1-methylindolin-2-one;

1-Isobutyl-5-(1'-isopropyl-6'-oxo-1',6'-dihydro-[3,3'-bipyridin]-5-yl)indolin-2-one (compound B);

5-(1'-Isopropyl-6'-oxo-1',6'-dihydro-[3,3'-bipyridin]-5-yl)-1-propylindolin-2-one;

6-(1'-Isopropyl-6'-oxo-1',6'-dihydro-[3,3'-bipyridin]-5-yl)-1-methylindolin-2-one;

5-(1'-Isopropyl-6'-oxo-1',6'-dihydro-[3,3'-bipyridin]-5-yl)-1-(2-methoxyethyl)-1H-pyrrolo[2,3-b]pyridin-2(3H)-one;

6-(1'-Isopropyl-6'-oxo-1',6'-dihydro-[3,3'-bipyridin]-5-yl)-1-methyl-3,4-dihydroquinolin-2(1H)-one;

5-(1'-Isopropyl-6'-oxo-1',6'-dihydro-[3,3'-bipyridin]-5-yl)-1-(2-methoxyethyl)indolin-2-one;

5-(1'-Isopropyl-6'-oxo-1',6'-dihydro-[3,3'-bipyridin]-5-yl)-1-(3-methoxypropyl)indolin-2-one (compound C);

5-(1'-Isopropyl-6'-oxo-1',6'-dihydro-[3,3'-bipyridin]-5-yl)-1,3,3-trimethyl-1H-pyrrolo[2,3-b]pyridin-2(3H)-one;

6-(1'-isopropyl-6'-oxo-1',6'-dihydro-[3,3'-bipyridin]-5-yl)-3,3-dimethylindolin-2-one;

6-(1'-isopropyl-6'-oxo-1',6'-dihydro-[3,3'-bipyridin]-5-yl)-3-methylindolin-2-one;

5-(5-(1-Isopropyl-6-oxo-1,6-dihydropyridin-3-yl)pyridin-3-yl)indolin-2-one;

5-(1'-isopropyl-6'-oxo-1',6'-dihydro-[3,3'-bipyridin]-5-yl)-1,7-dimethylindolin-2-one;

7-Fluoro-5-(1'-isopropyl-6'-oxo-1',6'-dihydro-[3,3'-bipyridin]-5-yl)-1-methylindolin-2-one;

6-(1'-Isopropyl-6'-oxo-1',6'-dihydro-[3,3'-bipyridin]-5-yl)-1-methyl-3,4-dihydro-1,8-naphthyridin-2(1H)-one;

1-(cyclobutylmethyl)-5-(1'-isopropyl-6'-oxo-1',6'-dihydro-[3,3'-bipyridin]-5-yl)indolin-2-one (compound D);

7-(1'-isopropyl-6'-oxo-1',6'-dihydro-[3,3'-bipyridin]-5-yl)-1-methyl-4,5-dihydro-1H-benzo[b]azepin-2(3H)-one;

1-(2-ethylbutyl)-5-(1'-isopropyl-6'-oxo-1',6'-dihydro-[3,3'-bipyridin]-5-yl)indolin-2-one;

5-(1'-Isopropyl-6'-oxo-1',6'-dihydro-[3,3'-bipyridin]-5-yl)-1H-pyrrolo[2,3-b]pyridin-2(3H)-one;

5-(2-amino-1'-isopropyl-6'-oxo-1',6'-dihydro-[3,3'-bipyridin]-5-yl)-1-methylindolin-2-one;

5-(5-amino-6-(1-isopropyl-6-oxo-1,6-dihydropyridin-3-yl)pyrazin-2-yl)-1-methylindolin-2-one;

5-(5-(1-isopropyl-6-oxo-1,6-dihydropyridazin-3-yl)pyridin-3-yl)-1-methylindolin-2-one;

1-(2-hydroxyethyl)-5-(1'-isopropyl-6'-oxo-1',6'-dihydro-[3,3'-bipyridin]-5-yl)indolin-2-one;

5-(6-(1-isopropyl-6-oxo-1,6-dihydropyridin-3-yl)pyrazin-2-yl)-1-methylindolin-2-one;

1-(3-hydroxypropyl)-5-(1'-isopropyl-6'-oxo-1',6'-dihydro-[3,3'-bipyridin]-5-yl)indolin-2-one and 1-isopropyl-5'-(1-methyl-2,2-dioxido-1,3-dihydrobenzo[c]isothiazol-5-yl)-[3,3'-bipyridin]-6(1H)-one;

5'-(1-ethyl-2,2-dioxido-1,3-dihydrobenzo[c]isothiazol-5-yl)-1-isopropyl-[3,3'-bipyridin]-6(1H)-one;

5'-(1-isobutyl-2,2-dioxido-1,3-dihydrobenzo[c]isothiazol-5-yl)-1-isopropyl-[3,3'-bipyridin]-6(1H)-one;

5'-(1-(cyclobutylmethyl)-2,2-dioxido-1,3-dihydrobenzo[c]isothiazol-5-yl)-1-isopropyl-[3,3'-bipyridin]-6(1H)-one; and 5-(4-fluoro-1'-isopropyl-6'-oxo-1',6'-dihydro-[3,3'-bipyridin]-5-yl)-1-methylindolin-2-one.

Embodiment 45. A compound of formula (I), or a pharmaceutically acceptable salt thereof, wherein the compound is (R)-5-(1'-(sec-butyl)-6'-oxo-1',6'-dihydro-[3,3'-bipyridin]-5-yl)-1-methylindolin-2-one.

Embodiment 46. A compound of formula (I), or a pharmaceutically acceptable salt thereof, wherein the compound is (S)-5-(1'-(sec-butyl)-6'-oxo-1',6'-dihydro-[3,3'-bipyridin]-5-yl)-1-methylindolin-2-one.

Embodiment 47. A compound of formula (I), which is 5-(1'-isopropyl-6'-oxo-1',6'-dihydro-[3,3'-bipyridin]-5-yl)-1-methylindolin-2-one.

Embodiment 48. A compound of formula (I) which is 5-(1'-isopropyl-6'-oxo-1',6'-dihydro-[3,3'-bipyridin]-5-yl)-1-methylindolin-2-one in pharmaceutically acceptable salt form.

Embodiment 49. A compound of formula (I) which is 5-(1'-isopropyl-6'-oxo-1',6'-dihydro-[3,3'-bipyridin]-5-yl)-1-methylindolin-2-one in monohydrate form.

Embodiment 50. A crystalline form of 5-(1'-isopropyl-6'-oxo-1',6'-dihydro-[3,3'-bipyridin]-5-yl)-1-methylindolin-2-one monohydrate.

Embodiment 51. Compound B as mentioned in Embodiment 44, or a pharmaceutically pharmaceutically acceptable salt thereof.

Embodiment 52. Compound C as mentioned in Embodiment 44, or a pharmaceutically acceptable salt thereof.

Embodiment 53. Compound D as mentioned in Embodiment 44, or a pharmaceutically acceptable salt thereof.

Embodiment 54. A pharmaceutical composition comprising a compound or pharmaceutically acceptable salt thereof according to any of embodiments 1 to 53 and one or more pharmaceutically acceptable carriers.

Embodiment 55. A pharmaceutical composition comprising a compound which is 5-(1'-isopropyl-6'-oxo-1',6'-dihydro-[3,3'-bipyridin]-5-yl)-1-methylindolin-2-one or pharmaceutically acceptable salt thereof and one or more pharmaceutically acceptable carriers.

Embodiment 56. A pharmaceutical composition comprising a compound which is Compound B as mentioned in Embodiment 44, or a pharmaceutically acceptable salt thereof.

Embodiment 57. A pharmaceutical composition comprising a compound which is Compound C as mentioned in Embodiment 44, or a pharmaceutically acceptable salt thereof.

Embodiment 58. A pharmaceutical composition comprising a compound which is Compound D as mentioned in Embodiment 44, or a pharmaceutically acceptable salt thereof.

Embodiment 59. A combination comprising a therapeutically effective amount of a compound or a pharmaceutically acceptable salt thereof according to any of embodiments 1 to 53 and one or more therapeutically active agents.

Embodiment 60. A combination comprising a therapeutically effective amount of a compound which is 5-(1'-isopropyl-6'-oxo-1',6'-dihydro-[3,3'-bipyridin]-5-yl)-1-methylindolin-2-one or a pharmaceutically acceptable salt thereof and one or more therapeutically active agents.

Embodiment 61. A pharmaceutical composition comprising a compound which is Compound B as mentioned in Embodiment 44, or a pharmaceutically acceptable salt thereof and one or more therapeutically active agents.

Embodiment 62. A pharmaceutical composition comprising a compound which is Compound C as mentioned in Embodiment 44, or a pharmaceutically acceptable salt thereof and one or more therapeutically active agents.

Embodiment 63. A pharmaceutical composition comprising a compound which is Compound D as mentioned in Embodiment 44, or a pharmaceutically acceptable salt thereof and one or more therapeutically active agents.

Embodiment 64. A method of inhibiting ALK-2 activity in a subject, wherein the method comprises administering to the subject a therapeutically effective amount of the compound according to any of embodiments 1 to 53 or a pharmaceutically acceptable salt thereof.

Embodiment 65. A compound according to any of embodiments 1 to 53 or a pharmaceutically acceptable salt thereof for use in treating a disorder or disease selected from anaemia of chronic disease, heterotopic ossification, fibrodysplasia ossificans progressiva or osteoporosis.

Embodiment 66. A method of treating a disorder or disease selected from anaemia of chronic disease, heterotopic ossification, fibrodysplasia ossificans progressiva, comprising administering to the subject a therapeutically effective amount of the compound according to any of embodiments 1 to 53 or a pharmaceutically acceptable salt thereof.

Embodiment 67. A method of treating a disorder or disease selected from anaemia of chronic disease, heterotopic ossification, fibrodysplasia ossificans progressiva, comprising administering to the subject a therapeutically effective amount of a pharmaceutical composition according to any of embodiments 54 to 58.

Embodiment 68. A method of treating anaemia of chronic disease comprising administering to the subject a therapeutically effective amount of any one of the following compounds: the compound 5-(5-(1-isopropyl-6-oxo-1,6-dihydropyridin-3-yl)pyridin-3-yl)-1-methylindolin-2-one; compound B as mentioned in embodiment 44; compound C as mentioned in embodiment 44; or compound D as mentioned in embodiment 44; or, in case of each of the four compounds just mentioned, a pharmaceutically acceptable salt thereof.

Embodiment 69. A method of treating heterotopic ossification comprising administering to the subject a therapeutically effective amount of any one of the following compounds; the compound 5-(5-(1-isopropyl-6-oxo-1,6-dihydropyridin-3-yl)pyridin-3-yl)-1-methylindolin-2-one; compound B as mentioned in embodiment 44; compound C as mentioned in embodiment 44; or compound D as mentioned in embodiment 44; or, in case of each of the four compounds just mentioned, a pharmaceutically acceptable salt thereof.

Embodiment 70. A method of treating fibrodysplasia ossificans progressiva comprising administering to the subject a therapeutically effective amount of any one of the following compounds: the compound 5-(5-(1-isopropyl-6-oxo-1,6-dihydropyridin-3-yl)pyridin-3-yl)-1-methylindolin-2-one; compound B as mentioned in embodiment 44; compound C as mentioned in embodiment 44; or compound D as mentioned in embodiment 44; or, in case of each of the four compounds just mentioned, a pharmaceutically acceptable salt thereof.

Embodiment 71. A pharmaceutical composition according to any of embodiments 51 or 52 for use in treating a disorder or disease selected from anaemia of chronic disease, heterotopic ossification, fibrodysplasia ossificans progressiva or osteoporosis.

Embodiment 72. The compound 5-(1'-isopropyl-6'-oxo-1',6'-dihydro-[3,3'-bipyridin]-5-yl)-1-methylindolin-2-one or a pharmaceutically acceptable salt thereof for use in treating anaemia of chronic disease.

Embodiment 73. The compound 5-(1'-isopropyl-6'-oxo-1',6'-dihydro-[3,3'-bipyridin]-5-yl)-1-methylindolin-2-one or a pharmaceutically acceptable salt thereof for use in treating heterotopic ossification.

Embodiment 74. The compound 5-(1'-isopropyl-6'-oxo-1',6'-dihydro-[3,3'-bipyridin]-5-yl)-1-methylindolin-2-one or a pharmaceutically acceptable salt thereof for use in treating fibrodysplasia ossificans progressiva.

Embodiment 75. The compound 5-(1'-isopropyl-6'-oxo-1',6'-dihydro-[3,3'-bipyridin]-5-yl)-1-methylindolin-2-one or a pharmaceutically acceptable salt thereof for use in treating osteoporosis.

Embodiment 76. A compound of formula (Ia) or a pharmaceutically acceptable salt thereof,

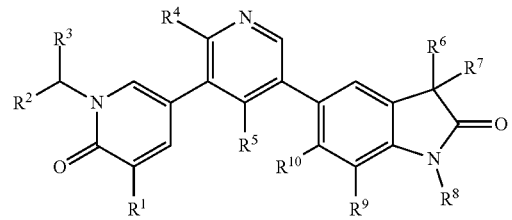

(Ia)

wherein
$R^1$ is hydrogen or $C_{1-4}$alkyl;
$R^2$ and $R^3$ independently represent hydrogen, $C_{1-6}$alkyl, $C_{1-6}$haloalkyl, $C_{1-6}$alkoxy, $C_{3-6}$cycloalkyl;
$R^4$ represents hydrogen or amino;
$R^5$ is hydrogen or fluorine;
$R^6$ and $R^7$ independently represent hydrogen or fluorine;
$R^8$ represents hydrogen, $C_{1-8}$alkyl;
$R^9$ represents hydrogen, halogen or $C_{1-4}$alkyl; and
$R^{10}$ represents hydrogen or halogen.

Embodiment 77. A compound of formula (Ia) or a pharmaceutically acceptable salt thereof,

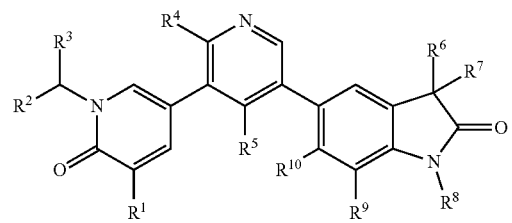

(Ia)

wherein
$R^1$ is hydrogen or $C_{1-4}$alkyl;
$R^2$ and $R^3$ independently represent hydrogen, $C_{1-6}$alkyl, $C_{1-6}$haloalkyl, $C_{1-6}$alkoxy, $C_{3-6}$cycloalkyl;
$R^4$ represents hydrogen;
$R^5$ is hydrogen or fluorine;
$R^6$ and $R^7$ independently represent hydrogen or fluorine;
$R^8$ represents hydrogen, $C_{1-3}$alkyl;
$R^9$ represents hydrogen or halogen; and
$R^{10}$ represents hydrogen or halogen.

Embodiment 78. A compound of formula (Ia) or a pharmaceutically acceptable salt thereof,

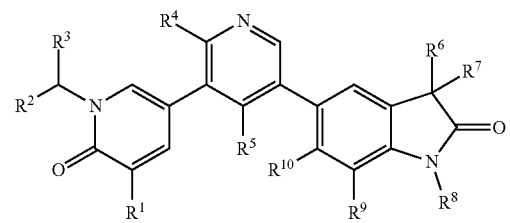

(Ia)

wherein
$R^1$ is hydrogen;
$R^2$ and $R^3$ independently represent hydrogen or methyl;

$R^4$ represents hydrogen;
$R^5$ is hydrogen;
$R^6$ and $R^7$ independently represent hydrogen or fluorine;
$R^8$ represents hydrogen or methyl;
$R^9$ represents hydrogen; and
$R^{10}$ represents hydrogen.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid salts by virtue of the presence of a basic pyridine and aminopyridine moiety.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In one embodiment, the present invention provides any one of 5-(1'-isopropyl-6'-oxo-1',6'-dihydro-[3,3'-bipyridin]-5-yl)-1-methylindolin-2-one, Compound B, Compound C and Compound D in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by ALK-2, or (ii) associated with ALK-2 activity, or (iii) characterized by activity (normal or abnormal) of ALK-2; or (2) reduce or inhibit the activity of ALK-2; or (3) reduce or inhibit the expression of ALK-2. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of ALK-2; or at least partially reduce or inhibit the expression of ALK-2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid.

Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

In one embodiment, the invention relates to 5-(1'-isopropyl-6'-oxo-1',6'-dihydro-[3,3'-bipyridin]-5-yl)-1-methylindolin-2-one in monohydrate form.

The compounds of the present invention, including salts, hydrates and solvates thereof, may inherently or by design form polymorphs.

In one embodiment, the invention relates to 5-(1'-isopropyl-6'-oxo-1',6'-dihydro-[3,3'-bipyridin]-5-yl)-1-methylindolin-2-one in crystalline form.

In one embodiment of the invention, there is provided crystalline 5-(1'-isopropyl-6'-oxo-1',6'-dihydro-[3,3'-bipyridin]-5-yl)-1-methylindolin-2-one monohydrate in substantially pure form.

As used herein, "substantially pure," when used in reference to crystalline 5-(1'-isopropyl-6'-oxo-1',6'-dihydro-[3,3'-bipyridin]-5-yl)-1-methylindolin-2-one monohydrate means having a purity greater than 90 weight %, including greater than 90, 91, 92, 93, 94, 95, 96, 97, 98, and 99 weight %, and also including equal to about 100 weight % of 5-(1'-isopropyl-6'-oxo-1',6'-dihydro-[3,3'-bipyridin]-5-yl)-1-methylindolin-2-one, based on the weight of the compound.

The presence of reaction impurities and/or processing impurities may be determined by analytical techniques known in the art, such as, for example, chromatography, nuclear magnetic resonance spectroscopy, mass spectrometry, or infrared spectroscopy.

In a more focused aspect, the invention relates to a crystalline form 5-(1'-isopropyl-6'-oxo-1',6'-dihydro-[3,3'-bipyridin]-5-yl)-1-methylindolin-2-one monohydrate which has an X-ray powder diffraction pattern with at least one, two or three peaks having angle of refraction 2 theta (θ) values selected from 9.5, 11.7, 14.8 and 16.0 when measured using $CuK_\alpha$ radiation, more particularly wherein said values are plus or minus 0.2° 2θ.

In one embodiment, the invention relates to a crystalline form of 5-(1'-isopropyl-6'-oxo-1',6'-dihydro-[3,3'-bipyridin]-5-yl)-1-methylindolin-2-one monohydrate which has an X-ray powder diffraction pattern with a peak at an angle of refraction 2θ value of 9.5 when measured using $CuK_\alpha$ radiation, more particularly wherein said value is plus or minus 0.2° 2θ.

In one embodiment, the invention relates to a crystalline form of 5-(1'-isopropyl-6'-oxo-1',6'-dihydro-[3,3'-bipyridin]-5-yl)-1-methylindolin-2-one monohydrate which has an X-ray powder diffraction pattern with a peak at an angle of refraction 2θ value of 11.7 when measured using $CuK_\alpha$ radiation, more particularly wherein said value is plus or minus 0.2° 2θ.

In one embodiment, the invention relates to a crystalline form of 5-(1'-isopropyl-6'-oxo-1',6'-dihydro-[3,3'-bipyridin]-5-yl)-1-methylindolin-2-one monohydrate which has an X-ray powder diffraction pattern with a peak at an angle of refraction 2θ value of 14.8 when measured using $CuK_\alpha$ radiation, more particularly wherein said value is plus or minus 0.2° 2θ.

In one embodiment, the invention relates to a crystalline form of 5-(1'-isopropyl-6'-oxo-1',6'-dihydro-[3,3'-bipyridin]-5-yl)-1-methylindolin-2-one monohydrate which has an X-ray powder diffraction pattern with a peak at an angle of refraction 2θ value of 16.0 when measured using $CuK_\alpha$ radiation, more particularly wherein said value is plus or minus 0.2° 2θ.

In one embodiment, the invention relates to a crystalline form of 5-(1'-isopropyl-6'-oxo-1',6'-dihydro-[3,3'-bipyridin]-5-yl)-1-methylindolin-2-one monohydrate which has an X-ray powder diffraction pattern substantially the same as the X-ray powder diffraction pattern shown in FIG. 1 when measured using $CuK_\alpha$ radiation. For details see Example 1.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

One of ordinary skill in the art will also appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention is not limited to the crystal form that provides an X-ray diffraction pattern completely identical to the X-ray diffraction pattern depicted in the accompanying FIG. 1 disclosed herein. Any crystal forms that provide X-ray diffraction patterns substantially identical to those disclosed in the accompanying FIG. 1 fall within the scope of the present invention. The ability to ascertain substantial identities of X-ray diffraction patterns is within the purview of one of ordinary skill in the art.

Typically, the compounds of formula (I) can be prepared according to the Schemes provided infra.

Scheme 1

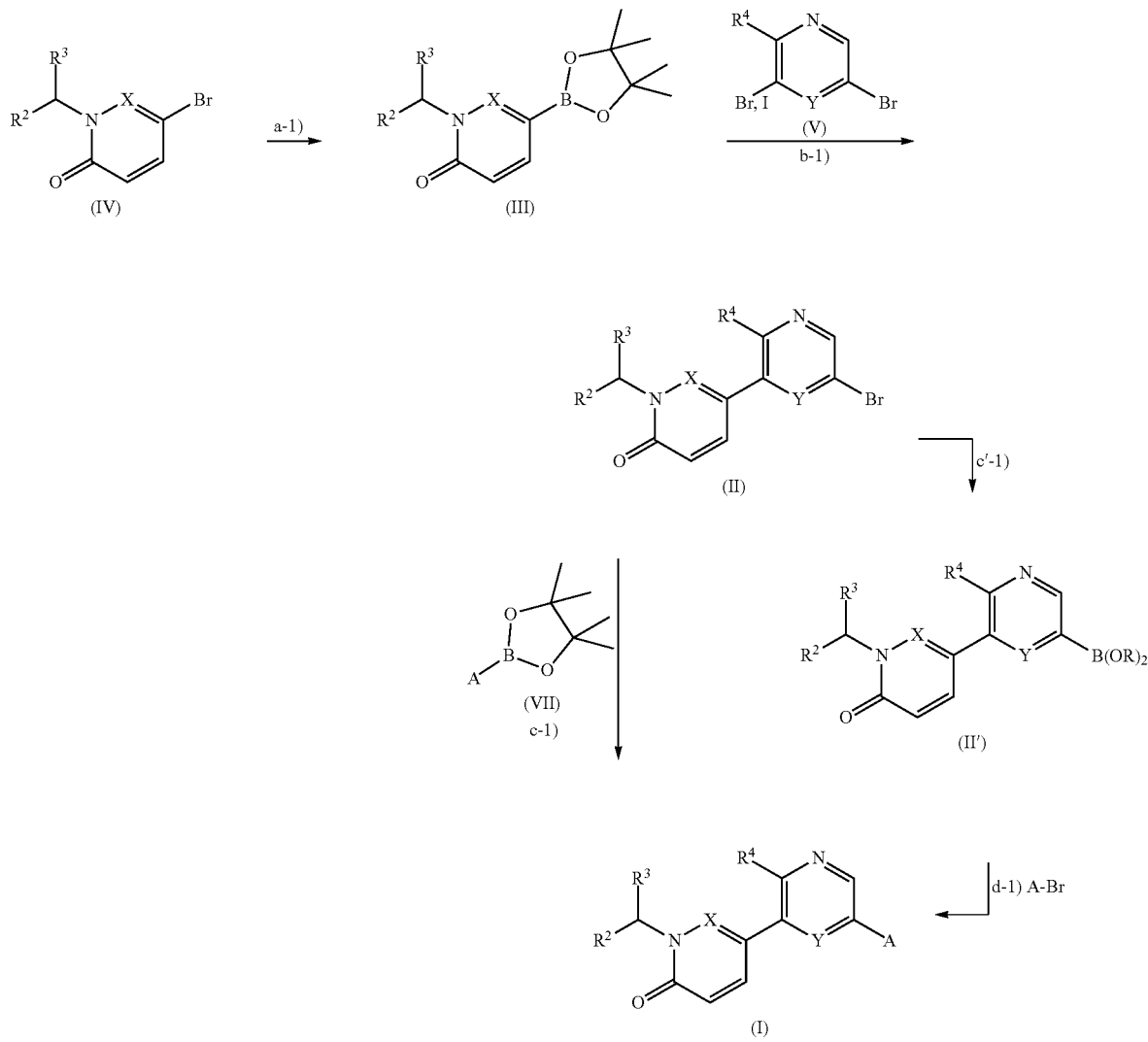

The process steps are described in more details below:

Step a-1): A compound of formula (III) in which $R^2$, $R^3$ and X are as defined under formula (I) may be obtained by reaction of a compound of formula (IV) in which $R^2$, $R^3$ and X are as defined under formula (I) with bis(pinacolato) diboron in the presence of a suitable base, e.g. potassium acetate, a suitable catalyst, e.g. $PdCl_2$(dppf), in a suitable solvent, e.g. dioxane.

Step b-1): A compound of formula (II) in which $R^2$, $R^3$, $R^4$, X and Y are as defined under formula (I) may be obtained by reaction of a compound of formula (III) in which $R^2$, $R^3$ and X are as defined under formula (I) with a compound of formula (V) in which $R^4$ and Y are as defined under formula (I) in the presence of a suitable base, e.g. potassium acetate, a suitable catalyst, e.g. $PdCl_2$(dppf), in a suitable solvent, e.g. dioxane.

Step c-1): A compound of formula (I) may be obtained by reaction of a compound of formula (II) in which $R^2$, $R^3$, $R^4$, X and Y are as defined under formula (I) with a compound of formula (VII) in which A is as defined under formula (I) in the presence of a suitable base, e.g. potassium carbonate, a suitable catalyst, e.g. $PdCl_2$(dppf), in a suitable solvent, e.g. acetonitrile. The compound of formula (VII) in which A is as defined under formula (I) can be prepared from the corresponding A-Br compound in the presence of a suitable base, e.g. potassium acetate, a suitable catalyst, e.g. $PdCl_2$(dppf), in a suitable solvent, e.g. dioxane.

Step c'-1): A compound of formula (II') in which $R^2$, $R^3$, $R^4$, X and Y are as defined under formula (I) and in which R may be hydrogen, an alkyl group or an alkylene group may be obtained by reaction of a compound of formula (II) in which $R^2$, $R^3$, $R^4$, X and Y are as defined under formula (I) with bis(pinacolato)diboron in the presence of a suitable base, e.g. potassium acetate, a suitable catalyst, e.g. $PdCl_2$(dppf), in a suitable solvent, e.g. dioxane.

Step d-1): A compound of formula (I) may be obtained followed by the reaction of a compound of formula (II') in which $R^2$, $R^3$, $R^4$, X and Y are as defined under formula (I) and in which R may be hydrogen, an alkyl group or an alkylene group with A-Br in which A is as defined under formula (I) in the presence of a suitable base, e.g. potassium carbonate, a suitable catalyst, e.g. $PdCl_2$(dppf), in a suitable solvent, e.g. acetonitrile.

Scheme 2

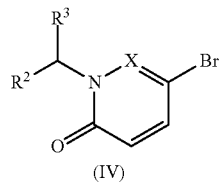
(IV)

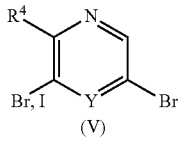
(V)

a-2) ↓ c-2) ↓ <span>(VII)</span>

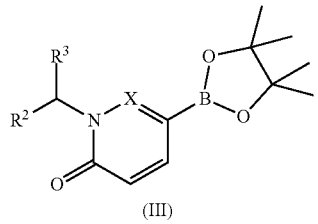
(III)

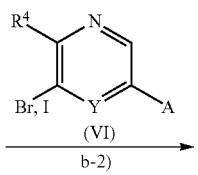
(VI)

b-2) →

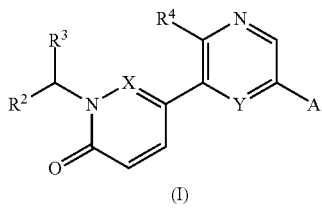
(I)

The process steps are described in more details below:

Step a-2): A compound of formula (III) in which $R^2$, $R^3$ and X are as defined under formula (I) may be obtained by reaction of a compound of formula (IV) in which $R^2$, $R^3$ and X are as defined under formula (I) with bis(pinacolato) diboron in the presence of a suitable base, e.g. potassium acetate, a suitable catalyst, e.g. $PdCl_2(dppf)$, in a suitable solvent, e.g. dioxane.

Step b-2): A compound of formula (I) may be obtained by reacting a compound of formula (III) in which $R^2$, $R^3$ and X are as defined under formula (I) with a compound of formula (VI) in which $R^4$, A and Y are as defined under formula (I) in the presence of a suitable base, e.g. potassium carbonate, a suitable catalyst, e.g. $PdCl_2(dppf)$, in a suitable solvent, e.g. dioxane.

Step c-2): A compound of formula (VI) in which $R^4$, A and Y are as defined under formula (I) may be obtained by reaction of a compound of formula (V) in which Y and $R^4$ are as defined under formula (I) with a compound of formula (VII) in which A is as defined under formula (I) in the presence of a suitable catalyst, e.g. $PdCl_2(dppf)$, a suitable case, e.g. cesium carbonate, in a suitable solvent, e.g. DME.

In a further aspect, the invention relates to a process for the preparation of a compound of formula (I) as defined herein, in free form or in pharmaceutically acceptable form, comprising the steps of:
a) coupling a compound of formula (II) in which $R^2$, $R^3$, $R^4$, X and Y are as defined under formula (I) with a compound of formula (VII) in which A is as defined under formula (I) to give a compound of formula (I);
b) recovering the so obtainable compound of formula (I) in free form or in pharmaceutically acceptable salt form.

In a further aspect, the invention relates to a process for the preparation of a compound of formula (I) as defined herein, in free form or in pharmaceutically acceptable form, comprising the steps of:

a) coupling a compound of formula (II') in which $R^2$, $R^3$, $R^4$, X and Y are as defined under formula (I) and in which R may be hydrogen, an alkyl group or an alkylene group with a compound of formula (A-Br) in which A is as defined under formula (I) to give a compound of formula (I);
b) recovering the so obtainable compound of formula (I) in free form or in pharmaceutically acceptable salt form.

In a further aspect, the invention relates to a process for the preparation of a compound of formula (I) as defined herein, in free form or in pharmaceutically acceptable form, comprising the steps of:
a) coupling a compound of formula (III) in which $R^2$, $R^3$ and X are as defined under formula (I) with a compound of formula (VI) in which $R^4$, A and Y are as defined under formula (I) to give a compound of formula (I);
b) recovering the so obtainable compound of formula (I) in free form or in pharmaceutically acceptable salt form.

In an additional embodiment, there is provided a compound of formula (II) or pharmaceutically acceptable salt thereof

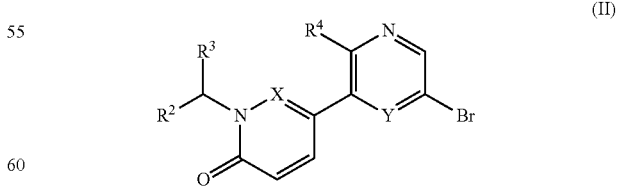
(II)

wherein $R^2$, $R^3$, $R^4$, X and Y are as defined in relation to a compound of formula (I).

In an additional embodiment, there is provided a compound of formula (II') or pharmaceutically acceptable salt thereof

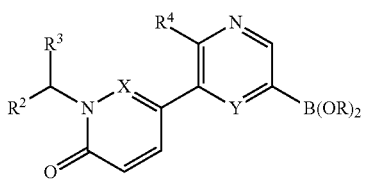

(II')

wherein $R^2$, $R^3$, $R^4$, X and Y are as defined in relation to a compound of formula (I) and wherein R is hydrogen, an alkyl or an alkylene group.

In an additional embodiment, there is provided a compound of formula (III) or pharmaceutically acceptable salt thereof

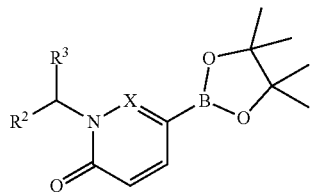

(III)

wherein $R^2$, $R^3$ and X are as defined in relation to a compound of formula (I).

In an additional embodiment, there is provided a compound of formula (VI) or a pharmaceutically acceptable salt thereof

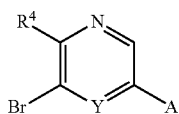

(VI)

wherein $R^4$, Y and A are as defined in relation to a compound of formula (I).

Compounds of formula (II), (II'), (Ill) and (VI) are useful in the preparation of compounds of the invention, e.g., compounds of Formula (I).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, rectal administration, transdermal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula (I) in free form or in pharmaceutically acceptable salt form, exhibit valuable pharmacological properties, e.g. ALK-2 modulating properties, e.g. as indicated in vitro and in vivo tests as provided in the next sections, and are therefore indicated for therapy or for use as research chemicals, e.g. as tool compounds.

The compounds of the invention demonstrate favourable pharmacokinetic properties, are non-toxic and demonstrate few side-effects. In particular, the compounds of the invention are selective for ALK-2 over other receptors. Furthermore, the ideal drug candidate will be in a form that is stable, non-hygroscopic and easily formulated. The present invention relates to compounds which are selective ALK-2 inhibitors.

Compounds of the invention may be useful in the treatment of an indication selected from: anaemia of chronic disease, heterotopic ossification, fibrodysplasia ossificans progressiva, osteoporosis or pulmonary arterial hypertension.

Without wishing to be bound by theory, it is thought that the compounds of the invention being selective ALK-2 inhibitors reduce/inhibit BMP signaling and the abnormal tissue repair associated with it.

Without wishing to be bound by theory, it is thought that inflammation-driven elevation of liver hepcidin expression (key negative regulator of iron bioavailability), as cause of anemia of chronic diseases (ACD), can be reduced by inhibiting BMP signaling with ALK-2 inhibitors, resulting in an increase of serum iron levels.

By "anaemia of chronic diseases" is meant for example anaemia associated with chronic inflammatory conditions, i.e. chronic kidney disease, chronic colitis etc.

Thus, as a further embodiment, the present invention provides the use of a compound of formula (I) or subformulae thereof (Ia), (Ia-1), (Ib), (Ib-1), (Ic), (Ic-1), (Id), (Id-1), (Ie), (Ie-1) or a pharmaceutically acceptable salt thereof in therapy. In a further embodiment, the therapy is selected from a disease which may be treated by inhibition of ALK-2 receptor. In another embodiment, the disease is selected from anaemia of chronic disease, heterotopic ossification, fibrodysplasia ossificans progressiva or osteoporosis.

Thus, as a further embodiment, the present invention provides a compound of formula (I) or subformulae thereof (Ia), (Ia-1), (Ib), (Ib-1), (Ic), (Ic-1), (Id), (Id-1), (Ie), (Ie-1) or a pharmaceutically acceptable salt thereof for use in therapy. In a further embodiment, the therapy is selected from a disease which may be treated by inhibition of ALK-2 receptor. In another embodiment, the disease is selected from anaemia of chronic disease, heterotopic ossification, fibrodysplasia ossificans progressive or osteoporosis.

In another embodiment, the invention provides a method of treating a disease which is treated by inhibition of ALK-2 receptor comprising administration of a therapeutically acceptable amount of a compound of formula (I) or subformulae thereof (Ia), (Ia-1), (Ib), (Ib-1), (Ic), (Ic-1), (Id), (Id-1), (Ie), (Ie-1) or a pharmaceutically acceptable salt thereof. In a further embodiment, the disease is selected from anaemia of chronic disease, heterotopic ossification, fibrodysplasia ossificans progressiva or osteoporosis.

Thus, as a further embodiment, the present invention provides the use of a compound of formula (I) or subformulae thereof (Ia), (Ia-1), (Ib), (Ib-1), (Ic), (Ic-1), (Id), (Id-1), (Ie), (Ie-1) or a pharmaceutically acceptable salt thereof for the manufacture of a medicament. In a further embodiment, the medicament is for treatment of a disease which may be treated by inhibition of ALK-2 receptor. In another embodiment, the disease is selected from anaemia of chronic disease, heterotopic ossification, fibrodysplasia ossificans progressive or osteoporosis.

In one embodiment of the present invention, there is provided 5-(1'-isopropyl-6'-oxo-1',6'-dihydro-[3,3'-bipyridin]-5-yl)-1-methylindolin-2-one or a pharmaceutically acceptable salt thereof for use in the treatment of anaemia of chronic disease, heterotopic ossification, fibrodysplasia ossificans progressiva, osteoporosis or pulmonary arterial hypertension.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg or about 0.5-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the in vitro methods described in examples 53 to 55. Further in vivo methods are described in examples 56 to 60.

Preferred compounds of the invention exhibit efficacy in the assays described in examples 53 to 55 with an $IC_{50}$ of less than 1 µM.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) or subformulae thereof (Ia), (Ia-1), (Ib), (Ib-1), (Ic), (Ic-1), (Id), (Id-1), (Ie), (Ie-1) and at least one other therapeutic agent as a combined preparation for simultaneous, separate or sequential use in therapy. In one embodiment, the therapy is the treatment of a disease or condition mediated by ALK-2. Products provided as a combined preparation include a composition comprising the compound of formula (I) or subformulae thereof (Ia), (Ia-1), (Ib), (Ib-1), (Ic), (Ic-1), (Id), (Id-1), (Ie), (Ie-1) and the other therapeutic agent(s) together in the same pharmaceutical composition, or the compound of formula (I) or subformulae thereof (Ia), (Ia-1), (Ib), (Ib-1), (Ic), (Ic-1), (Id), (Id-1), (Ie), (Ie-1) and the other therapeutic agent(s) in separate form, e.g. in the form of a kit.

In one embodiment, the invention provides a pharmaceutical composition comprising a compound of formula (I) or subformulae thereof (Ia), (Ia-1), (Ib), (Ib-1), (Ic), (Ic-1), (Id), (Id-1), (Ie), (Ie-1) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I) or subformulae thereof (Ia), (Ia-1), (Ib), (Ib-1), (Ic), (Ic-1), (Id), (Id-1), (Ie), (Ie-1). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or subformulae thereof (Ia), (Ia-1), (Ib), (Ib-1), (Ic), (Ic-1), (Id), (Id-1), (Ie), (Ie-1) for treating a disease or condition mediated by ALK-2 wherein the medicament is prepared for administration with another therapeutic agent. The invention also provides the use of another therapeutic agent for treating a disease or condition mediated by ALK-2, wherein the medicament is administered with a compound of formula (I) or subformulae thereof (Ia), (Ia-1), (Ib), (Ib-1), (Ic), (Ic-1), (Id), (Id-1), (Ie), (Ie-1).

The invention also provides a compound of formula (I) or subformulae thereof (Ia), (Ia-1), (Ib), (Ib-1), (Ic), (Ic-1), (Id), (Id-1), (Ie), (Ie-1) for use in a method of treating a disease or condition mediated by ALK-2, wherein the compound of formula (I) is prepared for administration with another therapeutic agent. The invention also provides another therapeutic agent for use in a method of treating a disease or condition mediated by ALK-2, wherein the other therapeutic agent is prepared for administration with a compound of formula (I) or subformulae thereof (Ia), (Ia-1), (Ib), (Ib-1), (Ic), (Ic-1), (Id), (Id-1), (Ie), (Ie-1). The invention also provides a compound of formula (I) or subformulae thereof (Ia), (Ia-1), (Ib), (Ib-1), (Ic), (Ic-1), (Id), (Id-1), (Ie), (Ie-1) for use in a method of treating a disease or condition mediated by ALK-2, wherein the compound of formula (I) or subformulae thereof (Ia), (Ia-1), (Ib), (Ib-1), (Ic), (Ic-1), (Id), (Id-1), (Ie), (Ie-1) is administered with another therapeutic agent. The invention also provides another therapeutic agent for use in a method of treating a disease or condition mediated by ALK-2, wherein the other therapeutic agent is administered with a compound of formula (I) or subformulae thereof (Ia), (Ia-1), (Ib), (Ib-1), (Ic), (Ic-1), (Id), (Id-1), (Ie), (Ie-1).

The invention also provides the use of a compound of formula (I) or subformulae thereof (Ia), (Ia-1), (Ib), (Ib-1), (Ic), (Ic-1), (Id), (Id-1), (Ie), (Ie-1) for treating a disease or condition mediated by ALK-2, wherein the patient has previously (e.g. within 24 hours) been treated with another therapeutic agent. The invention also provides the use of another therapeutic agent for treating a disease or condition mediated by ALK-2, wherein the patient has previously (e.g. within 24 hours) been treated with a compound of formula (I) or subformulae thereof (Ia), (Ia-1), (Ib), (Ib-1), (Ic), (Ic-1), (Id), (Id-1), (Ie), (Ie-1).

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

EXAMPLES

Abbreviations

δ Chemical shift
ACN Acetonitrile
AcOH Acetic acid
BINAP 2,2'-bis(diphenylphosphino)-1,1'-binaphthyl
Boc Tert-butoxycarbonyl
$Cs_2CO_3$ Cesium carbonate
DCE 1,2-Dichloroethane
DCM Methylene chloride
DMAP 4-Dimethylaminopyridine
DME Dimethoxyethane
DMF Dimethylformamide
DMSO Dimethyl sulfoxide
DMSO-$d_6$ Deuterated Dimethyl sulfoxide
eq equivalent
$Et_2O$ diethyl ether
EtOAc Ethyl acetate
EtOH Ethanol
ESI ElectroSpray Ionisation
HBr Hydrobromic acid
HCl Hydrochloric acid
hr hour(s)
HV High Vacuum
iPrOH isopropyl alcohol
$K_2CO_3$ Potassium carbonate
KOAc Potassium Acetate
LC-MRM Liquid chromatography with multiple reaction monitoring
$Me_2SO_4$ Dimethylsulfate
MeOH Methanol
$MgSO_4$ Magnesium sulfate
MHz Mega Hertz
min minute(s)
mL milliliter
Mp melting point
MS Mass Spectroscopy
MW Micro Waves
$Na_2CO_3$ Sodium carbonate
$NaBH(OAc)_3$ Sodium Triacetoxyborohydride
NaH Sodium Hydride
$NaHCO_3$ Sodium bicarbonate
NaOMe Sodium methoxide
NaOtBu Sodium tert-butoxide
NBS N-bromosuccinimide
NMR Nuclear Magnetic Resonance
$Pd_2(dba)_3$ Tris(dibenzylideneacetone)dipalladium (0)
$PdCl_2(dppf)$ [1,1'-Bis(diphenylphosphino)ferrocene]palladium (II) dichloride
$PdCl_2(dppf).CH_2Cl_2$ [1,1'-Bis(diphenylphosphino)ferrocene]palladium (II) dichloride dichloromethane complex
ppm parts-per-million
Rf retardation factor
Rt Retention time
RT Room Temperature
SPE Solid phase extraction
TEA Triethylamine
TFA Trifluoroacetic acid
TLC thin layer chromatography
UPLC Ultra Performance Liquid Chromatography
Analytical Instruments
UPLC-MS
Column: Waters Acquity HSS T3, 1.8 µm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=acetonitrile+0.04% formic acid. Detection UV/VIS (DAD), ESI (+/−). Mass spectrometer range: 100-1200 Da.
LC-MS
Column: Waters y C8, 3.5 µm, 2.1×50 mm, oven at 50° C. Flow: 1.0 mL/min. Gradient: 10% to 95% B in 2.0 min. then 95% B for 1.0 min; A=water+0.1% TFA, B=acetonitrile+0.1% TFA. Detection UV/VIS (DAD), ESI (+/−). Mass spectrometer range: 100-800 Da.

Starting materials and reagents are either commercially available or may be prepared by one skilled in the art using methods described in the chemical literature and in the synthetic examples below.

Synthetic Examples

Intermediates

Intermediate 1:
5-(5-bromopyridin-3-yl)-1-methylindolin-2-one

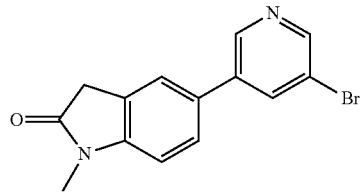 [SMILES: CN1C(=O)Cc2cc(-c3cncc(Br)c3)ccc21]

Step 1.1: 1-methyl-5-(4,4,5,5-tetramethyl-1,3,2-dioxaborolan-2-yl)indolin-2-one

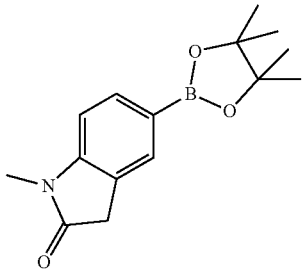

Method A 5-(4,4,5,5-tetramethyl-1,3,2-dioxaborolan-2-yl)indolin-2-one (10 g, 38.6 mmol) was added in toluene (250 mL). The mixture was cooled down to 0° C. and NaH 60% in mineral oil (2.315 g, 57.9 mmol) was added portionwise. The reaction mixture was allowed to warm up and stir at RT for 30 min. Dimethyl sulfate (5.53 mL, 57.9 mmol) was added and the reaction mixture was heated up and stirred at 60° C. for 3 hr, cooled down to 5° C. and quenched with water (50 mL). The reaction mixture was diluted with EtOAc and washed with saturated aqueous $NaHCO_3$ solution and brine. The organic layer was dried over $MgSO_4$, filtered and concentrated under reduced pressure to afford the title product (11.3 g, 36.0 mmol, 93% yield) as brown solid. Rt=1.03 min (UPLC-MS); ESI-MS=274.2 [M+1]$^+$ (UPLC-MS); $^1$H NMR (400 MHz, DMSO-$d_6$) δ ppm 1.29 (s, 12H) 3.13 (s, 3H) 3.55 (s, 2H) 6.99 (d, J=7.82 Hz, 1H) 7.53 (s, 1H) 7.61 (d, J=7.95 Hz, 1H).

Method B

A brown suspension of 5-(4,4,5,5-tetramethyl-1,3,2-dioxaborolan-2-yl)indolin-2-one (50 g, 193 mmol) in toluene (1.2 L) under $N_2$ atmosphere was stirred at RT for 30 min. The reaction mixture was cooled down to 0° C. and NaH 60% in mineral oil (10.03 g, 251 mmol) was added portionwise (exothermic addition). The resulting mixture was allowed to warm up and stir at RT for 30 min. A solution of dimethylsulfate (0.024 L, 251 mmol) in toluene (50 mL) was added dropwise over 15 min into the reaction and the resulting mixture was heated up and stirred at 60° C. for 3 h 15 min. The brownish turbid mixture was cooled down to 0-5° C. and quenched slowly with water added dropwise (150 mL) under vigorous stirring. The mixture was extracted with EtOAc (2×1 L). The combined organic layers were washed with water (2×0.5 L) and brine (0.5 L). The aqueous layer was back extracted with EtOAc (0.5 L). The combined organic layers were dried over $Na_2SO_4$, filtered and concentrated under reduced pressure. The crude material was purified by silica gel column chromatography (340 g $SiO_2$, Heptane/EtOAc 4:1 to 1:1) to afford the title product (30.0 g, 110 mmol, 56.9% yield) as beige material. Rt=1.03 min (UPLC-MS); ESI-MS=274.2 [M+H]$^+$ (UPLC-MS).

Intermediate 1:
5-(5-bromopyridin-3-yl)-1-methylindolin-2-one

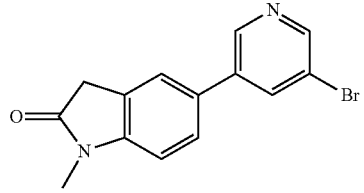 [SMILES: CN1C(=O)Cc2cc(-c3cncc(Br)c3)ccc21]

Method A

A 500 mL round-bottomed flask was charged with 3,5-dibromopyridine (7 g, 29.5 mmol), 1-methyl-5-(4,4,5,5-tetramethyl-1,3,2-dioxaborolan-2-yl)indolin-2-one (Step 1.1—method A) (9.74 g, 31 mmol) and $Cs_2CO_3$ (19.26 g, 59.1 mmol) in DME (230 mL) and water (23 mL) (ratio 10:1) to give a brown suspension. $PdCl_2(dppf)$ (2.162 g, 2.95 mmol) was added and the reaction mixture was heated up and stirred at 80° C. for 3 hr. The reaction mixture was diluted with EtOAc and washed with saturated aqueous $NaHCO_3$ solution and brine. The organic layer was dried over $MgSO_4$, filtered through a pad of Celite and concentrated under reduced pressure. The crude product was purified by flash column chromatography on silica gel (Cyclohexane/EtOAc 10 to 80% EtOAc) to afford the title product (3.8 g, 11.91 mmol, 40.3% yield) as a yellow solid. Rt=0.90 min (UPLC-MS); ESI-Ms=303.0/305.0 [M+1]$^+$ (UPLC-MS); $^1$H NMR (400 MHz, DMSO-$d_6$) δ ppm 3.17 (s, 3H) 3.63 (s, 2H) 7.12 (d, J=8.80 Hz, 1H) 7.71-7.76 (m, 2H) 8.33 (t, J=2.08 Hz, 1H) 8.65 (d, J=2.08 Hz, 1H) 8.88 (d, J=1.96 Hz, 1H).

Method B

DME (750 mL) and water (75 mL, previously degassed three times under vacuum and flushed with $N_2$) were stirred for 10 min under $N_2$ at RT. 3,5-dibromopyridine (18.21 g, 77 mmol), 1-methyl-5-(4,4,5,5-tetramethyl-1,3,2-dioxaborolan-2-yl)indolin-2-one (Step 1.1—method B) (20 g, 73.2 mmol) and $Cs_2CO_3$ (47.7 g, 146 mmol) were added and the resulting mixture was stirred at RT for 10 min. $PdCl_2(dppf)$ .$CH_2C2$ complex (1.794 g, 2.197 mmol) was added and the resulting mixture was heated up and stirred at 80° C. for 4 h 15 min. The reaction mixture was cooled down to 10° C. and quenched carefully with a cold aqueous $NaHCO_3$ solution (1.5 L) and water (1 L) and stirred vigorously for 5 min. The aqueous layer was extracted with EtOAc (3×2 L). The combined organic layers were washed with water (2×0.5 L) and brine (0.2 L), dried over $Na_2SO_4$, filtered and concentrated under reduced pressure. The crude product was purified by silica gel column chromatography (2 runs, 340 g $SiO_2$, Heptane/EtOAc 2:1 to 0:1) to afford the title product (7.1 g, 23.42 mmol, 32.0% yield) as yellow orange solid. Rt=0.90 min (UPLC-MS); ESI-MS=303.1/305.1 [M+H]$^+$ (UPLC-MS).

Intermediate A1: 1-isopropyl-5-(4,4,5,5-tetramethyl-1,3,2-dioxaborolan-2-yl)pyridin-2(1H)-one Step A1.1: 5-bromo-1-isopropylpyridin-2(1H)-one

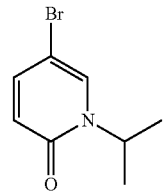

Method A

To a stirred solution of 5-bromopyridin-2(1H)-one (11.59 g, 66.6 mmol) in DME (150 mL) was added $Cs_2CO_3$ (28.2 g, 87 mmol) at RT followed by 2-iodopropane (Fluka) (8.64 mL, 87 mmol). The reaction mixture was heated up and stirred at 80° C. for 3 hr. The reaction was diluted with EtOAc and washed with aqueous $NaHCO_3$ solution and brine, dried over anhydrous $MgSO_4$, filtered and concentrated under reduced pressure. The crude product was purified by flash chromatography on silica gel (DCM/MeOH 0 to 20% MeOH) to afford the title product (10.0 g, 46.3 mmol, 69.5% yield). Rt=0.73 min (UPLC-MS); ESI-MS=216.0/218.0 [M+1]$^+$ (UPLC-MS); $^1$H NMR (400 MHz, DMSO-$d_6$) δ ppm 1.30 (d, J=6.85 Hz, 6H) 4.99 (quin, J=6.85 Hz, 1H) 6.36 (d, J=9.66 Hz, 1H) 7.49 (dd, J=9.66, 2.81 Hz, 1H) 7.97 (d, J=2.81 Hz, 1H).

Method B 2-hydroxy-5-bromopyridine (308.8 g, 1.739 mol) was added to DME (3.9 L) under mechanical stirring, under $N_2$ atmosphere at RT. After 10 min, $Cs_2CO_3$ (737 g, 2.261 mol) was added to the beige suspension. 2-iodopropane (0.226 L, 2.261 mmol) was added and the resulting mixture was heated up and stirred at 80° C. for 4 hr (white fine suspension). The reaction was cooled down to RT and stopped. The reaction mixture was concentrated to 50% of the initial volume under reduced pressure, quenched with saturated aqueous $NaHCO_3$ solution (1.5 L) and water (2.5 L) under mechanical stirring. The aqueous layer was extracted with EtOAc (3×4 L). The combined organic layers were washed with water (2×2 L) and brine (2 L), dried over $Na_2SO_4$, filtered and concentrated under reduced pressure. The crude product was purified by silica gel column chromatography (7 kg $SiO_2$, Heptane/EtOAc) to afford the title product (222 g, 1.027 mmol, 59.1% yield) as beige yellow product. Rt=0.73 min (UPLC-MS); ESI-MS=216.1/218.0 [M+H]$^+$ (UPLC-MS).

Intermediate A1: 1-isopropyl-5-(4,4,5,5-tetramethyl-1,3,2-dioxaborolan-2-yl)pyridin-2(1H)-one

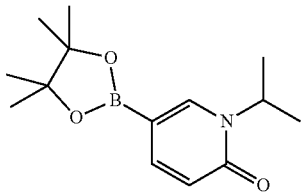 [SMILES: CC(C)n1cc(B2OC(C)(C)C(C)(C)O2)ccc1=O]

Method A

To a stirred solution of 5-bromo-1-isopropylpyridin-2(1H)-one (Step A1.1—method A) (10 g, 46.3 mmol) in Dioxane (150 mL) were added Bis(pinacolato)diboron (14.1 g, 55.5 mmol), KOAc (6.08 g, 93 mmol) and PdCl$_2$(dppf) (3.39 g, 4.63 mmol). The reaction mixture was heated up and stirred at 90° C. for 2 hr. Solvent was partially evaporated under reduced pressure, passed through a pad of Celite; the pad was washed with EtOAc and the resulting filtrate was concentrated under reduced pressure. The residue was diluted with EtOAc and aqueous NaHCO$_3$ solution, both phases separated and the aqueous layer was extracted with EtOAc. The combined organic layers were washed with brine, dried over MgSO$_4$, filtered and concentrated under reduced pressure to afford, without further purification, the title product (20.69 g, 39.3 mmol, 85% yield) as a dark oil. Rt=0.98 min (UPLC-MS); ESI-MS=264.2 [M+1]$^+$ (UPLC-MS).

Method B

To a stirred yellow clear solution of 5-bromo-1-isopropylpyridin-2(1H)-one (Step A1.1—method B) (208 g, 963 mmol) in dioxane (2.1 L) under N$_2$ atmosphere at RT were successively added Bis(pinacolato)diboron (367 mg, 1444 mmol), PdCl$_2$(dppf).CH$_2$Cl$_2$ complex (39.3 g, 48.1 mmol) and KOAc (189 g, 1925 mmol). The resulting mixture was heated up and stirred at 90° C. for 6 h 15 min. The reaction mixture was cooled down to RT, quenched with an aqueous NaHCO$_3$ solution (2.5 L) and water (2 L) and stirred at RT for 10 min until gas evolution ceased. The aqueous layer was extracted with EtOAc (3×5 L). The combined organic layers were washed with water (2×5 L) and brine (4 L), dried over Na$_2$SO$_4$, filtered and concentrated under reduced pressure to afford a brown oil. The crude material was first filtered through a pad of silica gel (200 g) and purified by silica gel column chromatography (3 kg SiO$_2$, Heptane/EtOAc) to afford the title product (94.7 g, 324 mmol, 33.6% yield) as beige-brown oily product. Rt=0.99 min (UPLC-MS); ESI-MS=264.2 [M+H]$^+$ (UPLC-MS).

Intermediate A2: 1-isopropyl-3-methoxy-5-(4,4,5,5-tetramethyl-1,3,2-dioxaborolan-2-yl)pyridin-2(1H)-one Step A2.1:
5-bromo-1-isopropyl-3-methoxypyridin-2(1H)-one

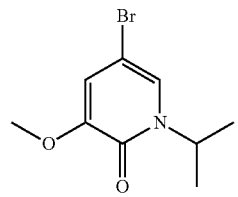

The title compound was prepared in a similar manner as described for Step A1.1—method A using 5-bromo-3-methoxypyridin-2(1H)-one to afford the title product without further purification. Rt=0.75 min (UPLC-MS); ESI-MS=245.9/248.0 [M+1]$^+$ (UPLC-MS).

1-isopropyl-3-methoxy-5-(4,4,5,5-tetramethyl-1,3,2-dioxaborolan-2-yl)pyridine 2(1H)-one

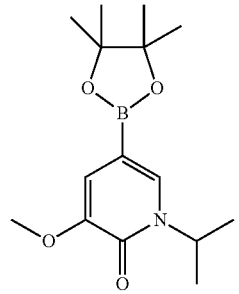 [SMILES: COc1cc(B2OC(C)(C)C(C)(C)O2)cn(C(C)C)c1=O]

The title compound was prepared in analogy to the procedure described in Intermediate A1—method A using 5-bromo-1-isopropyl-3-methoxypyridin-2(1H)-one (Step A2.1) at 90° C. for 1 hr to afford the title product without further purification. Rt=0.97 min (UPLC-MS); ESI-MS=294.1 [M+1]$^+$ (UPLC-MS).

Intermediate A3: 1-isopropyl-3-methyl-5-(4,4,5,5-tetramethyl-1,3,2-dioxaborolan-2-yl)pyridin-2(1H)-one

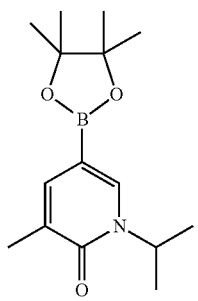 [SMILES: Cc1cc(B2OC(C)(C)C(C)(C)O2)cn(C(C)C)c1=O]

Step A3.1: 5-bromo-3-methylpyridin-2(1H)-one

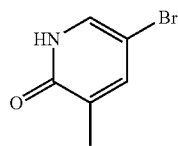

A MW vial was charged with 5-bromo-2-fluoro-3-methylpyridine (1 g, 5.26 mmol), $Cs_2CO_3$ (3.77 g, 11.58 mmol) and DMSO (15 ml), the vial was sealed and the resulting mixture was heated up and stirred at 120° C. for 4 hr. The reaction mixture was diluted with EtOAc and washed with aqueous $NaHCO_3$ solution and brine. The organic layer was dried over $Na_2SO_4$, filtered and concentrated under reduced pressure. The crude material was purified by flash column chromatography on silica gel (Cyclohexane/10 to 100% EtOAc) to afford the title product (130 mg, 0.691 mmol, 13.14% yield). Rt=0.57 min (UPLC-MS); ESI-MS=187.9/190.0 [M+1]$^+$ (UPLC-MS); $^1$H NMR (400 MHz, DMSO-$d_6$) δ ppm 1.98 (s, 3H) 7.49 (s, 1H) 7.45 (s, 1H) 11.73 (br. s., 1H).

Step A3.2: 5-bromo-1-isopropyl-3-methylpyridin-2(1H)-one

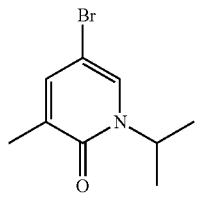

The title compound was prepared in analogy to the procedure described in Step A1.1 (method A) using 5-bromo-3-methylpyridin-2(1H)-one (Step A3.1). The crude material was purified by flash column chromatography on silica gel (DCM/0 to 15% MeOH). Rt=0.87 min (UPLC-MS); ESI-MS=230.0/232.0 [M+1]$^+$ (UPLC-MS).

1-isopropyl-3-methyl-5-(4,4,5,5-tetramethyl-1,3,2-dioxaborolan-2-yl)pyridin-2(1H)-one A 10 mL round bottomed flask was charged with 5-bromo-1-isopropyl-3-methylpyridin-2(1H)-one (Step A3.2) (108 mg, 0.469 mmol), Bis(pinacolato)diboron (143 mg, 0.563 mmol) in Dioxane (2 mL) to give an orange solution. KOAc (115 mg, 1.173 mmol) was added, followed by $PdCl_2(dppf)\cdot CH_2Cl_2$ adduct (38.3 mg, 0.047 mmol) and the mixture was heated up and stirred overnight at 80° C. The reaction mixture was filtered through a pad of silica gel and the resulting filtrate was concentrated under reduced pressure to afford the title product (150 mg, 0.222 mmol, 47.3% yield) as a black oil. Rt=1.09 min (UPLC-MS); ESI-MS=278.2 [M+1]$^+$ (UPLC-MS).

Intermediate A4: 1-(pentan-3-yl)-5-(4,4,5,5-tetramethyl-1,3,2-dioxaborolan-2-yl)pyridin-2(1H)-one

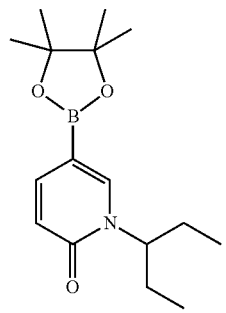 [SMILES: CCC(CC)n1cc(B2OC(C)(C)C(C)(C)O2)ccc1=O]

Step A4.1: 5-bromo-1-(pentan-3-yl)pyridin-2(1H)-one

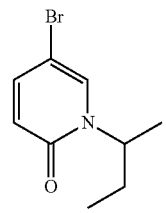

The title compound was prepared in analogy to the procedure described in Step A1.1 (method A) using 5-bromopyridin-2(1H)-one and 3-bromopentane at 80° C. overnight. Rt=0.89 min (UPLC-MS); ESI-MS=243.9/245.9 [M+1]$^+$ (UPLC-MS).

1-(pentan-3-yl)-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-(pentan-3-yl)pyridin-2(1H)-one (Step A4.1) at 90° C. for 1 hr. Rt=1.12 min (UPLC-MS); ESI-MS=292.1 [M+1]$^+$ (UPLC-MS).

Intermediate A5: 3-ethyl-1-isopropyl-5-(4,4,5,5-tetramethyl-1,3,2-dioxaborolan-2-yl)pyridin-2(1H)-one

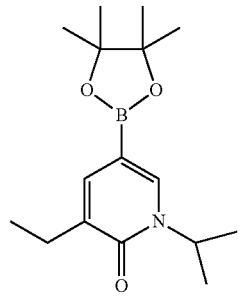 [SMILES: CCc1cc(B2OC(C)(C)C(C)(C)O2)cn(C(C)C)c1=O]

Step A5.1: 3-ethyl-2-methoxypyridine

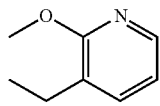

In a 25 mL round-bottomed flask, 2-chloro-3-ethylpyridine (290 mg, 2.048 mmol) was dissolved in MeOH (4 mL). A solution of 5M NaOMe in MeOH (4.1 mL, 20.48 mmol) was added and the mixture was heated up and stirred at 85° C. for 3 days. The reaction was quenched with ice and extracted twice with DCM. The combined organic layers were dried over MgSO$_4$, filtered, 1 mL of TFA was added and the solvent evaporated under reduced pressure to afford the title product (312 mg, 2.048 mmol, 100% yield) as trifluoroacetate salt. Rt=0.99 min (UPLC-MS); ESI-MS=138.1 [M+1]$^+$ (UPLC-MS).

Step A5.2: 5-bromo-3-ethyl-2-methoxypyridine

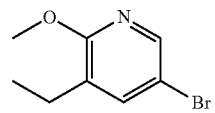

In a 25 mL round-bottomed flask, 3-ethyl-2-methoxypyridine (Step A5.1) (312 mg, 2.047 mmol) was dissolved in TFA (5 mL). 1,3-dibromo-5,5-dimethylhydantoin (702 mg, 2.456 mmol) was added at RT. After one day at RT, 2.2 eq of 1,3-dibromo-5,5-dimethylhydantoin was added and the mixture was stirred at RT for 4 more days. TFA was evaporated, the resulting mixture was adjusted to pH 6-7 with saturated aqueous NaHCO$_3$ solution and the aqueous layer was extracted twice with DCM. The combined organic layers were dried over MgSO$_4$, filtered and concentrated under reduced pressure. The precipitate obtained after trituration in DCM was filtered and the filtrate was concentrated under reduced pressure. The crude material was purified by flash column chromatography on silica gel (Cyclohexane/0 to 100% EtOAc) to afford the title product (119 mg, 0.523 mmol, 25.6% yield) as a yellow oil. Rt=1.24 min (UPLC-MS); ESI-MS=215.9/217.9 [M+1]$^+$ (UPLC-MS); 1H NMR (400 MHz, DMSO-d$_6$) δ ppm 1.13 (t, J=7.52 Hz, 3H) 2.51-2.58 (m, 2H) 3.87 (s, 3H) 7.75 (d, J=2.45 Hz, 1H) 8.12 (d, J=2.45 Hz, 1H).

Step A5.3: 5-bromo-3-ethylpyridin-2(1H)-one

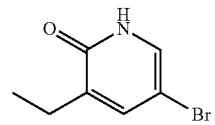

In a 25 mL round-bottomed flask, 5-bromo-3-ethyl-2-methoxypyridine (Step A5.2) (119 mg, 0.523 mmol) was dissolved in AcOH (1.5 mL). HBr 33% in AcOH (1.5 mL, 9.12 mmol) was added at RT and the resulting mixture was heated up and stirred at 90° C. for 1 hr. The reaction mixture was slowly poured into a saturated aqueous NaHCO$_3$ solution and adjusted to pH 6.5-7. The aqueous layer was extracted twice with EtOAc, the combined organic layers were washed with brine, dried over MgSO$_4$, filtered and concentrated under reduced pressure to afford the title product (128 mg, 0.538 mmol, quantitative yield) as a yellow solid. Rt=0.68 min (UPLC-MS); ESI-MS=201.9/203.9 [M+1]$^+$ (UPLC-MS).

Step A5.4: 5-bromo-3-ethyl-1-isopropylpyridin-2(1H)-one

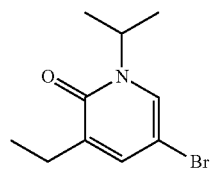

The title compound was prepared in analogy to the procedure described in Step A1.1 (method A) using 5-bromo-3-ethylpyridin-2(1H)-one (Step A5.3). The crude material was purified by flash column chromatography on silica gel (Cyclohexane/0 to 100% EtOAc. Rt=0.98 min (UPLC-MS); ESI-MS=244.0/246.0 [M+1]$^+$ (UPLC-MS).

3-ethyl-1-isopropyl-5-(4,4,5,5-tetramethyl-1,3,2-dioxaborolan-2-yl)pyridin-2(1H)-one The title compound was prepared in analogy to the procedure described in Intermediate A1 (method A) using 5-bromo-3-ethyl-1-isopropylpyridin-2(1H)-one (Step A5.4). The reaction mixture was filtered through a pad of Celite and the filtrate was concentrated under reduced pressure. Rt=1.17 min (UPLC-MS); ESI-MS=292.1 [M+1]$^+$ (UPLC-MS).

Intermediate A6: 1-Cyclobutyl-5-(4,4,5,5-tetramethyl-1,3,2-dioxaborolan-2-yl)pyridin-2(1H)-one

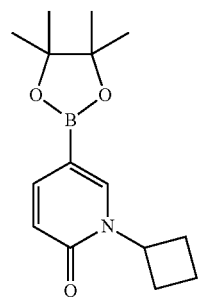 [SMILES: CC1(C)OB(c2ccc(=O)n(C3CCC3)c2)OC1(C)C]

Step A6.1: 5-bromo-1-cyclobutylpyridin-2(1H)-one

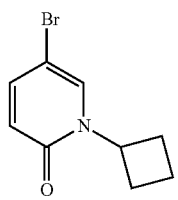 [SMILES: O=c1ccc(Br)cn1C1CCC1]

The title compound was prepared in analogy to the procedure described in Step A1.1 (method A) using 5-bromopyridin-2(1H)-one and bromocyclobutane. The crude material was purified by flash column chromatography on silica gel (DCM/0 to 20% MeOH). Rt=0.77 min (UPLC-MS); ESI-MS=227.9/229.9 [M+1]$^+$ (UPLC-MS).

1-Cyclobutyl-5-(4,4,5,5-tetramethyl-1,3,2-dioxaborolan-2-yl)pyridin-2(1H)-one

The title compound was prepared in analogy to the procedure described in Intermediate A1 (method A) using 5-bromo-1-cyclobutylpyridin-2(1H)-one (Step A6.1) at 90° C. for 1 hr. Rt=1.02 min (UPLC-MS); ESI-MS=276.0 [M+1]$^+$ (UPLC-MS).

Intermediate A7: 1-(sec-butyl)-5-(4,4,5,5-tetramethyl-1,3,2-dioxaborolan-2-yl)pyridin-2(1H)-one

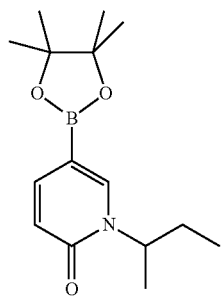 [SMILES: CCC(C)n1cc(B2OC(C)(C)C(C)(C)O2)ccc1=O]

Step A7.1: 5-bromo-1-(sec-butyl)pyridin-2(1H)-one

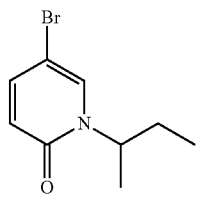

The title compound was prepared in analogy to the procedure described in Step A1.1 (method A) using 5-bromopyridin-2(1H)-one and 2-bromobutane. Rt=0.81 min (UPLC-MS); ESI-MS=229.9/231.9 [M+1]$^+$ (UPLC-MS).

1-(sec-butyl)-5-(4,4,5,5-tetramethyl-1,3,2-dioxaborolan-2-yl)pyridin-2(1H)-one

The title compound was prepared in analogy to the procedure described in Intermediate A1 (method A) using 5-bromo-1-(sec-butyl)pyridin-2(1H)-one (Step A7.1) at 90° C. for 1 hr. Rt=1.04 min (UPLC-MS); ESI-MS=278.1 [M+1]$^+$ (UPLC-MS).

Intermediate A8: 1-cyclopentyl-5-(4,4,5,5-tetramethyl-1,3,2-dioxaborolan-2-yl)pyridin-2(1H)-one

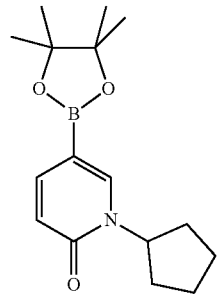 [SMILES: CC1(C)OB(c2ccc(=O)n(C3CCCC3)c2)OC1(C)C]

Step A8.1: 5-bromo-1-cyclopentylpyridin-2(1H)-one

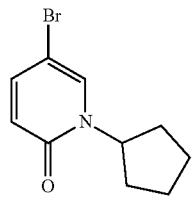 [SMILES: O=c1ccc(Br)cn1C1CCCC1]

The title compound was prepared in analogy to the procedure described in Step A1.1 (method A) using 5-bromopyridin-2(1H)-one and bromocyclopentane. Rt=0.86 min (UPLC-MS); ESI-MS=242.0/244.0 [M+1]$^+$ (UPLC-MS).

1-cyclopentyl-5-(4,4,5,5-tetramethyl-1,3,2-dioxaborolan-2-yl)pyridin-2(1H)-one

The title compound was prepared in analogy to the procedure described in Intermediate A1 (method A) using 5-bromo-1-cyclopentylpyridin-2(1H)-one (Step A8.1). Rt=1.11 min (UPLC-MS); ESI-MS=290.1 [M+1]$^+$ (UPLC-MS).

Intermediate A9: 1-ethyl-5-(4,4,5,5-tetramethyl-1,3,2-dioxaborolan-2-yl)pyridin-2(1H)-one

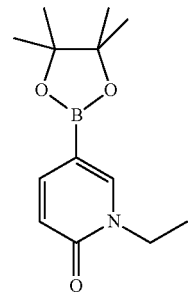 [SMILES: CCn1cc(B2OC(C)(C)C(C)(C)O2)ccc1=O]

Step A9.1: 5-bromo-1-ethylpyridin-2(1H)-one

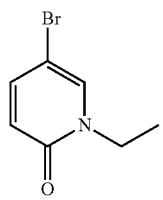

The title compound was prepared in analogy to the procedure described in Step A1.1 (method A) using 5-bromopyridin-2(1H)-one and iodoethane. Rt=0.61 min (UPLC-MS); ESI-MS=202.0/204.0 [M+1]$^+$ (UPLC-MS).

1-ethyl-5-(4,4,5,5-tetramethyl-1,3,2-dioxaborolan-2-yl)pyridin-2(1H)-one

The title compound was prepared in analogy to the procedure described in Intermediate A1 (method A) using 5-bromo-1-ethylpyridin-2(1H)-one (Step A9.1). Rt=0.89 min (UPLC-MS); ESI-MS=250.1 [M+1]$^+$ (UPLC-MS).

Intermediate A10: 1-cyclopropyl-5-(4,4,5,5-tetramethyl-1,3,2-dioxaborolan-2-yl)pyridin-2(1H)-one

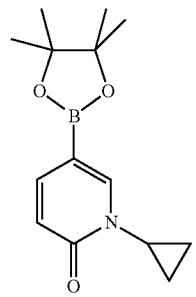 [SMILES: CC1(C)OB(c2ccc(=O)n(C3CC3)c2)OC1(C)C]

Step A10.1: 5-bromo-1-cyclopropylpyridin-2(1H)-one

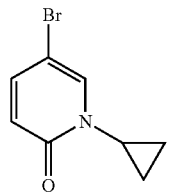 [SMILES: O=c1ccc(Br)cn1C1CC1]

In a MW vial, 5-bromopyridin-2(1H)-one (250 mg, 1.437 mmol) was dissolved in DCE (7 mL). cyclopropylboronic acid (254 mg, 2.96 mmol), Na$_2$CO$_3$ (335 mg, 3.16 mmol), Cu(OAc)$_2$ (271 mg, 1.494 mmol) and 2,2'-bipyridine (236 mg, 1.509 mmol) were added. The MW vial was sealed and the reaction mixture was heated up and stirred at 70° C. overnight. The mixture was quenched with brine, diluted in DCM and both phases were separated. The organic layer was washed with brine, dried over MgSO$_4$, filtered and evaporated under reduced pressure. The crude product was purified by flash column chromatography on silica gel (cyclohexane/0 to 100% EtOAc) to afford the title product (80 mg, 0.366 mmol, 25.5% yield) as a yellow oil. Rt=0.63 min (UPLC-MS); ESI-MS=214.0/216.0 [M+1]$^+$ (UPLC-MS).

1-cyclopropyl-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-cyclopropylpyridin-2(1H)-one (Step A10.1). Rt=0.89 min (UPLC-MS); ESI-MS=262.2 [M+1]$^+$ (UPLC-MS).

Intermediate A11: 1-(cyclobutylmethyl)-5-(4,4,5,5-tetramethyl-1,3,2-dioxaborolan-2-yl)pyridin-2(1H)-one

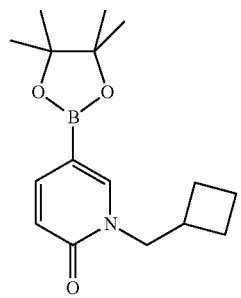 [SMILES: CC1(C)OB(c2ccc(=O)n(CC3CCC3)c2)OC1(C)C]

Step A11.1: 5-bromo-1-(cyclobutylmethyl)pyridin-2(1H)-one

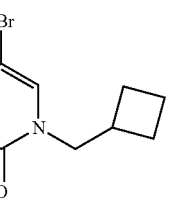

The title compound was prepared in analogy to the procedure described in Step A1.1 (method A) using 5-bromopyridin-2(1H)-one and (bromomethyl)cyclobutane. Rt=0.87 min (UPLC-MS); ESI-MS=241.9/243.9 [M+1]$^+$ (UPLC-MS).

1-(cyclobutylmethyl)-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-(cyclobutylmethyl)pyridin-2(1H)-one (Step A11.1). Rt=1.10 min (UPLC-MS); ESI-MS=290.1 [M+1]$^+$ (UPLC-MS).

Intermediate A12: 5-(4,4,5,5-tetramethyl-1,3,2-dioxaborolan-2-yl)-1-(2,2,2-trifluoroethyl)pyridin-2(1H)-one

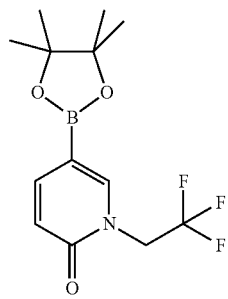 [SMILES: CC1(C)OB(c2ccc(=O)n(CC(F)(F)F)c2)OC1(C)C]

The title compound was prepared in analogy to the procedure described in Intermediate A1 (method A) using 5-bromo-1-(2,2,2-trifluoroethyl)pyridin-2(1H)-one. Rt=1.01 min (UPLC-MS); ESI-MS=304.1 [M+1]$^+$ (UPLC-MS).

Intermediate A13: 1-(2-ethylbutyl)-5-(4,4,5,5-tetramethyl-1,3,2-dioxaborolan-2-yl)pyridin-2(1H)-one

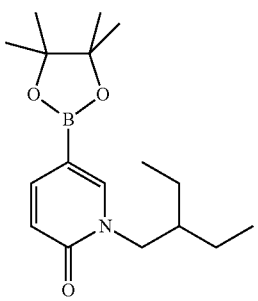 [SMILES: CCC(CC)Cn1cc(B2OC(C)(C)C(C)(C)O2)ccc1=O]

Step A13.1: 5-bromo-1-(2-ethylbutyl)pyridin-2(1H)-one

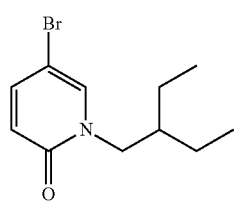

The title compound was prepared in analogy to the procedure described in Step A1.1 (method A) using 5-bromopyridin-2(1H)-one and 3-(bromomethyl)pentane. Rt=1.01 min (UPLC-MS); ESI-MS=257.9/260.0 [M+1]$^+$ (UPLC-MS).

1-(2-ethylbutyl)-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-(2-ethylbutyl)pyridin-2(1H)-one (Step A13.1). Rt=1.23 min (UPLC-MS); ESI-MS=306.1 [M+1]$^+$ (UPLC-MS).

Intermediate A14: 1-isobutyl-5-(4,4,5,5-tetramethyl-1,3,2-dioxaborolan-2-yl)pyridin-2(1H)-one

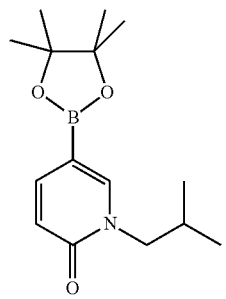 [SMILES: CC(C)Cn1cc(B2OC(C)(C)C(C)(C)O2)ccc1=O]

Step A14.1: 5-bromo-1-isobutylpyridin-2(1H)-one

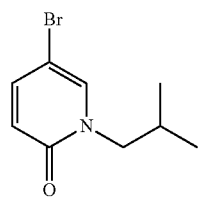

The title compound was prepared in analogy to the procedure described in Step A1.1 (method A) using 5-bromopyridin-2(1H)-one and 1-bromo-2-methylpropane. Rt=0.82 min (UPLC-MS); ESI-MS=229.9/231.9 [M+1]$^+$ (UPLC-MS).

1-isobutyl-5-(4,4,5,5-tetramethyl-1,3,2-dioxaborolan-2-yl)pyridin-2(1H)-one

The title compound was prepared in analogy to the procedure described in Intermediate A1 (method A) using 5-bromo-1-isobutylpyridin-2(1H)-one (Step A14.1). Rt=1.08 min (UPLC-MS); ESI-MS=278.1 [M+1]$^+$ (UPLC-MS).

Intermediate A15: 1-(methoxymethyl)-5-(4,4,5,5-tetramethyl-1,3,2-dioxaborolan-2-yl)pyridin-2(1H)-one

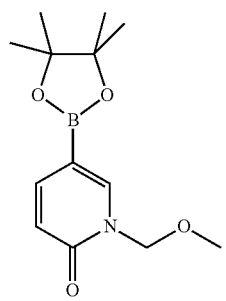

Step A15.1: 5-bromo-1-(methoxymethyl)pyridin-2(1H)-one

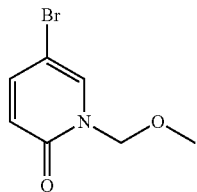

The title compound was prepared in analogy to the procedure described in Step A1.1 (method A) using 5-bromopyridin-2(1H)-one and bromo(methoxy)methane. Rt=0.57 min (UPLC-MS); ESI-MS=217.9/219.9 [M+1]$^+$ (UPLC-MS).

1-(methoxymethyl)-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-(methoxymethyl)pyridin-2(1H)-one (Step A15.1). Rt=0.87 min (UPLC-MS); ESI-MS=266.1 [M+1]$^+$ (UPLC-MS).

Intermediate A16: 5-(4,4,5,5-tetramethyl-1,3,2-dioxaborolan-2-yl)-1-(3,3,3-trifluoropropyl)pyridin-2(1H)-one

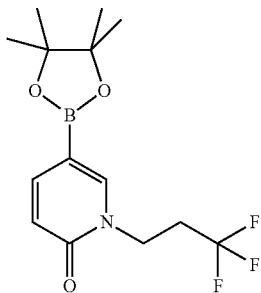 [SMILES: CC1(C)OB(c2ccc(=O)n(CCC(F)(F)F)c2)OC1(C)C]

Step A16.1: 5-bromo-1-(3,3,3-trifluoropropyl)pyridin-2(1H)-one

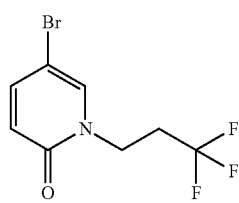 [SMILES: O=c1ccc(Br)cn1CCC(F)(F)F]

The title compound was prepared in analogy to the procedure described in Step A1.1 (method A) using 5-bromopyridin-2(1H)-one and 3-bromo-1,1,1-trifluoropropane. Rt=0.78 min (UPLC-MS); ESI-MS=269.9/271.9 [M+1]$^+$ (UPLC-MS).

5-(4,4,5,5-tetramethyl-1,3,2-dioxaborolan-2-yl)-1-(3,3,3-trifluoropropyl)pyridin-2(1H)-one The title compound was prepared in analogy to the procedure described in Intermediate A1 (method A) using 5-bromo-1-(3,3,3-trifluoropropyl)pyridin-2(1H)-one (Step A16.1). Rt=1.04 min (UPLC-MS); ESI-MS=318.0 [M+1]$^+$ (UPLC-MS).

Intermediate A17: 1-isopentyl-5-(4,4,5,5-tetramethyl-1,3,2-dioxaborolan-2-yl)pyridin-2(1H)-one

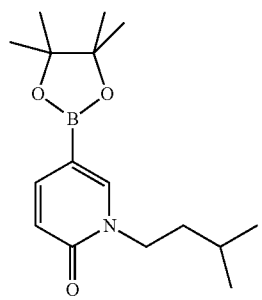 [SMILES: CC(C)CCn1cc(B2OC(C)(C)C(C)(C)O2)ccc1=O]

Step A17.1: 5-bromo-1-isopentylpyridin-2(1H)-one

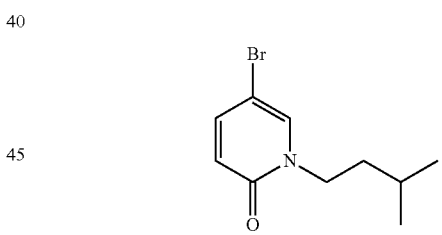

The title compound was prepared in analogy to the procedure described in Step A1.1 (method A) using 5-bromopyridin-2(1H)-one and 1-bromo-3-methylbutane. Rt=0.94 min (UPLC-MS); ESI-MS=244.0/246.0 [M+1]$^+$ (UPLC-MS).

1-isopentyl-5-(4,4,5,5-tetramethyl-1,3,2-dioxaborolan-2-yl)pyridin-2(1H)-one The title compound was prepared in analogy to the procedure described in Intermediate A1 (method A) using 5-bromo-1-isopentylpyridin-2(1H)-one (Step A17.1). Rt=1.17 min (UPLC-MS); ESI-MS=292.1 [M+1]$^+$ (UPLC-MS).

Intermediate A18: 1-(tetrahydro-2H-pyran-2-yl)-5-(4,4,5,5-tetramethyl-1,3,2-dioxaborolan-2-yl)pyridin-2(1H)-one

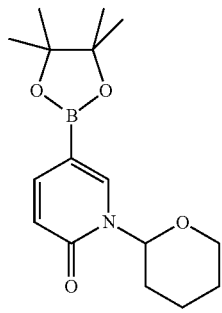 [SMILES: CC1(C)OB(c2ccc(=O)n(C3CCCCO3)c2)OC1(C)C]

The title compound was prepared in analogy to the procedure described in Intermediate A1 (method A) using 5-bromo-1-(tetrahydro-2H-pyran-2-yl)pyridin-2(1H)-one. Rt=1.09 min (UPLC-MS); ESI-MS=306.2 [M+1]$^+$ (UPLC-MS).

Intermediate A19: 1-methyl-5-(4,4,5,5-tetramethyl-1,3,2-dioxaborolan-2-yl)pyridin-2(1H)-one

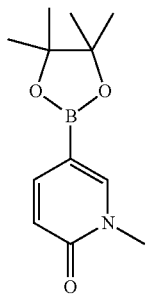

The title compound was prepared in analogy to the procedure described in Intermediate A1 (method A) using 5-bromo-1-methylpyridin-2(1H)-one. Rt=0.80 min (UPLC-MS); ESI-MS=236.1 [M+1]$^+$ (UPLC-MS).

Intermediate 2: 5'-bromo-1-isopropyl-[3,3'-bipyridin]-6(1H)-one

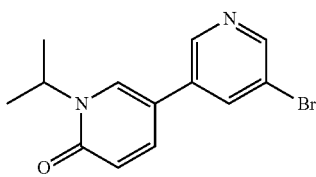 [SMILES: CC(C)n1cc(-c2cncc(Br)c2)ccc1=O]

The title compound was prepared in analogy to the procedure described in Intermediate 1 (method A) using 3,5-dibromopyridine and 1-isopropyl-5-(4,4,5,5-tetramethyl-1,3,2-dioxaborolan-2-yl)pyridin-2(1H)-one (Intermediate A1—method A). The crude material was purified by flash column chromatography on silica gel (Cyclohexane/0 to 100% EtOAc) to afford the title product as a brown solid. Rt=0.81 min (UPLC-MS); ESI-MS=292.9/294.9 [M+1]$^+$ (UPLC-MS).

Intermediate B1: 1-ethyl-5-(4,4,5,5-tetramethyl-1,3,2-dioxaborolan-2-yl)indolin-2-one

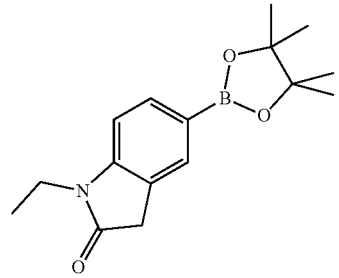 [SMILES: CCN1C(=O)Cc2cc(B3OC(C)(C)C(C)(C)O3)ccc21]

Step B1.1: 5-bromo-1-ethylindoline-2,3-dione

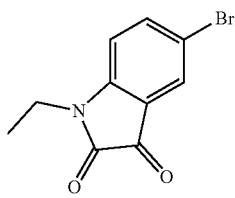

In a 25 mL round-bottomed flask, 5-bromoindoline-2,3-dione (158 mg, 0.699 mmol) was dissolved in DMF (5 mL). K$_2$CO$_3$ (145 mg, 1.049 mmol) and ethyl iodide (0.062 mL, 0.769 mmol) were added. The resulting mixture was heated up and stirred at 60° C. for 1 hr. The reaction was quenched with water, diluted with EtOAc and saturated aqueous NaHCO$_3$ solution and both phases were separated. The aqueous layer was extracted with EtOAc. The combined organic layers were washed with brine, dried over MgSO$_4$, filtered and concentrated under reduced pressure to afford the title product (196 mg, 0.540 mmol, 77% yield) as a brown solid. Rt=0.92 min (UPLC-MS); ESI-MS=253.9/255.9 [M+1]$^+$ (UPLC-MS).

Step B1.2: 5-bromo-1-ethylindolin-2-one

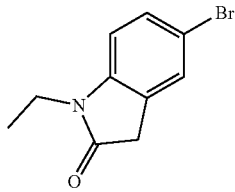

A MW vial was charged with 5-bromo-1-ethylindoline-2,3-dione (Step B1.1) (196 mg, 0.540 mmol) in hydrazine hydrate (1.5 mL). The MW vial was sealed and the resulting mixture was heated up and stirred at 120° C. for 1 hr. The reaction was cooled down to RT, concentrated to dryness and the residue was diluted with EtOAc. The organic layer was washed with 1N HCl and brine, dried over MgSO$_4$, filtered and concentrated under reduced pressure to afford the title product (153 mg, 0.510 mmol, 94% yield). Rt=0.94 min (UPLC-MS); ESI-MS=239.9/241.9 [M+1]$^+$ (UPLC-MS).

1-ethyl-5-(4,4,5,5-tetramethyl-1,3,2-dioxaborolan-2-yl)indolin-2-one

The title compound was prepared in analogy to the procedure described in Intermediate A1 (method A) using 5-bromo-1-ethylindolin-2-one (Step B1.2). Rt=1.11 min (UPLC-MS); ESI-MS=288.1 [M+1]$^+$ (UPLC-MS).

Intermediate B2: 1-isopropyl-5-(4,4,5,5-tetramethyl-1,3,2-dioxaborolan-2-yl)indolin-2-one

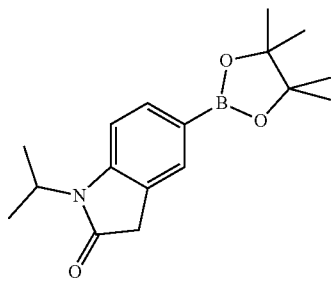 [SMILES: CC(C)N1C(=O)Cc2cc(B3OC(C)(C)C(C)(C)O3)ccc21]

Step B2.1: 5-bromo-1-isopropylindoline-2,3-dione

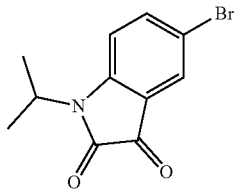

The title compound was prepared in analogy to the procedure described in Step B1.1 using 5-bromoindoline-2,3-dione and 2-iodopropane to afford the title product as a brown solid. Rt=1.00 min (UPLC-MS); ESI-MS=267.9/269.9 [M+1]$^+$ (UPLC-MS).

Step B2.2: 5-bromo-1-isopropylindolin-2-one

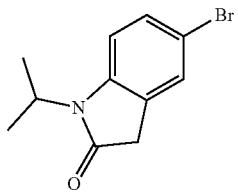

The title compound was prepared in analogy to the procedure described in Step B1.2 using 5-bromo-1-isopropylindoline-2,3-dione (Step B2.1). Rt=1.03 min (UPLC-MS); ESI-MS=253.9/256.0 [M+1]$^+$ (UPLC-MS).

1-isopropyl-5-(4,4,5,5-tetramethyl-1,3,2-dioxaborolan-2-yl)indolin-2-one

The title compound was prepared in analogy to the procedure described in Intermediate A1 (method A) using 5-bromo-1-isopropylindolin-2-one (Step B2.2) to afford the title product as a dark oil. Rt=1.18 min (UPLC-MS); ESI-MS=302.1 [M+1]$^+$ (UPLC-MS).

Intermediate B3: 3-ethyl-1-methyl-5-(4,4,5,5-tetramethyl-1,3,2-dioxaborolan-2-yl)indolin-2-one

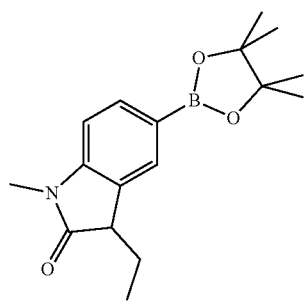

Step B3.1: 5-bromo-3-ethyl-1-methylindolin-2-one

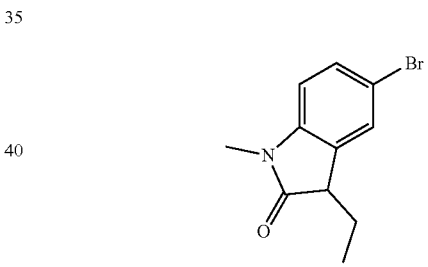

The title compound was prepared in analogy to the procedure described in Step 1.1 using 5-bromo-3-ethylindolin-2-one at 60° C. for 2 hr. The crude material was purified by flash column chromatography on silica gel (Cyclohexane/0 to 40% EtOAc) to afford the title product as a brown solid. Rt=1.04 min (UPLC-MS); ESI-MS=254.1/256.1 [M+1]$^+$ (UPLC-MS).

3-ethyl-1-methyl-5-(4,4,5,5-tetramethyl-1,3,2-dioxaborolan-2-yl)indolin-2-one

The title compound was prepared analogy to the procedure described in Intermediate A3 using 5-bromo-3-ethyl-1-methylindolin-2-one (Step B3.1). The reaction was filtered through a pad of silica gel and the resulting filtrate was evaporated under reduced pressure to afford the title product as a black oil without further purification. Rt=1.19 min (UPLC-MS); ESI-MS=302.3 [M+1]$^+$ (UPLC-MS).

Intermediate B4: 3,3-difluoro-1-methyl-5-(4,4,5,5-tetramethyl-1,3,2-dioxaborolan-2-yl)indolin-2-one

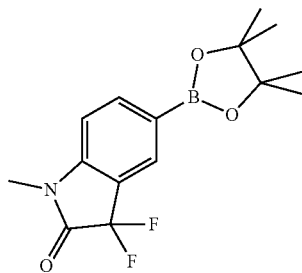

Step B4.1:
5-bromo-3,3-difluoro-1-methylindolin-2-one

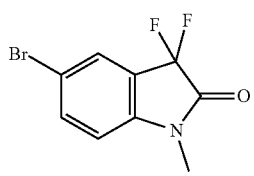

A stirred brown solution of 5-bromo-1-methylindoline-2,3-dione (500 mg, 2.083 mmol) in DCM (10 mL) was cooled down to 0° C. and bis(2-methoxyethyl)aminosulfur trifluoride (1.152 ml, 3.12 mmol) was slowly added into it, followed by EtOH (0.036 mL, 0.625 mmol). The reaction mixture was allowed to warm up and stir overnight at RT. Bis(2-methoxyethyl)aminosulfur trifluoride (1.152 mL, 3.12 mmol) was added and the mixture was stirred 8 hr at RT. The reaction was quenched with saturated aqueous $Na_2CO_3$ solution and both phases were separated. The organic layer was washed with brine, dried over $MgSO_4$, filtered and concentrated under reduced pressure. The crude product was purified by flash column chromatography on silica gel (Cyclohexane/0 to 50% EtOAc). The resulting solid was diluted with MeOH (2 mL), sonicated, cooled down to 0° C. and filtrated off to afford the title product (183 mg, 0.698 mmol) as a beige solid. Rt=1.07 min (UPLC-MS); $^1$H NMR (400 MHz, DMSO-$d_6$) δ ppm 3.17 (s, 3H) 7.22 (d, J=8.44 Hz, 1H) 7.84 (d, J=8.44 Hz, 1H) 8.01 (s, 1H).

3,3-difluoro-1-methyl-5-(4,4,5,5-tetramethyl-1,3,2-dioxaborolan-2-yl)indolin-2-one The title compound was prepared in analogy to the procedure described in Intermediate A3 using 5-bromo-3,3-difluoro-1-methylindolin-2-one (Step B4.1) to afford the title product as a black oil without further purification. Rt=1.22 min (UPLC-MS).

Intermediate B5: 1-isobutyl-5-(4,4,5,5-tetramethyl-1,3,2-dioxaborolan-2-yl)indolin-2-one

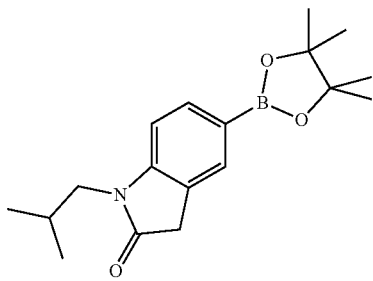 [SMILES: CC(C)CN1C(=O)Cc2cc(B3OC(C)(C)C(C)(C)O3)ccc21]

Step B5.1: 5-bromo-1-isobutylindoline-2,3-dione

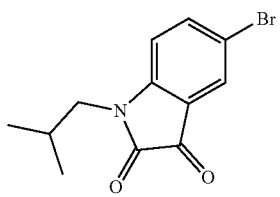

The title compound was prepared in analogy to the procedure described in Step B1.1 using 5-bromoindoline-2,3-dione and 1-iodo-2-methylpropane to afford the title product as a brown solid without further purification. Rt=1.10 min (UPLC-MS); ESI-MS=281.9/283.9 [M+1]$^+$ (UPLC-MS).

Step B5.2: 5-bromo-1-isobutylindolin-2-one

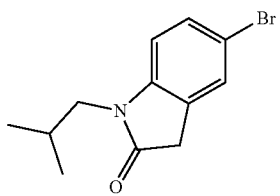

The title compound was prepared in analogy to the procedure described in Step B1.2 using 5-bromo-1-isobutylindoline-2,3-dione (Step B5.1) to afford the title product without further purification. Rt=1.11 min (UPLC-MS); ESI-MS=268.0/270.0 [M+1]$^+$ (UPLC-MS).

1-isobutyl-5-(4,4,5,5-tetramethyl-1,3,2-dioxaborolan-2-yl)indolin-2-one

The title compound was prepared in analogy to the procedure described in Intermediate A1 (method A) using 5-bromo-1-isobutylindolin-2-one (Step B5.2) to afford the title product without further purification. Rt=1.25 min (UPLC-MS); ESI-MS=316.1 [M+1]$^+$ (UPLC-MS).

Intermediate B6: 1-propyl-5-(4,4,5,5-tetramethyl-1,3,2-dioxaborolan-2-yl)indolin-2-one

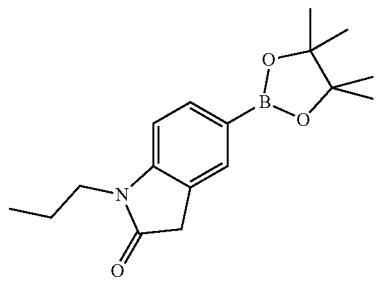 [SMILES: CCCN1C(=O)Cc2cc(B3OC(C)(C)C(C)(C)O3)ccc21]

Step B6.1: 5-bromo-1-propylindoline-2,3-dione

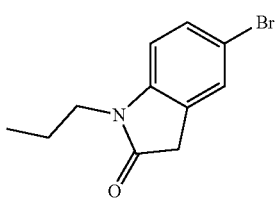

The title compound was prepared in analogy to the procedure described in Step B1.1 using 5-bromoindoline-2,3-dione and 1-iodopropane to afford the title product as a dark solid without further purification. Rt=1.01 min (UPLC-MS); ESI-MS=267.9/269.9 [M+1]+ (UPLC-MS).

Step B6.2: 5-bromo-1-propylindolin-2-one

The title compound was prepared in analogy to the procedure described in Step B1.2 using 5-bromo-1-propylindoline-2,3-dione (Step B6.1) to afford the title product without further purification. Rt=1.03 min (UPLC-MS); ESI-MS=253.9/255.9 [M+1]+ (UPLC-MS).

1-propyl-5-(4,4,5,5-tetramethyl-1,3,2-dioxaborolan-2-yl)indolin-2-one

The title compound was prepared in analogy to the procedure described in Intermediate A1 (method A) using 5-bromo-1-propylindolin-2-one (Step B6.2) to afford the title product without further purification. Rt=1.18 min (UPLC-MS); ESI-MS=302.1 [M+1]+ (UPLC-MS).

Intermediate B7: 1-methyl-6-(4,4,5,5-tetramethyl-1,3,2-dioxaborolan-2-yl)indolin-2-one

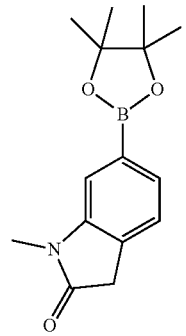

Step B7.1: 6-bromo-1-methylindoline-2,3-dione

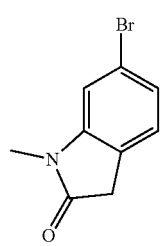

The title compound was prepared in analogy to the procedure described in Step B1.1 using 6-bromoindoline-2,3-dione and methyl iodide to afford the title product as a brown solid without further purification. Rt=0.81 min (UPLC-MS); ESI-MS=239.9/241.9 [M+1]+ (UPLC-MS).

Step B7.2: 6-bromo-1-methylindolin-2-one

The title compound was prepared in analogy to the procedure described in Step B1.2 using 6-bromo-1-methylindoline-2,3-dione (Step B7.1) to afford the title product without further purification. Rt=0.85 min (UPLC-MS); ESI-MS=225.9/227.9 [M+1]+ (UPLC-MS).

1-methyl-6-(4,4,5,5-tetramethyl-1,3,2-dioxaborolan-2-yl)indolin-2-one

The title compound was prepared in analogy to the procedure described in Intermediate A1 (method A) using 6-bromo-1-methylindolin-2-one (Step B7.2) to afford the title product without further purification. Rt=1.02 min (UPLC-MS); ESI-MS=274.1 [M+1]+ (UPLC-MS).

Intermediate B8: 1-(2-methoxyethyl)-5-(4,4,5,5-tetramethyl-1,3,2-dioxaborolan-2-yl)-1H-pyrrolo[2,3-b]pyridin-2(3H)-one

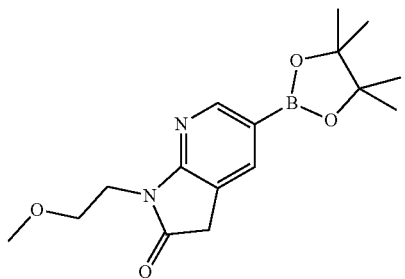

The title compound was prepared in analogy to the procedure described in Intermediate A1 (method A) using 5-bromo-1-(2-methoxyethyl)-1H-pyrrolo[2,3-b]pyridin-2 (3H)-one to afford the title product without further purification. Rt=0.97 min (UPLC-MS); ESI-MS=319.1 [M+1]+ (UPLC-MS).

Intermediate B9: 1-methyl-6-(4,4,5,5-tetramethyl-1,3,2-dioxaborolan-2-yl)-3,4-dihydroquinolin-2(1H)-one

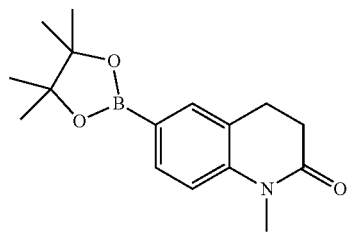 [SMILES: CN1C(=O)CCc2cc(B3OC(C)(C)C(C)(C)O3)ccc21]

Step B9.1:
6-bromo-1-methyl-3,4-dihydroquinolin-2(1H)-one

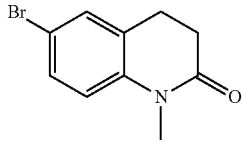

The title compound was prepared in analogy to the procedure described in Step 1.1 (intermediate 1—method A) using 6-bromo-3,4-dihydroquinolin-2(1H)-one at 60° C. for 1 hr. Rt=0.92 min (UPLC-MS); ESI-MS=239.9/241.9 [M+1]+ (UPLC-MS).

1-methyl-6-(4,4,5,5-tetramethyl-1,3,2-dioxaborolan-2-yl)-3,4-dihydroquinolin-2(1H)-one The title compound was prepared in analogy to the procedure described in Intermediate A1 (method A) using 6-bromo-1-methyl-3,4-dihydroquinolin-2(1H)-one (Step B9.1) at 90° C. for 2 hr. Rt=1.10 min (UPLC-MS); ESI-MS=288.1 [M+1]+ (UPLC-MS).

Intermediate B10: 1-(2-methoxyethyl)-5-(4,4,5,5-tetramethyl-1,3,2-dioxaborolan-2-yl)indolin-2-one

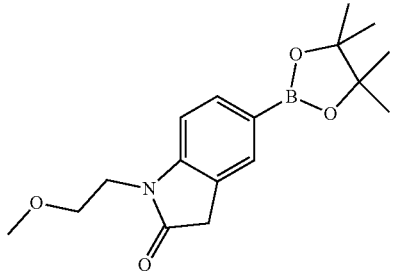

Step B10.1:
5-bromo-1-(2-methoxyethyl)indoline-2,3-dione

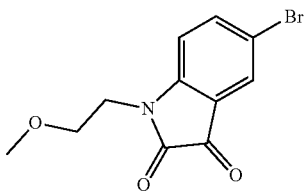 [SMILES: COCCN1C(=O)C(=O)c2cc(Br)ccc21]

The title compound was prepared in analogy to the procedure described in Step B1.1 using 5-bromoindoline-2,3-dione and 1-iodo-2-methoxyethane to afford the title product as an orange oil without any further purification. Rt=0.89 min (UPLC-MS); ESI-MS=283.9/285.9 [M+1]+ (UPLC-MS).

Step B10.2:
5-bromo-1-(2-methoxyethyl)indolin-2-one

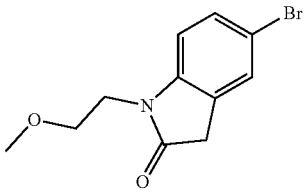

The title compound was prepared in analogy to the procedure described in Step B1.2 using 5-bromo-1-(2-methoxyethyl)indoline-2,3-dione (Step B10.1). The crude material was purified by flash column chromatography on silica gel (DCM/0 to 20% MeOH) to afford the title product as a yellow solid. Rt=0.88 min (UPLC-MS); ESI-MS=269.9/271.9 [M+1]+ (UPLC-MS).

1-(2-methoxyethyl)-5-(4,4,5,5-tetramethyl-1,3,2-dioxaborolan-2-yl)indolin-2-one

The title compound was prepared in analogy to the procedure described in Intermediate A1 (method A) using 5-bromo-1-(2-methoxyethyl)indolin-2-one (Step B10.2) to afford the title product without further purification. Rt=1.05 min (UPLC-MS); ESI-MS=317.1 [M+1]⁺ (UPLC-MS).

Intermediate B111: 1-(3-methoxypropyl)-5-(4,4,5,5-tetramethyl-1,3,2-dioxaborolan-2-yl)indolin-2-one

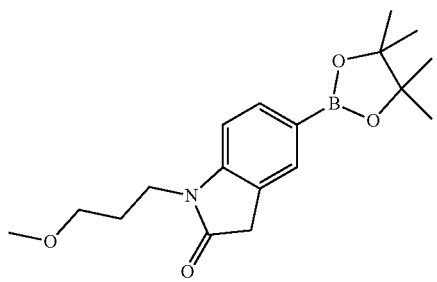

Step B11.1:
5-bromo-1-(3-propoxyethyl)indoline-2,3-dione

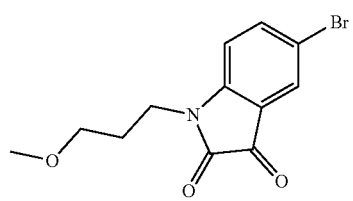 [SMILES: COCCCN1C(=O)C(=O)c2cc(Br)ccc21]

The title compound was prepared in analogy to the procedure described in Step B1.1 using 5-bromoindoline-2,3-dione and 1-bromo-3-methoxypropane to afford the title product as reddish solid after flash column chromatography on silica gel (cyclohexane/EtOAc from 0 to 70% EtOAc). Rt=0.94 min (UPLC-MS); ESI-MS=299.9 [M+1]⁺ (UPLC-MS).

Step B11.2:
5-bromo-1-(3-methoxypropyl)indolin-2-one

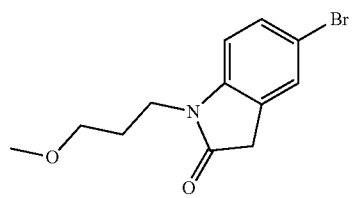 [SMILES: COCCCN1C(=O)Cc2cc(Br)ccc21]

The title compound was prepared in analogy to the procedure described in Step B1.2 using 5-bromo-1-(3-methoxypropyl)indoline-2,3-dione (Step B11.1). The crude material was purified by flash column chromatography on silica gel (cyclohexane/0 to 60% EtOAc) to afford the title product as a yellow solid. Rt=0.98 min (UPLC-MS); ESI-MS=286.0 [M+1]⁺ (UPLC-MS).

1-(3-methoxypropyl)-5-(4,4,5,5-tetramethyl-1,3,2-dioxaborolan-2-yl)indolin-2-one The title compound was prepared in analogy to the procedure described in Intermediate A1 (method A) using 5-bromo-1-(3-methoxypropyl)indolin-2-one (Step B11.2) to afford the title product without further purification. Rt=1.13 min (UPLC-MS); ESI-MS=332.1 [M+1]⁺ (UPLC-MS).

Intermediate B12: 6-fluoro-1-methyl-5-(4,4,5,5-tetramethyl-1,3,2-dioxaborolan-2-yl)indolin-2-one

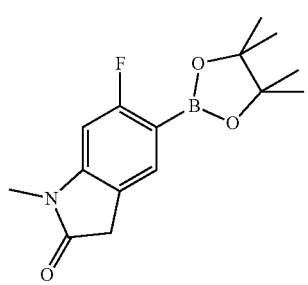

Step B12.1: 6-fluoro-1-methylindoline-2,3-dione

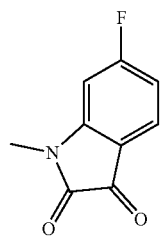

The title compound was prepared in analogy to the procedure described in Step 1.1 (intermediate 1—method A) using 6-fluoroindoline-2,3-dione. 5 ml of DMF were added to the reaction mixture in order to improve 6-fluoroindoline-2,3-dione solubility. The title product was obtained as a yellow solid without further purification. Rt=0.66 min (UPLC-MS); ESI-MS=180.0 [M+1]⁺/197.0 [M+18]⁺ (UPLC-MS).

Step B12.2: 6-fluoro-1-methylindolin-2-one

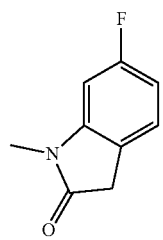

The title compound was prepared in in analogy to the procedure described in Step B1.2 using 6-fluoro-1-methyl-indoline-2,3-dione (Step B12.1) to afford the title product without further purification. Rt=0.72 min (UPLC-MS); ESI-MS=166.0 [M+1]⁺ (UPLC-MS).

Step B12.3:
5-bromo-6-fluoro-1-methylindolin-2-one

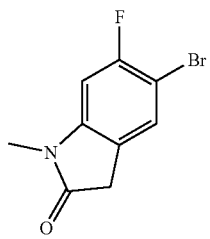

A solution of 6-fluoro-1-methylindolin-2-one (Step B12.2) (255 mg, 1.235 mmol) in DMF (10 mL) was cooled down to 0° C. and NBS (286 mg, 1.606 mmol) was added. The resulting mixture was allowed to warm up to RT then, heated up and stirred at 80° C. for 2 hr. The reaction mixture was diluted with EtOAc and washed with aqueous NaHCO$_3$ solution, 0.1M LiBr and brine. The organic layer was dried over MgSO$_4$, filtered and concentrated under reduced pressure. The crude material was purified by flash chromatography on silica gel (cyclohexane/20 to 100% EtOAc) to afford the title product (222 mg, 0.591 mmol, 47.9% yield). Rt=0.87 min (UPLC-MS); ESI-MS=243.9/245.9 [M+1]$^+$ (UPLC-MS).

6-fluoro-1-methyl-5-(4,4,5,5-tetramethyl-1,3,2-dioxaborolan-2-yl)indolin-2-one

The title compound was prepared in analogy to the procedure described in Intermediate A3 using 5-bromo-6-fluoro-1-methylindolin-2-one (Step B12.3) to afford the title product without further purification. Rt=1.02 min (UPLC-MS); ESI-MS=292.0 [M+1]$^+$ (UPLC-MS).

Intermediate B13: 3,3-dimethyl-6-(4,4,5,5-tetramethyl-1,3,2-dioxaborolan-2-yl)indolin-2-one

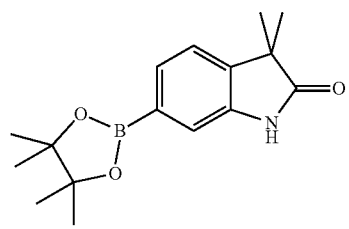 [SMILES: CC1(C)C(=O)Nc2cc(B3OC(C)(C)C(C)(C)O3)ccc21]

Step B13.1: N'-(3-bromophenyl)isobutyrohydrazide

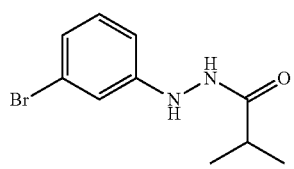

To the stirred mixture of 3-bromophenylhydrazine hydrochloride (6.10 g, 27.3 mmol) in DCM (60 mL) was added TEA (7.69 mL, 54.6 mmol) and the reaction mixture was cooled to 0° C. Isobutyric anhydride (4.90 mL, 28.7 mmol) was added dropwise at 0-5° C. during 10 min. The resulting mixture was allowed to warm up and stir at RT for 16 hr. The reaction mixture was concentrated under reduced pressure. The residue was extracted between EtOAc (2×100 mL) and water (2×100 mL). The organic layers were washed with brine (50 mL), dried over Na$_2$SO$_4$, filtered and concentrated under reduced pressure. The residue was crystallized several times from Et$_2$O to afford the title product (6.20 g, 23.87 mmol, 87% yield) as slightly yellow solid. Rt=0.85 min (UPLC-MS); ESI-MS=257.0/259.0 [M+1]$^+$ (UPLC-MS); ESI-MS=254.9/256.9 [M+1]$^-$ (UPLC-MS).

Step B13.2: 6-bromo-3,3-dimethylindolin-2-one

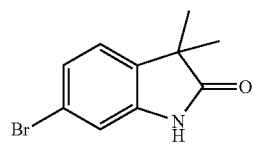

The stirred mixture of N'-(3-bromophenyl)isobutyrohydrazide (Step B13.1) (6.20 g, 23.87 mmol) and CaH$_2$ (1.51 g, 35.8 mmol) was heated up and stirred 25 min at 180° C. then, 15 min at 210° C. and finally 30 min at 230° C. The reaction mixture was cooled to RT and stopped. To the solid reaction mixture was added dropwise MeOH/water 1:1 (40 mL) (gas evolution). After gas evolution had ceased, concentrated HCl was added until pH 1. Water (20 mL) was added and the mixture was heated up and stirred 1 hr at 100° C. The mixture was cooled down to 0° C. and adjusted to pH 3 with 5N NaOH. The mixture was extracted with EtOAc (2×60 mL). The combined organic layers were washed with water (60 mL) and brine (60 mL), dried over Na$_2$SO$_4$, filtered and concentrated under reduced pressure. The crude product was purified by flash column chromatography on silica gel (EtOAc/Heptane 1:9 to 1:0) to afford the title product (1.22 g, 5.03 mmol, 21.1% yield) as white solid. Rt=0.93 min (UPLC-MS); ESI-MS=239.8/242.0 [M+1]$^+$ (UPLC-MS); ESI-MS=237.9/239.9 [M+1]$^-$ (UPLC-MS); TLC (EtOAc/Heptane 1:2) Rf=0.25.

3,3-dimethyl-6-(4,4,5,5-tetramethyl-1,3,2-dioxaborolan-2-yl)indolin-2-one

The title compound was prepared in analogy to the procedure described in Intermediate A1 (method A) using 6-bromo-3,3-dimethylindolin-2-one (Step B13.2). Rt=1.03 min (UPLC-MS); ESI-MS=288.0 [M+1]$^+$ (UPLC-MS).

Intermediate B14: 3-methyl-6-(4,4,5,5-tetramethyl-1,3,2-dioxaborolan-2-yl)indolin-2-one

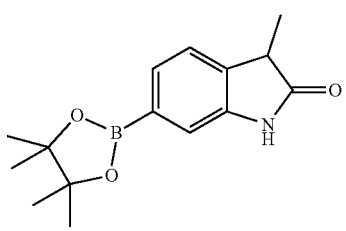 [SMILES: CC1C(=O)Nc2cc(B3OC(C)(C)C(C)(C)O3)ccc21]

Step B14.1: dimethyl 2-(4-bromo-2-nitrophenyl)malonate

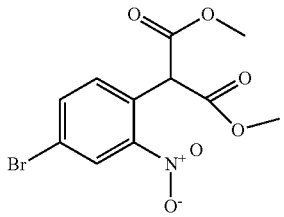

To a stirred solution of dimethyl malonate (0.783 mL, 6.82 mmol) in DMF (15 mL) were added $K_2CO_3$ (1.885 g, 13.64 mmol) followed by 4-bromo-1-fluoro-2-nitrobenzene (1 g, 4.55 mmol). The reaction mixture was stirred at RT for 2 hr. The mixture was poured onto a mixture of ice/2N HCl and stirred until precipitation occurred. The resulting solid was filtered off to afford the title product (1.50 g, 4.29 mmol, 94% yield) as white solid. Rt=1.02 min (UPLC-MS); ESI-MS=331.8/333.9 [M+1]+ (UPLC-MS); ESI-MS=329.9/332.0 [M−1]− (UPLC-MS).

Step B14.2: dimethyl 2-(4-bromo-2-nitrophenyl)-2-methylmalonate

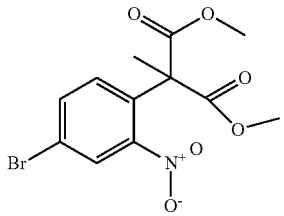

To a stirred solution of dimethyl 2-(4-bromo-2-nitrophenyl)malonate (Step B14.1) (1.50 g, 4.52 mmol) in DMF (20 mL) cooled down to 0° C. were added $K_2CO_3$ (0.687 g, 4.97 mmol) followed by methyl iodide (0.325 mL, 5.19 mmol). The reaction mixture was allowed to warm up and stir at RT for 2 hr. The mixture was diluted with EtOAc and brine and both phases were separated. The organic layer was washed once again with brine, dried over $MgSO_4$, filtered and concentrated under reduced pressure to afford the title product (1.85 g, 4.01 mmol, 89% yield) as a yellow oil. Rt=1.04 min (UPLC-MS); ESI-MS=346.0/347.9 [M+1]+ (UPLC-MS).

Step B14.3: methyl 6-bromo-3-methyl-2-oxoindoline-3-carboxylate

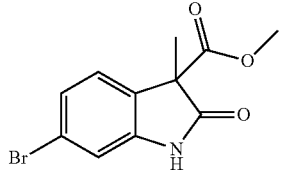 [SMILES: COC(=O)C1(C)C(=O)Nc2cc(Br)ccc21]

Dimethyl 2-(4-bromo-2-nitrophenyl)-2-methylmalonate (Step B14.2) (1.85 g, 4.01 mmol) was dissolved in AcOH (10 mL). Iron (0.672 g, 12.03 mmol) was added and the reaction mixture was heated up and stirred at 100° C. for 2 hr. The mixture was diluted with DCM and brine and both phases were separated. The organic layer was washed once again with brine, dried over $MgSO_4$, filtered and concentrated under reduced pressure to afford the title product (1.53 g, 4.15 mmol, quantitative yield) as beige solid. Rt=0.88 min (UPLC-MS); ESI-MS=283.9/285.9 [M+1]+ (UPLC-MS); ESI-MS=281.9/283.9 [M−1]− (UPLC-MS).

Step B14.4: 6-bromo-3-methylindolin-2-one

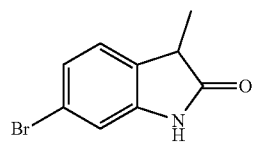

Methyl 6-bromo-3-methyl-2-oxoindoline-3-carboxylate (Step B14.3) (1.54 g, 4.17 mmol) was dissolved in TFA (3.7 mL, 48.0 mmol). $H_2SO_4$ (0.370 mL, 6.59 mmol) was added and the reaction mixture was heated up and stirred at 80° C. for 3 hr. The mixture was diluted with ice/water and stirred at 0° C. for 1 hr. A precipitate occurred. The resulting solid was filtered off and dried under reduced pressure to afford the title product (961 mg, 4.04 mmol, 97% yield) as brown clear solid. Rt=0.83 min (UPLC-MS); ESI-MS=225.9/227.9 [M+1]+ (UPLC-MS); ESI-MS=224.1/225.9 [M−1]− (UPLC-MS).

3-methyl-6-(4,4,5,5-tetramethyl-1,3,2-dioxaborolan-2-yl)indolin-2-one

The title compound was prepared in analogy to the procedure described in Intermediate A1 (method A) using 6-bromo-3-methylindolin-2-one (Step B14.4). Rt=0.99 min (UPLC-MS); ESI-MS=274.1 [M+1]+ (UPLC-MS).

Intermediate 3: (1'-isopropyl-6'-oxo-1',6'-dihydro-[3,3'-bipyridin]-5-yl)boronic acid

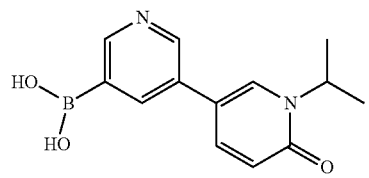

The title compound was prepared in analogy to the procedure described in Intermediate A1 (method A) using 5'-bromo-1-isopropyl-[3,3'-bipyridin]-6(1H)-one Intermediate 2 to afford the title product as a dark solid without any further purification. Rt=0.42 min (UPLC-MS); ESI-MS=259.0 [M+1]+ (UPLC-MS).

Intermediate B15: 5-bromo-1,7-dimethylindolin-2-one

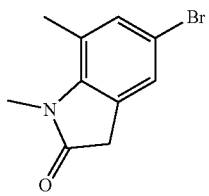

The title compound was prepared in analogy to the procedure described in Step B1.2 using 5-bromo-1,7-dimethylindoline-2,3-dione. The crude material was purified by flash column chromatography on silica gel (DCM/0 to 20% MeOH) to afford the title product as a white solid. Rt=0.93 min (UPLC-MS); ESI-MS=239.9/241.9 [M+1]+ (UPLC-MS); 1H NMR (400 MHz, DMSO-$d_6$) δ ppm 2.53 (s, 3H) 3.38 (s, 3H) 3.55 (s, 2H) 7.26 (d, J=6.72 Hz, 2H).

Intermediate B16: 5-bromo-7-fluoro-1-methylindolin-2-one

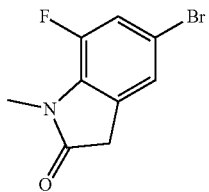

Step B16.1: 7-fluoro-1-methylindoline-2,3-dione

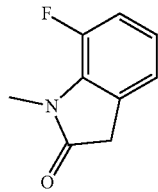

To a stirred solution of 7-fluoroindoline-2,3-dione (500 mg, 3.03 mmol) in DMF (5 mL) were successively added $K_2CO_3$ (502 mg, 3.63 mmol) and methyl iodide (0.199 mL, 3.18 mmol). The resulting mixture was stirred at RT for 1 hr. The mixture was quenched with water, diluted with EtOAc and saturated aqueous $NaHCO_3$ solution and both phases were separated. The aqueous layer was extracted with EtOAc. The combined organic layers were washed with brine, dried over anhydrous $MgSO_4$, filtered and concentrated under reduced pressure to afford the title product (497 mg, 2.219 mmol, 73.3% yield) as yellow solid. Rt=0.69 min (UPLC-MS); ESI-MS=179.9 [M+1]+ (UPLC-MS).

Step B16.2: 5-bromo-7-fluoro-1-methylindoline-2,3-dione

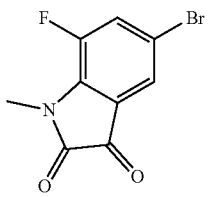

The title compound was prepared in analogy to the procedure described in Step B12.3 using 7-fluoro-1-methylindoline-2,3-dione (Step B16.1) at 80° C. overnight. Rt=0.89 min (UPLC-MS); ESI-MS=257.9/260.0 [M+1]+ (UPLC-MS).

5-bromo-7-fluoro-1-methylindolin-2-one

The title compound was prepared in analogy to the procedure described in Step B1.2 using 5-bromo-7-fluoro-1-methylindoline-2,3-dione (Step B16.2). The crude material was purified by flash column chromatography on silica gel (DCM/0 to 20% MeOH) to afford the title product as a yellow solid. Rt=0.92 min (UPLC-MS); ESI-MS=243.9/245.9 [M+1]+ (UPLC-MS); $^1$H NMR (400 MHz, DMSO-$d_6$) δ ppm 3.27 (d, J=2.81 Hz, 3H) 3.66 (s, 2H) 7.33 (d, J=1.47 Hz, 1H) 7.50 (dd, J=11.25, 1.59 Hz, 1H).

Intermediate B17: 6-bromo-1-methyl-3,4-dihydro-1,8-naphthyridin-2(1H)-one

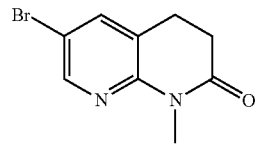

The title compound was prepared in analogy to the procedure described in Step B16.1 using 6-bromo-3,4-dihydro-1,8-naphthyridin-2(1H)-one at RT overnight to afford the title product as a yellow oil without any further purification. Rt=0.84 min (UPLC-MS); ESI-MS=240.9/242.9 [M+1]+ (UPLC-MS).

Intermediate B18: 5-bromo-1-(cyclobutylmethyl)indolin-2-one, (Z)-5-bromo-1-(cyclobutylmethyl)-3-hydrazonoindolin-2-one

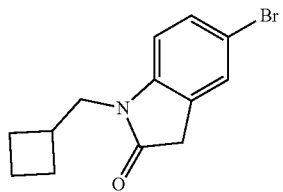 [SMILES: O=C1Cc2cc(Br)ccc2N1CC1CCC1]

Step B18.1:
5-bromo-1-(cyclobutylmethyl)indoline-2,3-dione

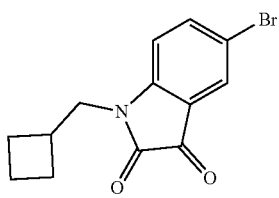 [SMILES: O=C1C(=O)N(CC2CCC2)c2ccc(Br)cc21]

The title compound was prepared in analogy to the procedure described in Step B1.1 using 5-bromoindoline-2,3-dione and (bromomethyl)cyclobutane. Rt=1.15 min (UPLC-MS); ESI-MS=294.0/296.1 [M+1]⁺ (UPLC-MS).

5-bromo-1-(cyclobutylmethyl)indolin-2-one, (Z)-5-bromo-1-(cyclobutylmethyl)-3-hydrazonoindolin-2-one The title compound was prepared in analogy to the procedure described in Step B1.2 using 5-bromo-1-(cyclobutylmethyl)indoline-2,3-dione (Step B18.1). Rt=1.17 min (UPLC-MS); ESI-MS=279.9/281.9 [M+1]⁺ (UPLC-MS); ESI-MS=278.0/279.9 [M−1]⁻ (UPLC-MS).

Intermediate B19: 7-bromo-1-methyl-4,5-dihydro-1H-benzo[b]azepin-2(3H)-one

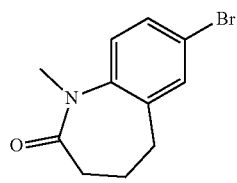

To a stirred solution of 7-bromo-4,5-dihydro-1H-benzo[b]azepin-2(3H)-one (200 mg, 0.833 mmol) in DMF (7 mL) cooled down to 0° C. was added NaH 60% in mineral oil (50.0 mg, 1.249 mmol). The resulting mixture was stirred at RT for 30 min. Methyl iodide (0.078 mL, 1.249 mmol) was added and the resulting mixture was stirred at RT for 1 hr. The mixture was quenched with water, diluted with EtOAc and saturated aqueous NaHCO₃ solution and both phases were separated. The aqueous layer was extracted with EtOAc. The combined organic layers were washed with brine, dried over anhydrous MgSO₄, filtered and concentrated under reduced pressure to afford the title product (304 mg, 0.837 mmol, quantitative yield) as yellow oil. Rt=0.94 min (UPLC-MS); ESI-MS=253.9/255.9 [M+1]⁺ (UPLC-MS).

Intermediate B20: 5-bromo-1-(2-ethylbutyl)indolin-2-one, (Z)-5-bromo-1-(2-ethylbutyl)-3-hydrazonoindolin-2-one

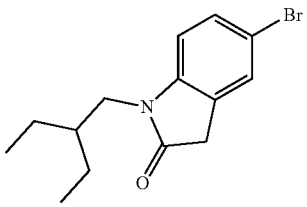 [SMILES: CCC(CC)CN1C(=O)Cc2cc(Br)ccc21]

Step B20.1:
5-bromo-1-(2-ethylbutyl)indoline-2,3-dione

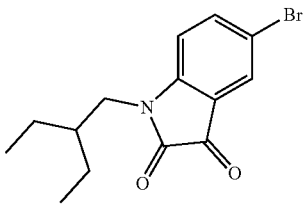 [SMILES: CCC(CC)CN1C(=O)C(=O)c2cc(Br)ccc21]

The title compound was prepared in analogy to the procedure described in Step B1.1 using 5-bromoindoline-2,3-dione and 3-(bromomethyl)pentane. Rt=1.27 min (UPLC-MS); ESI-MS=310.1/312.1 [M+1]⁺ (UPLC-MS).

5-bromo-1-(2-ethylbutyl)indolin-2-one, (Z)-5-bromo-1-(2-ethylbutyl)-3-hydrazonoindolin-2-one The title compound was prepared in analogy to the procedure described in Step B1.2 using 5-bromo-1-(2-ethylbutyl)indoline-2,3-dione (Step B20.1). Rt=1.28 min (UPLC-MS); ESI-MS=295.9/297.9 [M+1]⁺ (UPLC-MS).

Intermediate B21: 1-methyl-5-(4,4,5,5-tetramethyl-1,3,2-dioxaborolan-2-yl)-1,3-dihydrobenzo[c]isothiazole 2,2-dioxide

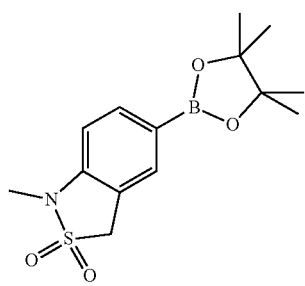

Step B21.1: 5-bromo-1-methyl-1,3-dihydrobenzo[c] isothiazole 2,2-dioxide

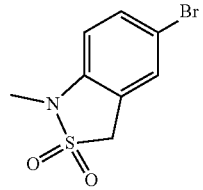

The title compound was prepared in analogy to the procedure described in Step B1.1 using 5-bromo-1,3-dihydrobenzo[c]isothiazole 2,2-dioxide and methyl iodide at RT for 3 hrs. Rt=0.88 min (UPLC-MS).

1-methyl-5-(4,4,5,5-tetramethyl-1,3,2-dioxaborolan-2-yl)-1,3-dihydrobenzo[c]isothiazole 2,2-dioxide The title compound was prepared in analogy to the procedure described in Intermediate A1 (method A) using 5-bromo-1-methyl-1,3-dihydrobenzo[c]isothiazole 2,2-dioxide (Step B21.1) at 90° C. for 2 hr. Rt=1.11 min (UPLC-MS).

Intermediate C1: 5-bromo-1-ethyl-1,3-dihydrobenzo[c]isothiazole 2,2-dioxide

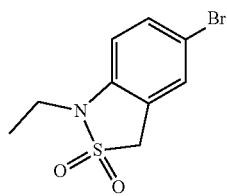

The title compound was prepared in analogy to the procedure described in Step B1.1 using 5-bromo-1,3-dihydrobenzo[c]isothiazole 2,2-dioxide and ethyl iodide at RT for 3 hr. Rt=1.00 min (UPLC-MS).

Intermediate C2: 5-bromo-1-isobutyl-1,3-dihydrobenzo[c]isothiazole 2,2-dioxide

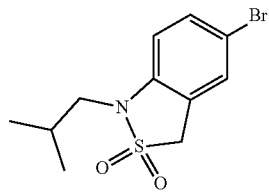 [SMILES: CC(C)CN1c2ccc(Br)cc2CS1(=O)=O]

The title compound was prepared in analogy to the procedure described in Step B1.1 using 5-bromo-1,3-dihydrobenzo[c]isothiazole 2,2-dioxide and 1-iodo-2-methylpropane at RT for 3 hr. Rt=1.17 min (UPLC-MS)

Intermediate C3: 5-bromo-1-(cyclobutylmethyl)-1,3-dihydrobenzo[c]isothiazole 2,2-dioxide

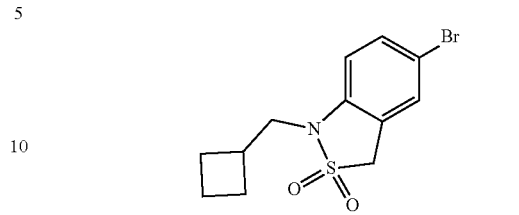

The title compound was prepared in analogy to the procedure described in Step B1.1 using 5-bromo-1,3-dihydrobenzo[c]isothiazole 2,2-dioxide and (bromomethyl)cyclobutane at RT for 3 hr. Rt=1.21 min (UPLC-MS).

Example 1: 5-(1'-isopropyl-6'-oxo-1',6'-dihydro-[3,3'-bipyridin]-5-yl)-1-methylindolin-2-one

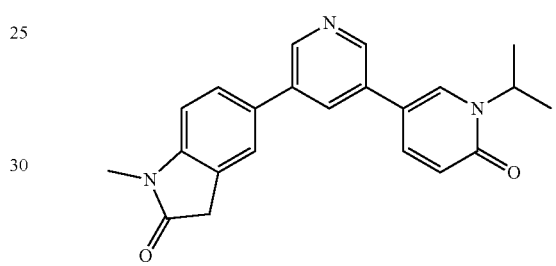

Method A

TO a stirred solution of 5-(5-bromopyridin-3-yl)-1-methylindolin-2-one (Intermediate 1—method A) (3.8 g, 12.53 mmol) in Dioxane (50 mL) were added 1-isopropyl-5-(4,4,5,5-tetramethyl-1,3,2-dioxaborolan-2-yl)pyridin-2(1H)-one (Intermediate A1—method A) (7.26 g, 13.79 mmol), PdCl$_2$ (dppf) (917 mg, 1.253 mmol) and 2M K$_2$CO$_3$ (12.53 ml, 25.07 mmol). The mixture was heated up and stirred at 80° C. for 2 hr. The reaction mixture was filtered through a pad of Celite and washed with EtOAc. The resulting filtrate was diluted with saturated aqueous NaHCO$_3$ solution and EtOAc and both phases were separated. The aqueous layer was extracted with EtOAc, the combined organic layers were washed with brine, dried over anhydrous MgSO$_4$, filtered and concentrated under reduced pressure. Palladium was removed from the residue 500 mg-Thiol cartridges. The crude product was purified by flash column chromatography on silica gel (DCM/0 to 20% MeOH). The resulting brown oil was triturated in MeOH, sonicated, filtrated off and dried under reduced pressure to afford a white solid. Unpure fractions were combined and concentrated, the resulting beige solid was purified by flash chromatography on silica gel (DCM/MeOH 0 to 20% MeOH). Pure fractions were combined and concentrated, precipitated in MeOH, filtrated off and dried under HV to afford a white solid. Pure solids were mixed to afford the title product (1.51 g, 4.20 mmol, 33% yield) as a white solid. Rt=0.75 min (UPLC-MS); ESI-MS=360.1 [M+1]$^+$ (UPLC-MS); $^1$H NMR (400 MHz, DMSO-d$_6$) δ ppm 1.41 (d, J=6.85 Hz, 6H) 3.18 (s, 3H) 3.66 (s, 2H) 5.13 (quin, J=6.85 Hz, 1H) 6.53 (d, J=9.41 Hz, 1H) 7.09-7.17 (m, 1H) 7.73-7.82 (m, 2H) 7.96 (dd, J=9.41, 2.69 Hz, 1H) 8.16-8.23 (m, 2H) 8.79 (t, J=2.20 Hz, 2H).

Method B

To a beige suspension of 5-(5-bromopyridin-3-yl)-1-methylindolin-2-one (intermediate 1—method B) (91 g, 300 mmol) in dioxane (1.25 L, previously degassed at 45° C. for 10 min under N₂ inlet) under N₂ atmosphere were added successively 1-isopropyl-5-(4,4,5,5-tetramethyl-1,3,2-dioxaborolan-2-yl)pyridin-2(1H)-one (Intermediate A1—method B) (87 g, 330 mmol) and PdCl₂(dppf).CH₂Cl₂ complex (12.26 g, 15.01 mmol). A solution of K₂CO₃ (83 g, 600 mmol) in water (225 mL, previously degassed under vacuum and flushed with N₂) was added and the resulting mixture was heated up and stirred at 80° C. for 1.5 hr. The reaction mixture was cooled down to 15° C. and carefully quenched with an aqueous NaHCO₃ solution (1.5 L) and water (3 L) under vigorous stirring. The aqueous layer was extracted with EtOAc (5 L). The organic layer was washed with water (2×2 L) and brine (2 L). The aqueous phase was back extracted with EtOAc (5 L). The combined organic layers were dried over Na₂SO₄, filtered and concentrated under reduced pressure to a volume of 2 L. Silica gel (250 g) was added, stirred at 45° C. for 10 min and filtered through a pad of silica gel (250 g). The pad was washed with EtOAc (ca 3 L) and the filtrate was concentrated under reduced pressure to a volume of 2 L. Active charcoal (20 g) was added to the brown solution, heated up to 70° C., concentrated under reduced pressure to a volume of 2 L and filtered through a pad of silica gel. The filtrate was discarded. The pad was washed with MeOH (15 L) and the resulting yellow filtrate was concentrated under reduced pressure to a volume of 10 L. A fine suspension occurred. The beige yellow solid was filtrated off and the filtrate was concentrated to a 1 L volume under reduced pressure. The dark brown suspension was filtrated off and the filtrate was concentrated under reduced pressure, purified by silica gel column chromatography (3 kg SiO₂, CH₂Cl₂/MeOH 10:1) and triturated in EtOAc to afford a beige brownish solid. All the solids were combined and dissolved in MeOH. Active charcoal was added and the resulting mixture was heated up and stirred at reflux, filtered through a pad of silica gel and the resulting filtrate was concentrated under reduced pressure. MeOH (3 L) and 150 g of palladium scavenger (REAXA Quadrasil MTU previously washed with MeOH (3 L)) were added and the resulting mixture was heated up and stirred for 1.5 hr at 55° C., filtered and the resulting filtrate was cooled down to RT and concentrated to a volume of ca 0.7 L under reduced pressure. The beige suspension was cooled down to 4° C., filtrated off and dried under reduced pressure to afford the title product (42.9 g, 113 mmol, 37.7% yield) as beige solid monohydrate. Mp: 209.8° C.-210.3° C.; Pd analysis: 7 ppm (+/−25%); Rt=0.75 min (LC-MS 2); ESI-MS=360.2 [M+H]⁺ (UPLC-MS).

XRPD, TGA and DSC Analyses of Crystalline 5-(1'-isopropyl-6'-oxo-1',6'-dihydro-[3,3'-bipyridin]-5-yl)-1-methylindolin-2-one monohydrate XRPD analysis of free base crystalline 5-(1'-isopropyl-6'-oxo-1',6'-dihydro-[3,3'-bipyridin]-5-yl)-1-methylindolin-2-one monohydrate was carried out under the following experimental conditions:

| XRPD method | |
|---|---|
| Instrument | Bruker D8 Discover |
| Irradiation | CuKα (30 kV, 40 mA) |
| Detector | HI-STAR Area detector |
| Scan range | 2°-40° (2 theta value) |

DSC analysis was carried out under the following experimental conditions:

| DSC method | |
|---|---|
| Instrument | TA Instruments DSC Q2000 |
| Temperature range | 40° C.-300° C. at 10° C./min |
| Sample mass | 1-2 mg |
| Sample pan | Aluminium closed |
| Nitrogen flow | 50 ml/min |

TGA analysis was carried out under the following experimental conditions:

| TGA method | |
|---|---|
| Instrument | TA Instruments DSC Q5000 |
| Method | Equilibrate at 30° C.; temperature scan 30° C.-300° C. at 10° C./min |
| Sample mass | 1-2 mg |
| Nitrogen flow | 25 ml/min |

Free base 5-(1'-isopropyl-6'-oxo-1',6'-dihydro-[3,3'-bipyridin]-5-yl)-1-methylindolin-2-one monohydrate was obtained as a crystal following the procedure described above (method B).

The crystalline 5-(1'-isopropyl-6'-oxo-1',6'-dihydro-[3,3'-bipyridin]-5-yl)-1-methylindolin-2-one monohydrate was analysed by XRPD. List of most significant 2-Theta peaks from X-ray Powder Diffraction Pattern with tolerances±0.5 of 5-(1'-isopropyl-6'-oxo-1',6'-dihydro-[3,3'-bipyridin]-5-yl)-1-methylindolin-2-one monohydrate form (including low/weak peaks for information). Note: This list of peaks is not exhaustive but are only "inter alia".

| Angle (2-Theta °) | Intensity % | Angle (2-Theta °) | Intensity % |
|---|---|---|---|
| 9.5 | High | 17.7 | High |
| 11.7 | High | 18.9 | Low |
| 14.2 | Low | 20.2 | High |
| 14.8 | Medium | 21.3 | Low |
| 16.0 | High | 24.7 | Medium |
| 17.0 | Low | 26.6 | Low |

Figure 2:
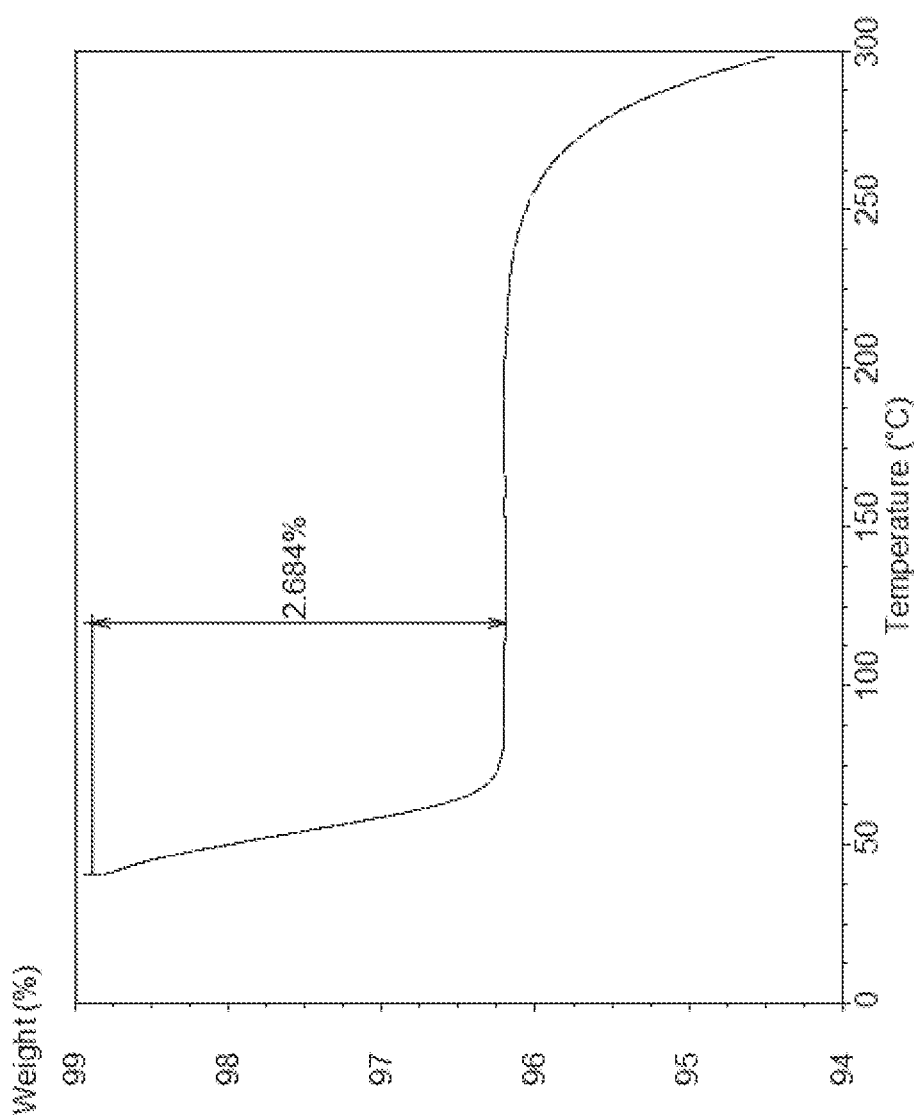
FIG. 2 shows the thermogravimetric analysis (TGA) of crystalline 5-(1'-isopropyl-6'-oxo-1',6'-dihydro-[3,3'-bipyridin]-5-yl)-1-methylindolin-2-one monohydrate.
Figure 3:
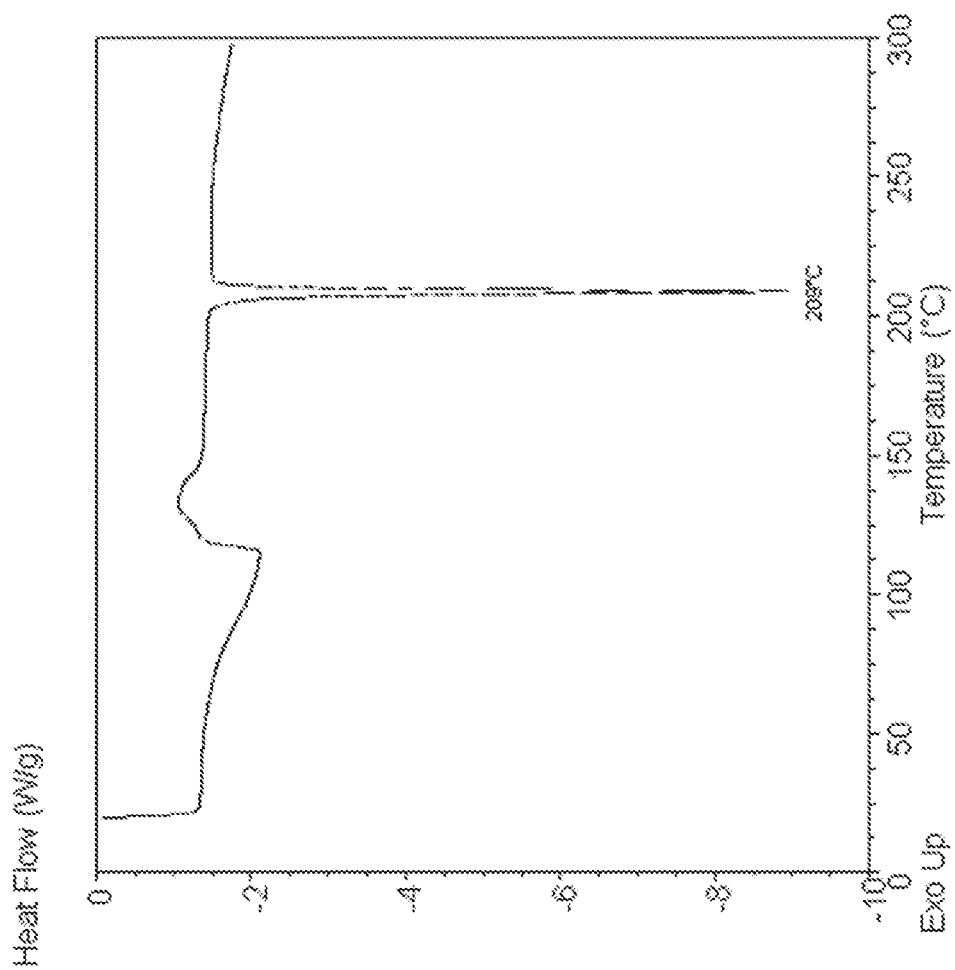
FIG. 3 shows the differential scanning calorimetry (DSC) of crystalline 5-(1'-isopropyl-6'-oxo-1',6'-dihydro-[3,3'-bipyridin]-5-yl)-1-methylindolin-2-one monohydrate.

Crystalline free base 5-(1'-isopropyl-6'-oxo-1',6'-dihydro-[3,3'-bipyridin]-5-yl)-1-methylindolin-2-one monohydrate was analysed by DSC and found to have two endotherms: first broad endotherm from 60-120° C. corresponding to the dehydration of the compound; followed by a second sharp endotherm of melting at about 209° C. (see FIG. 3). The TGA analysis shows 2.7% weight loss with temperature starting at about 40° C. (see FIG. 2).

Examples 2 to 19

The compounds listed in Table 1 were prepared in analogy to the procedure described in Example 1 using Intermediate 1 (method A) and the corresponding Intermediates A2 to A19 described above.

TABLE 1

| Example | Intermediate | Compound 1H NMR (solvent, δ) | UPLC-MS |
|---|---|---|---|
| 2 | A2 | 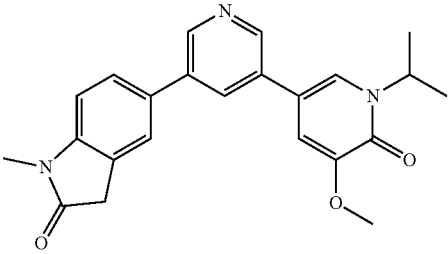<br>5-(1'-Isopropyl-5'-methoxy-6'-oxo-1',6'-dihydro-[3,3'-bipyridin]-5-yl)-1-methylindolin-2-one<br>(400 MHz, DMSO-$d_6$) δ ppm 1.39 (d, J = 6.85 Hz, 6 H) 3.19 (s, 3 H) 3.66 (s, 2 H) 3.84 (s, 3 H) 5.18 (quin, J = 6.79 Hz, 1 H) 7.14 (d, J = 8.80 Hz, 1 H) 7.27 (d, J = 2.20 Hz, 1 H) 7.74-7.81 (m, 3 H) 8.22 (t, J = 2.14 Hz, 1 H) 8.79 (d, J = 2.08 Hz, 1 H) 8.84 (d, J = 2.08 Hz, 1 H) | Rt = 0.75 min (UPLC-MS); ESI-MS = 390.1 [M + 1]$^+$ (UPLC-MS) |
| 3 | A3 | 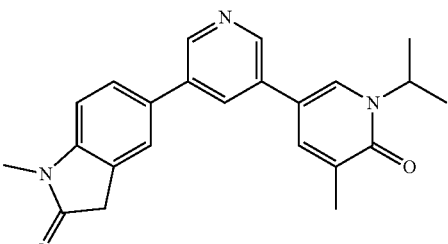<br>5-(1'-isopropyl-5'-methyl-6'-oxo-1',6'-dihydro-[3,3'-bipyridin]-5-yl)-1-methylindolin-2-one<br>(400 MHz, DMSO-$d_6$) δ ppm 1.40 (d, J = 6.85 Hz, 6 H) 2.12 (s, 3 H) 3.19 (s, 3 H) 3.66 (s, 2 H) 5.18 (quin, J = 6.82 Hz, 1 H) 7.14 (d, J = 8.68 Hz, 1 H) 7.74-7.81 (m, 2 H) 7.89 (s, 1 H) 8.07 (d, J = 2.32 Hz, 1 H) 8.16-8.23 (m, 1 H) 8.79 (dd, J = 8.93, 1.96 Hz, 2 H) | Rt = 0.81 min (UPLC-MS); ESI-MS = 374.2 [M + 1]$^+$ (UPLC-MS) |
| 4 | A4 | 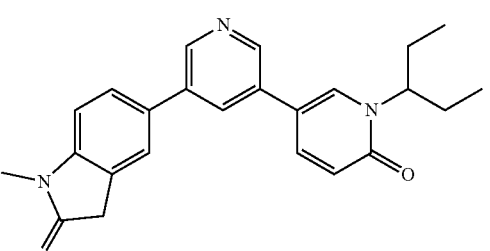<br>1-methyl-5-(6'-oxo-1'-(pentan-3-yl)-1',6'-dihydro-[3,3'-bipyridin]-5-yl)indolin-2-one<br>(400 MHz, DMSO-$d_6$) δ ppm 0.77 (t, J = 7.34 Hz, 6 H) 1.72-1.94 (m, 4 H) 3.18 (s, 3 H) 3.66 (s, 2 H) 4.81 (br. s., 1 H) 6.55 (d, J = 9.41 Hz, 1 H) 7.13 (d, J = 8.68 Hz, 1 H) 7.79 (d, J = 4.40 Hz, 2 H) 7.97 (dd, J = 9.48, 2.63 Hz, 1 H) 8.09 (d, J = 2.57 Hz, 1 H) 8.19 (t, J = 2.08 Hz, 1 H) 8.79 (t, J = 1.90 Hz, 2 H) | Rt = 0.84 min (UPLC-MS); ESI-MS = 388.1 [M + 1]$^+$ (UPLC-MS) |

TABLE 1-continued

| Example | Intermediate | Compound 1H NMR (solvent, δ) | UPLC-MS |
|---|---|---|---|
| 5 | A5 | 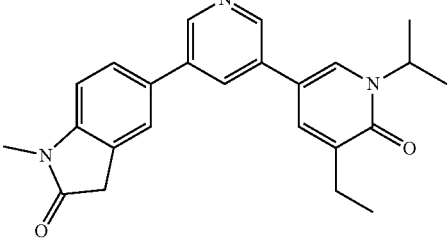<br>5-(5'-Ethyl-1'-isopropyl-6'-oxo-1',6'-dihydro-[3,3'-bipyridin]-5-yl)-1-methylindolin-2-one<br>(400 MHz, DMSO-$d_6$) δ ppm 1.18 (t, J = 7.46 Hz, 3 H) 1.40 (d, J = 6.85 Hz, 6 H) 3.19 (s, 3 H) 3.30-3.36 (m, 2 H) 3.66 (s, 2 H) 5.19 (quin, J = 6.85 Hz, 1 H) 7.14 (d, J = 8.68 Hz, 1 H) 7.78 (t, J = 2.57 Hz, 3 H) 8.06 (d, J = 2.57 Hz, 1 H) 8.20 (t, J = 2.14 Hz, 1 H) 8.79 (dd, J = 8.99, 2.14 Hz, 2 H) | Rt = 0.89 min (UPLC-MS); ESI-MS = 388.1 [M + 1]+ (UPLC-MS) |
| 6 | A6 | 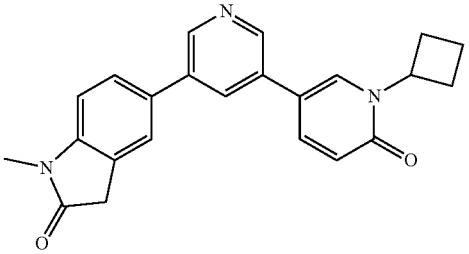<br>5-(1'-Cyclobutyl-6'-oxo-1',6'-dihydro-[3,3'-bipyridin]-5-yl)-1-methylindolin-2-one<br>(400 MHz, DMSO-$d_6$) δ ppm 1.73-1.86 (m, 2 H) 2.34 (m, 3 H) 2.68 (s, 1 H) 3.19 (s, 3 H) 3.66 (s, 2 H) 5.06-5.22 (m, 1 H) 6.51 (d, J = 9.41 Hz, 1 H) 7.14 (d, J = 8.56 Hz, 1 H) 7.76-7.81 (m, 2 H) 7.97 (dd, J = 9.41, 2.57 Hz, 1 H) 8.21-8.25 (m, 2 H) 8.81 (dd, J = 5.07, 2.02 Hz, 2 H) | Rt = 0.77 min (UPLC-MS); ESI-Ms = 372.1 [M + 1]+ (UPLC-MS) |
| 7 | A7 | 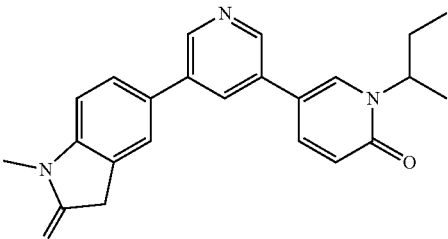<br>5-(1'-(sec-butyl)-6'-oxo-1',6'-dihydro-[3,3'-bipyridin]-5-yl)-1-methylindolin-2-one<br>(400 MHz, DMSO-$d_6$) δ ppm 0.80 (t, J = 7.34 Hz, 3 H) 1.39 (d, J = 6.85 Hz, 3 H) 1.71-1.95 (m, 2 H) 3.18 (s, 3 H) 3.66 (s, 2 H) 4.86-5.04 (m, 1 H) 6.54 (d, J = 9.41 Hz, 1 H) 7.14 (d, J = 8.68 Hz, 1 H) 7.72-7.84 (m, 2 H) 7.96 (dd, J = 9.48, 2.63 Hz, 1 H) 8.15 (d, J = 2.57 Hz, 1 H) 8.20 (t, J = 2.14 Hz, 1 H) 8.79 (s, 2 H) | Rt = 0.79 min (UPLC-MS); ESI-MS = 374.1 [M + 1]+ (UPLC-MS) |

TABLE 1-continued

| Example | Intermediate | Compound 1H NMR (solvent, δ) | UPLC-MS |
|---|---|---|---|
| 8 | A8 | 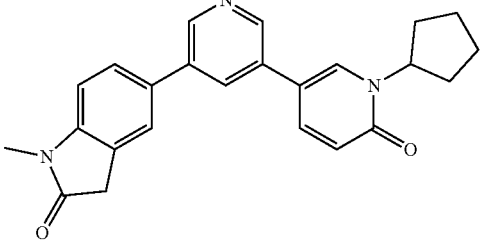<br>5-(1'-cyclopentyl-6'-oxo-1',6'-dihydro-[3,3'-bipyridin]-5-yl)-1-methylindolin-2-one<br>(400 MHz, DMSO-$d_6$) δ ppm 1.67 (br. s., 2 H) 1.89 (br. s., 4 H) 2.02 (br. s., 2 H) 3.19 (d, J = 5.26 Hz, 3 H) 3.66 (d, J = 4.89 Hz, 2 H) 5.03-5.23 (m, 1 H) 6.54 (dd, J = 9.41, 5.38 Hz, 1 H) 7.07-7.20 (m, 1 H) 7.77 (d, J = 4.89 Hz, 2 H) 7.95 (d, J = 9.05 Hz, 1 H) 8.19 (s, 1 H) 8.14 (s, 1 H) 8.79 (br. s., 2 H) | Rt = 0.83 min (UPLC-MS); ESI-MS = 386.1 $[M + 1]^+$ (UPLC-MS) |
| 9 | A9 | 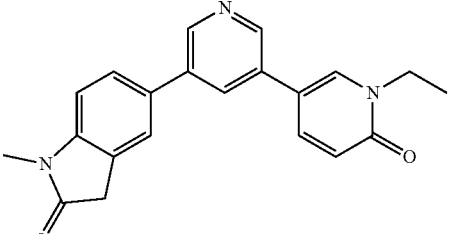<br>5-(1'-ethyl-6'-oxo-1',6'-dihydro-[3,3'-bipyridin]-5-yl)-1-methylindolin-2-one<br>(400 MHz, DMSO-$d_6$) δ ppm 1.30 (t, J = 7.15 Hz, 3 H) 3.19 (s, 3 H) 3.66 (s, 2 H) 4.02 (q, J = 7.13 Hz, 2 H) 6.53 (d, J = 9.41 Hz, 1 H) 7.14 (d, J = 8.56 Hz, 1 H) 7.74-7.81 (m, 2 H) 8.01 (dd, J = 9.48, 2.63 Hz, 1 H) 8.22 (t, J = 2.02 Hz, 1 H) 8.37 (d, J = 2.57 Hz, 1 H) 8.74- 8.82 (m, 2 H) | Rt = 0.67 min (UPLC-MS); ESI-MS = 346.1 $[M + 1]^+$ (UPLC-MS) |
| 10 | A10 | 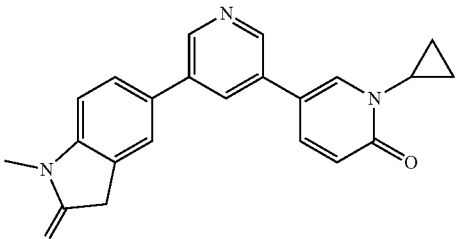<br>5-(1'-cyclopropyl-6'-oxo-1',6'-dihydro-[3,3'-bipyridin]-5-yl)-1-methylindolin-2-one<br>(400 MHz, DMSO-$d_6$) δ ppm 0.97-1.06 (m, 4 H) 3.18 (s, 3 H) 3.37-3.46 (m, 1 H) 3.65 (s, 2 H) 6.52 (d, J = 9.41 Hz, 1 H) 7.13 (d, J = 8.68 Hz, 1 H) 7.75-7.81 (m, 2 H) 7.96 (dd, J = 9.41, 2.57 Hz, 1 H) 8.01 (d, J = 2.45 Hz, 1 H) 8.18-8.22 (m, 1 H) 8.75-8.80 (m, 2 H) | Rt = 0.68 min (UPLC-MS); ESI-MS = 358.2 $[M + 1]^+$ (UPLC-MS) |

TABLE 1-continued

| Example | Intermediate | Compound 1H NMR (solvent, δ) | UPLC-MS |
|---|---|---|---|
| 11 | A11 | 5-(1'-(cyclobutylmethyl)-6'-oxo-1',6'-dihydro-[3,3'-bipyridin]-5-yl)-1-methylindolin-2-one<br>(400 MHz, DMSO-d$_6$) δ ppm 1.78-1.91 (m, 4 H) 1.91-2.00 (m, 2 H) 2.73-2.86 (m, 1 H) 3.19 (s, 3 H) 3.66 (s, 2 H) 4.04 (d, J = 7.46 Hz, 2 H) 6.53 (d, J = 9.41 Hz, 1 H) 7.14 (d, J = 8.68 Hz, 1 H) 7.72-7.82 (m, 2 H) 8.00 (dd, J = 9.48, 2.63 Hz, 1 H) 8.19 (t, J = 2.02 Hz, 1 H) 8.34 (d, J = 2.57 Hz, 1 H) 8.78 (dd, J = 7.95, 2.08 Hz, 2 H) | Rt = 0.84 min (UPLC-MS); ESI-MS = 386.0 [M + 1]$^+$ (UPLC-MS) |
| 12 | A12 | 1-methyl-5-(6'-oxo-1'-(2,2,2-trifluoroethyl)-1'6'-dihydro-[3,3'-bipyridin]-5-yl)indolin-2-one<br>(400 MHz, DMSO-d$_6$) δ ppm 3.19 (s, 3 H) 3.66 (s, 2 H) 4.92 (q, J = 9.09 Hz, 2 H) 6.66 (d, J = 9.54 Hz, 1 H) 7.14 (d, J = 8.80 Hz, 1 H) 7.75-7.80 (m, 2 H) 8.12 (dd, J = 9.60, 2.63 Hz, 1 H) 8.19 (t, J = 2.14 Hz, 1 H) 8.33-8.40 (m, 1 H) 8.75 (d, J = 2.08 Hz, 1 H) 8.83 (d, J = 2.08 Hz, 1 H) | Rt = 0.78 min (UPLC-MS); ESI-MS = 400.0 [M + 1]$^+$ (UPLC-MS) |
| 13 | A13 | 5-(1'-(2-ethylbutyl)-6'-oxo-1',6'-dihydro-[3,3'-bipyridin]-5-yl)-1-methylindolin-2-one<br>(400 MHz, DMSO-d$_6$) δ ppm 0.87 (t, J = 7.21 Hz, 6 H) 1.22-1.36 (m, 4 H) 1.79-1.94 (m, 1 H) 3.15-3.22 (m, 3 H) 3.66 (s, 2 H) 3.91 (d, J = 7.21 Hz, 2 H) 6.53 (d, J = 9.29 Hz, 1 H) 7.14 (d, J = 8.31 Hz, 1 H) 7.77 (br. s., 2 H) 8.01 (d, J = 9.54 Hz, 1 H) 8.19 (d, J = 1.96 Hz, 1 H) 8.28 (br. s., 1 H) 8.74-8.81 (m, 2 H) | Rt = 0.94 min (UPLC-MS); ESI-MS = 402.1 [M + 1]$^+$ (UPLC-MS) |

TABLE 1-continued

| Example | Intermediate | Compound 1H NMR (solvent, δ) | UPLC-MS |
|---|---|---|---|
| 14 | A14 | 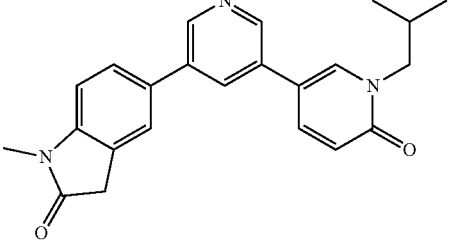<br>5-(1'-isobutyl-6'-oxo-1',6'-dihydro-[3,3'-bipyridin]-5-yl)-1-methylindolin-2-one<br>(400 MHz, DMSO-$d_6$) δ ppm 0.90 (d, J = 6.72 Hz, 6 H) 2.17 (quin, J = 6.89 Hz, 1 H) 3.18 (s, 3 H) 3.66 (s, 2 H) 3.83 (d, J = 7.58 Hz, 2 H) 6.54 (d, J = 9.41 Hz, 1 H) 7.14 (d, J = 8.68 Hz, 1 H) 7.72-7.82 (m, 2 H) 8.02 (dd, J = 9.48, 2.63 Hz, 1 H) 8.20 (t, J = 2.14 Hz, 1 H) 8.30 (d, J = 2.57 Hz, 1 H) 8.78 (dd, J = 5.99, 1.96 Hz, 2 H) | Rt = 0.80 min (UPLC-MS); ESI-MS = 374.0 [M + 1]$^+$ (UPLC-MS) |
| 15 | A15 | 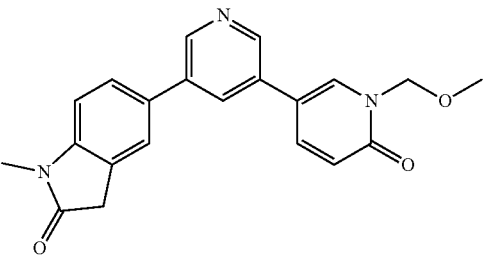<br>5-(1'-(methoxymethyl)-6'-oxo-1',6'-dihydro-[3,3'-bipyridin]-5-yl)-1-methylindolin-2-one<br>(400 MHz, DMSO-$d_6$) δ ppm 3.18 (s, 3 H) 3.35 (s, 3 H) 3.65 (s, 2 H) 5.33 (s, 2 H) 6.59 (d, J = 9.54 Hz, 1 H) 7.14 (d, J = 8.56 Hz, 1 H) 7.73-7.84 (m, 2 H) 8.07 (dd, J = 9.54, 2.69 Hz, 1 H) 8.22 (t, J = 2.08 Hz, 1 H) 8.35 (d, J = 2.69 Hz, 1 H) 8.81 (d, J = 2.08 Hz, 1 H) 8.78 (d, J = 2.20 Hz, 1 H) | Rt = 0.65 min (UPLC-MS); ESI-MS = 362.2 [M + 1]$^+$ (UPLC-MS) |
| 16 | A16 | 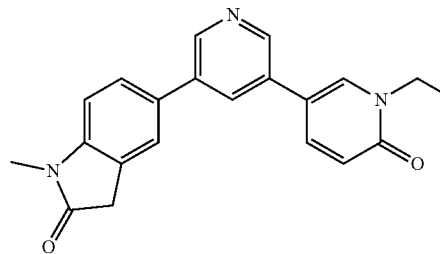<br>1-methyl-5-(6'-oxo-1'-(3,3,3-trifluoropropyl)-1',6'-dihydro-[3,3'-bipyridin]-5-yl)indolin-2-one<br>(400 MHz, DMSO-$d_6$) δ ppm 2.74-2.92 (m, 2 H) 3.19 (s, 3 H) 3.66 (s, 2 H) 4.25 (t, J = 7.21 Hz, 2 H) 6.57 (d, J = 9.54 Hz, 1 H) 7.14 (d, J = 8.80 Hz, 1 H) 7.72-7.82 (m, 2 H) 8.06 (dd, J = 9.54, 2.57 Hz, 1 H) 8.22 (t, J = 2.14 Hz, 1 H) 8.40 (d, J = 2.57 Hz, 1 H) 8.80 (dd, J = 6.85, 2.08 Hz, 2 H) | Rt = 0.79 min (UPLC-MS); ESI-MS = 414.1 [M + 1]$^+$ (UPLC-MS) |

TABLE 1-continued

| Example | Intermediate | Compound 1H NMR (solvent, δ) | UPLC-MS |
|---|---|---|---|
| 17 | A17 | 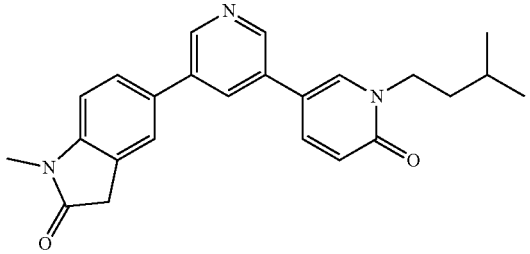 5-(1'-isopentyl-6'-oxo-1',6'-dihydro-[3,3'-bipyridin]-5-yl)-1-methylindolin-2-one<br><br>(400 MHz, DMSO-$d_6$) δ ppm 0.95 (d, J = 5.99 Hz, 6 H) 1.53-1.67 (m, 3 H) 3.18 (s, 3 H) 3.66 (s, 2 H) 3.94-4.05 (m, 2 H) 6.52 (d, J = 9.41 Hz, 1 H) 7.14 (d, J = 8.68 Hz, 1 H) 7.74-7.82 (m, 2 H) 8.00 (dd, J = 9.41, 2.69 Hz, 1 H) 8.20 (t, J = 2.08 Hz, 1 H) 8.35 (d, J = 2.69 Hz, 1 H) 8.78 (t, J = 2.45 Hz, 2 H) | Rt = 0.89 min (UPLC-MS); ESI-MS = 388.1 [M + 1]$^+$ (UPLC-MS) |
| 18 | A18 | 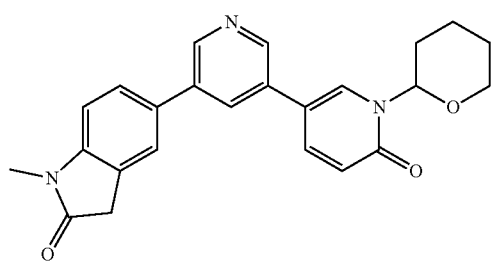 1-methyl-5-(6'-oxo-1'-(tetrahydro-2H-pyran-2-yl)-1',6'-dihydro-[3,3'-bipyridin]-5-yl)indolin-2-one<br><br>(400 MHz, DMSO-$d_6$) δ ppm 1.49-1.60 (m, 1 H) 1.60-1.82 (m, 3 H) 1.82-1.99 (m, 2 H) 3.15-3.22 (m, 3 H) 3.66 (s, 2 H) 3.67-3.74 (m, 1 H) 4.10 (d, J = 11.37 Hz, 1 H) 5.82-5.93 (m, 1 H) 6.58 (d, J = 9.54 Hz, 1 H) 7.14 (d, J = 8.68 Hz, 1 H) 7.74-7.83 (m, 2 H) 8.01 (dd, J = 9.48, 2.63 Hz, 1 H) 8.13 (d, J = 2.57 Hz, 1 H) 8.18 (t, J = 2.08 Hz, 1 H) 8.81 (d, J = 1.96 Hz, 1 H) 8.76 (d, J = 2.08 Hz, 1 H) | Rt = 0.80 min (UPLC-MS); ESI-MS = 401.8 [M + 1]$^+$ (UPLC-MS) |
| 19 | A19 | 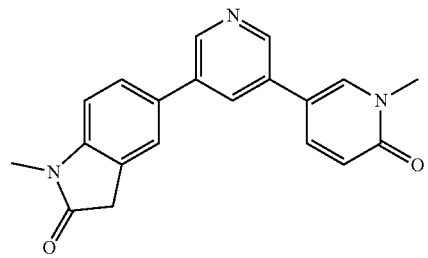 1-methyl-5-(1'-methyl-6'-oxo-1',6'-dihydro-[3,3'-bipyridin]-5-yl)indolin-2-one<br><br>(400 MHz, DMSO-$d_6$) δ ppm 3.18 (s, 3 H) 3.54 (s, 3 H) 3.65 (s, 2 H) 6.54 (d, J = 9.41 Hz, 1 H) 7.13 (d, J = 8.68 Hz, 1 H) 7.75-7.81 (m, 2 H) 8.02 (dd, J = 9.41, 2.57 Hz, 1 H) 8.20 (s, 1 H) 8.38 (d, J = 2.45 Hz, 1 H) 8.78 (dd, J = 9.29, 1.83 Hz, 2 H) | Rt = 0.62 min (UPLC-MS); ESI-MS = 332.0 [M + 1]$^+$ (UPLC-MS) |

Example 20: 1-Ethyl-5-(1'-isopropyl-6'-oxo-1',6'-dihydro-[3,3'-bipyridin]-5-yl)indolin-2-one

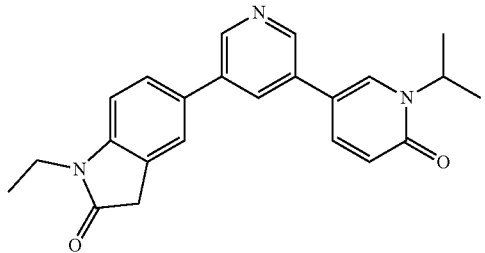 [SMILES: CCN1C(=O)Cc2cc(-c3cncc(-c4ccc(=O)n(C(C)C)c4)c3)ccc21]

The title compound was prepared in analogy to the procedure described in Example 1 using 5'-bromo-1-isopropyl-[3,3'-bipyridin]-6(1H)-one Intermediate 2 and 1-ethyl-5-(4,4,5,5-tetramethyl-1,3,2-dioxaborolan-2-yl)indolin-2-one Intermediate B1 in ACN at 120° C. for 45 min under MW irradiation. The crude material was purified by flash column chromatography on silica gel (DCM/0 to 20% MeOH) to afford the title product as a brown solid. Rt=0.80 min (UPLC-MS); ESI-MS=374.1 [M+1]+ (UPLC-MS); $^1$H NMR (400 MHz, DMSO-$d_6$) δ ppm 1.18 (t, J=7.09 Hz, 3H) 1.36-1.44 (m, 6H) 3.65 (s, 2H) 3.76 (q, J=7.05 Hz, 2H) 5.13 (quin, J=6.79 Hz, 1H) 6.54 (d, J=9.41 Hz, 1H) 7.19 (d, J=7.95 Hz, 1H) 7.73-7.80 (m, 2H) 7.96 (dd, J=9.41, 2.69 Hz, 1H) 8.15-8.26 (m, 2H) 8.79 (dd, J=5.07, 2.14 Hz, 2H).

Examples 21 to 34

The compounds listed in Table 2 were prepared in analogy to the procedure described in Example 20 using Intermediate 2 and the corresponding Intermediates B2 to B14 described above.

TABLE 2

| Example | Intermediate | Compound 1H NMR (solvent, δ) | UPLC-MS |
|---|---|---|---|
| 21 | B2 | 1-Isopropyl-5-(1'-isopropyl-6'-oxo-1',6'-dihydro-[3,3'-bipyridin]-5-yl)indolin-2-one<br>(400 MHz, DMSO-$d_6$) δ ppm 1.44 (d, J = 6.97 Hz, 6 H) 1.40 (d, J = 6.85 Hz, 6 H) 3.63 (s, 2 H) 4.60 (quin, J = 7.03 Hz, 1 H) 5.13 (quin, J = 6.82 Hz, 1 H) 6.54 (d, J = 9.41 Hz, 1 H) 7.30 (d, J = 8.31 Hz, 1 H) 7.67-7.79 (m, 2 H) 7.95 (dd, J = 9.41, 2.69 Hz, 1 H) 8.19 (s, 2 H) 8.79 (dd, J = 8.25, 2.14 Hz, 2 H). | Rt = 0.87 min (UPLC-MS); ESI-MS = 388.1 [M + 1]+ (UPLC-MS) |
| 22 | B3 | 3-Ethyl-5-(1'-isopropyl-6'-oxo-1',6'-dihydro-[3,3'-bipyridin]-5-yl)-1-methylindolin-2-one<br>(400 MHz, DMSO-$d_6$) δ ppm 0.76-0.85 (m, 3 H) 1.36-1.44 (m, 6 H) 2.00 (d, J = 3.42 Hz, 2 H) 3.15-3.22 (m, 3 H) 3.60 (br. s., 1 H) 5.06-5.21 (m, 1 H) 6.54 (dd, J = 9.35, 1.77 Hz, 1 H) 7.15 (dd, J = 8.01, 1.77 Hz, 1 H) 7.75-7.85 (m, 2 H) 7.96 (d, J = 9.29 Hz, 1 H) 8.17-8.24 (m, 2 H) 8.77-8.87 (m, 2 H). | Rt = 0.85 min (UPLC-MS); ESI-MS = 388.3 [M + 1]+ (UPLC-MS) |
| 23 | B4 | 3,3-Difluoro-5-(1'-isopropyl-6'-oxo-1',6'-dihydro-[3,3'-bipyridin]-5-yl)-1-methylindolin-2-one | Rt = 0.89 min (UPLC-MS); ESI-MS = 396.2 [M + 1]+ (UPLC-MS) |

TABLE 2-continued

| Example | Intermediate | Compound 1H NMR (solvent, δ) | UPLC-MS |
|---|---|---|---|
| | | (400 MHz, DMSO-$d_6$) δ ppm 1.41 (d, J = 6.85 Hz, 6 H) 3.25 (s, 3 H) 5.14 (quin, J = 6.82 Hz, 1 H) 6.55 (d, J = 9.41 Hz, 1 H) 7.40 (d, J = 8.31 Hz, 1 H) 8.00 (dd, J = 9.41, 2.69 Hz, 1 H) 8.14 (d, J = 8.07 Hz, 1 H) 8.21 (d, J = 2.57 Hz, 1 H) 8.27-8.32 (m, 2 H) 8.87 (dd, J = 3.36, 2.26 Hz, 2 H). | |
| 24 (Compound B) | B5 | 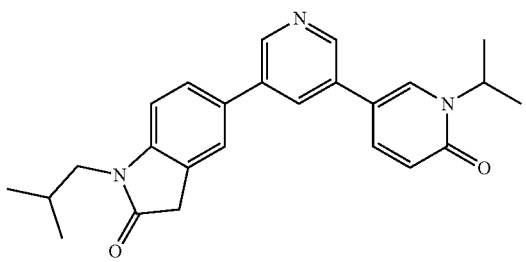

1-Isobutyl-5-(1'-isopropyl-6'-oxo-1',6'-dihydro-[3,3'-bipyridin]-5-yl)indolin-2-one (400 MHz, DMSO-$d_6$) δ ppm 0.92 (d, J = 6.60 Hz, 6 H) 1.40 (d, J = 6.85 Hz, 6 H) 2.02-2.15 (m, 1 H) 3.54 (d, J = 7.46 Hz, 2 H) 3.69 (s, 2 H) 5.13 (quin, J = 6.88 Hz, 1 H) 6.53 (d, J = 9.54 Hz, 1 H) 7.18 (d, J = 8.19 Hz, 1 H) 7.74 (d, J = 8.19 Hz, 1 H) 7.77 (s, 1 H) 7.96 (dd, J = 9.41, 2.57 Hz, 1 H) 8.19 (d, J = 2.20 Hz, 2 H) 8.79 (dd, J = 6.48, 1.96 Hz, 2 H). | Rt = 0.95 min (UPLC-MS); ESI-MS = 402.1 [M + 1]$^+$ (UPLC-MS) |
| 25 | B6 | 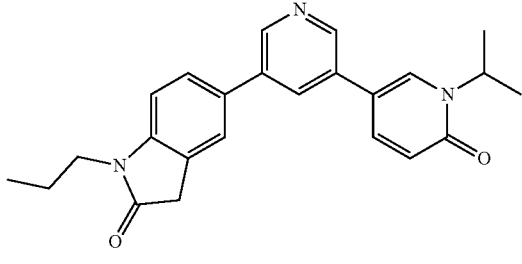

5-(1'-Isopropyl-6'-oxo-1',6'-dihydro-[3,3'-bipyridin]-5-yl)-1-propylindolin-2-one (400 MHz, DMSO-$d_6$) δ ppm 0.91 (t, J = 7.40 Hz, 3 H) 1.41 (d, J = 6.72 Hz, 6 H) 1.64 (sxt, J = 7.21 Hz, 2 H) 3.64-3.73 (m, 4 H) 5.13 (quin, J = 6.82 Hz, 1 H) 6.54 (d, J = 9.41 Hz, 1 H) 7.19 (d, J = 8.19 Hz, 1 H) 7.72-7.79 (m, 2 H) 7.96 (dd, J = 9.41, 2.57 Hz, 1 H) 8.17-8.22 (m, 2 H) 8.79 (dd, J = 5.87, 2.08 Hz, 2 H). | Rt = 0.87 min (UPLC-MS); ESI-MS = 388.1 [M + 1]$^+$ (UPLC-MS) |
| 26 | B7 | 6-(1'-Isopropyl-6'-oxo-1',6'-dihydro-[3,3'-bipyridin]-5-yl)-1-methylindolin-2-one (400 MHz, DMSO-$d_6$) δ ppm 1.41 (d, J = 6.85 Hz, 6 H) 3.23 (s, 3 H) 3.63 (s, 2 H) 5.05-5.23 (m, 1 H) 6.55 (d, J = 9.41 Hz, 1 H) 7.38-7.43 (m, 1 H) 7.44-7.51 (m, 2 H) 7.97 (dd, J = 9.41, 2.69 Hz, 1 H) 8.20 (d, J = 2.57 Hz, 1 H) 8.27 (t, J = 2.20 Hz, 1 H) 8.86 (dd, J = 5.69, 2.14 Hz, 2 H). | Rt = 0.75 min (UPLC-MS); ESI-MS = 360.1 [M + 1]$^+$ (UPLC-MS) |

TABLE 2-continued

| Example | Intermediate | Compound 1H NMR (solvent, δ) | UPLC-MS |
|---|---|---|---|
| 27 | B8 | 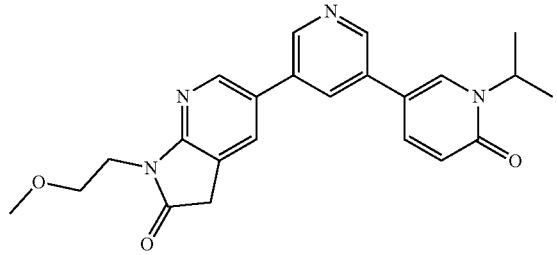<br>5-(1'-Isopropyl-6'-oxo-1',6'-dihydro-[3,3'-bipyridin]-5-yl)-1-(2-methoxyethyl)-1H-pyrrolo[2,3-b]pyridin-2(3H)-one<br>(400 MHz, DMSO-$d_6$) δ ppm 1.41 (d, J = 6.85 Hz, 6 H) 3.26 (s, 3 H) 3.65 (t, J = 5.87 Hz, 2 H) 3.75 (s, 2 H) 3.94 (t, J = 5.93 Hz, 2 H) 5.14 (quin, J = 6.82 Hz, 1 H) 6.54 (d, J = 9.54 Hz, 1 H) 7.97 (dd, J = 9.41, 2.57 Hz, 1 H) 8.14 (s, 1 H) 8.21 (d, J = 2.57 Hz, 1 H) 8.27 (t, J = 2.14 Hz, 1 H) 8.65 (d, J = 1.83 Hz, 1 H) 8.86 (d, J = 2.08 Hz, 1 H) 8.83 (d, J = 2.08 Hz, 1 H). | Rt = 0.71 min (UPLC-MS); ESI-MS = 405.1 [M + 1]$^+$ (UPLC-MS) |
| 28 | B9 | 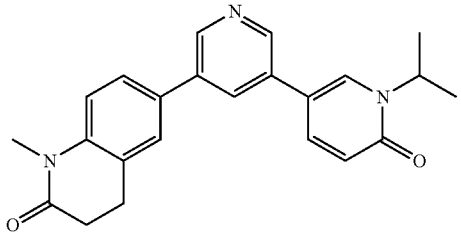<br>6-(1'-Isopropyl-6'-oxo-1',6'-dihydro-[3,3'-bipyridin]-5-yl)-1-methyl-3,4-dihydroquinolin-2(1H)-one<br>(400 MHz, DMSO-$d_6$) δ ppm 1.41 (d, J = 6.85 Hz, 6 H) 2.57-2.65 (m, 2 H) 2.94-3.02 (m, 2 H) 3.31 (s, 3 H) 5.13 (quin, J = 6.85 Hz, 1 H) 6.54 (d, J = 9.41 Hz, 1 H) 7.24 (d, J = 8.19 Hz, 1 H) 7.72-7.79 (m, 2 H) 7.96 (dd, J = 9.48, 2.63 Hz, 1 H) 8.19 (d, J = 2.45 Hz, 1 H) 8.23 (t, J = 2.20 Hz, 1 H) 8.82 (t, J = 2.02 Hz, 2 H). | Rt = 0.79 min (UPLC-MS); ESI-MS = 374.1 [M + 1]$^+$ (UPLC-MS) |
| 29 | B10 | 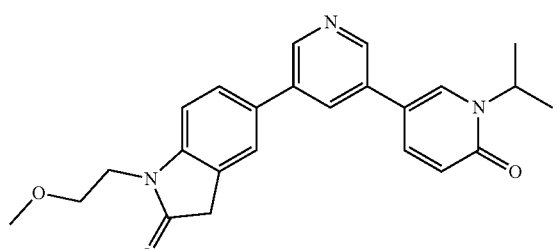<br>5-(1'-Isopropyl-6'-oxo-1',6'-dihydro-[3,3'-bipyridin]-5-yl)-1-(2-methoxyethyl)indolin-2-one<br>(400 MHz, DMSO-$d_6$) δ ppm 1.41 (d, J = 6.85 Hz, 6 H) 3.25 (s, 3 H) 3.58 (t, J = 5.50 Hz, 2 H) 3.67 (s, 2 H) 3.90 (t, J = 5.50 Hz, 2 H) 5.13 (quin, J = 6.85 Hz, 1 H) 6.54 (d, J = 9.41 Hz, 1 H) 7.21 (d, J = 8.07 Hz, 1 H) 7.72-7.79 (m, 2 H) 7.96 (dd, J = 9.41, 2.57 Hz, 1 H) 8.17-8.22 (m, 2 H) 8.79 (dd, J = 5.26, 2.08 Hz, 2 H). | Rt = 0.76 min (UPLC-MS); ESI-MS = 404.1 [M + 1]$^+$ (UPLC-MS) |

TABLE 2-continued

| Example | Intermediate | Compound 1H NMR (solvent, δ) | UPLC-MS |
|---|---|---|---|
| 30 (Compound C) | B11 | 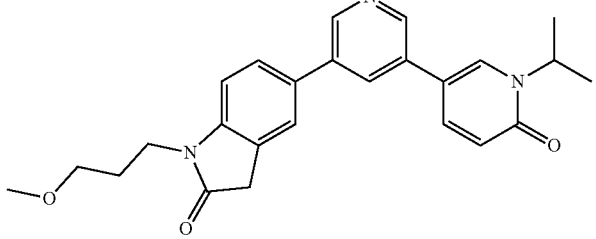 5-(1'-Isopropyl-6'-oxo-1',6'-dihydro-[3,3'-bipyridin]-5-yl)-1-(3-methoxypropyl)indolin-2-one (400 MHz, DMSO-d$_6$) δ ppm 1.41 (d, J = 6.85 Hz, 6 H) 1.83 (quin, J = 6.85 Hz, 2 H) 3.25 (s, 3 H) 3.38 (t, J = 5.50 Hz, 2 H) 3.66 (s, 2 H) 3.76 (t, J = 5.50 Hz, 2 H) 5.13 (quin, J = 6.85 Hz, 1 H) 6.54 (d, J = 9.41 Hz, 1 H) 7.14 (d, J = 8.07 Hz, 1 H) 7.72-7.79 (m, 2 H) 7.96 (dd, J = 9.41, 2.57 Hz, 1 H) 8.17-8.22 (m, 2 H) 8.79 (dd, J = 5.26, 2.08 Hz, 2 H). | Rt = 0.81 min (UPLC-MS); ESI-MS = 418.8 [M + 1]$^+$ (UPLC-MS) |
| 31 | B12 | 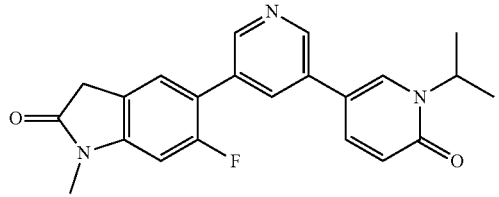 5-(1'-Isopropyl-6'-oxo-1',6'-dihydro-[3,3'-bipyridin]-5-yl)-1,3,3-trimethyl-1H-pyrrolo[2,3-b]pyridin-2(3H)-one (400 MHz, DMSO-d$_6$) δ ppm 1.38 (d, J = 6.85 Hz, 6 H) 3.11-3.21 (s, 3 H) 3.62 (s, 2 H) 5.11 (quin, J = 6.82 Hz, 1 H) 6.52 (d, J = 9.41 Hz, 1 H) 7.14 (d, J = 11.13 Hz, 1 H) 7.59 (d, J = 7.70 Hz, 1 H) 7.90 (dd, J = 9.48, 2.38 Hz, 1 H) 8.10 (s, 1 H) 8.16 (d, J = 2.32 Hz, 1 H) 8.64 (s, 1 H) 8.83 (d, J = 1.96 Hz, 1 H). | Rt = 0.78 min (UPLC-MS); ESI-MS = 378.1 [M + 1]$^+$ (UPLC-MS) |
| 32 | B13 | 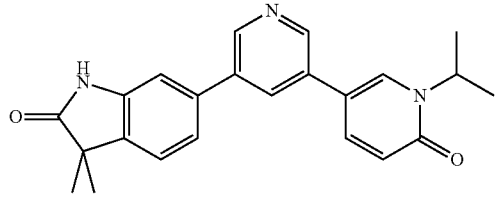 6-(1'-isopropyl-6'-oxo-1',6'-dihydro-[3,3'-bipyridin]-5-yl)-3,3-dimethylindolin-2-one (400 MHz, DMSO-d$_6$) δ ppm 1.31 (s, 6 H) 1.40 (d, J = 6.85 Hz, 6 H) 5.13 (quin, J = 6.85 Hz, 1 H) 6.53 (d, J = 9.41 Hz, 1 H) 7.13-7.24 (m, 1 H) 7.39 (dd, J = 7.76, 1.41 Hz, 1 H) 7.45 (d, J = 7.70 Hz, 1 H) 7.95 (dd, J = 9.35, 2.63 Hz, 1 H) 8.20 (d, J = 2.32 Hz, 2 H) 8.74 (d, J = 1.83 Hz, 1 H) 8.84 (d, J = 2.08 Hz, 1 H) 10.51 (s, 1 H). | Rt = 0.81 min (UPLC-MS); ESI-MS = 374.1 [M + 1]$^+$ (UPLC-MS) |
| 33 | B14 | 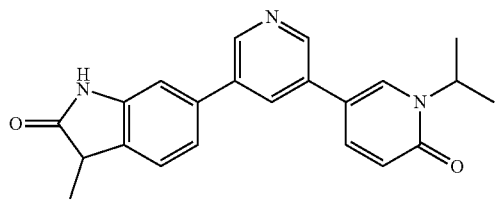 6-(1'-isopropyl-6'-oxo-1',6'-dihydro-[3,3'-bipyridin]-5-yl)-3-methylindolin-2-one (400 MHz, DMSO-d$_6$) δ ppm 1.35-1.42 (m, 9 H) 3.50 (q, J = 7.78 Hz, 1 H) 5.13 (quin, J = 13.60 Hz, 1 H) 6.53 | Rt = 0.75 min (UPLC-MS); ESI-MS = 360.0 [M + 1]$^+$ (UPLC-MS) |

TABLE 2-continued

| Example | Intermediate | Compound 1H NMR (solvent, δ) | UPLC-MS |
|---|---|---|---|
| | | (d, J = 9.41 Hz, 1 H) 7.17 (s, 1 H) 7.34-7.46 (m, 2 H) 7.95 (dd, J = 9.54, 2.57 Hz, 1 H) 8.20 (d, J = 2.08 Hz, 2 H) 8.75 (d, J = 2.08 Hz, 1 H) 8.84 (d, J = 2.08 Hz, 1 H) 10.51 (s, 1 H). | |
| 34 | Commercial 5-(4,4,5,5-tetramethyl-1,3,2-dioxaborolan-2-yl)indolin-2-one | 5-(1'-isopropyl-6'-oxo-1',6'-dihydro-[3,3'-bipyridin]-5-yl)indolin-2-one<br><br>(400 MHz, DMSO-d$_6$) δ ppm 1.40 (d, J = 6.85 Hz, 6 H) 3.58 (s, 2 H) 5.06-5.20 (m, 1 H) 6.53 (d, J = 9.54 Hz, 1 H) 6.96 (d, J = 8.19 Hz, 1 H) 7.66 (d, J = 7.70 Hz, 1 H) 7.72 (s, 1 H) 7.95 (d, J = 7.34 Hz, 1 H) 8.15-8.22 (m, 2 H) 8.77 (d, J = 9.66 Hz, 2 H) 10.54 (s, 1 H). | Rt = 0.64 min (UPLC-MS); ESI-MS = 346.2 [M + 1]$^+$ (UPLC-MS) |

Example 35: 5-(1'-isopropyl-6'-oxo-1',6'-dihydro-[3,3'-bipyridin]-5-yl)-1,7-dimethylindolin-2-one

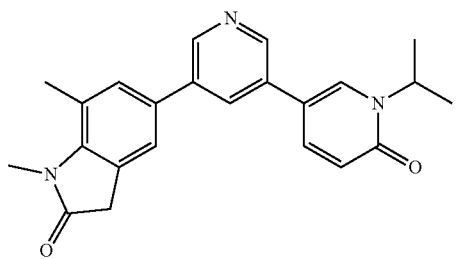 [SMILES: Cc1cc(-c2cncc(-c3ccc(=O)n(C(C)C)c3)c2)cc2c1N(C)C(=O)C2]

The title compound was prepared in analogy to the procedure described in Example 20 using (1'-isopropyl-6'-oxo-1',6'-dihydro-[3,3'-bipyridin]-5-yl)boronic acid (Intermediate 3) and 5-bromo-1,7-dimethylindolin-2-one (Intermediate B15) at 120° C. for 30 min under MW irradiation. Palladium was removed from the mixture using a PL-Thiol SPE cartridge. The crude product was purified by flash column chromatography (DCM/MeOH 1:0 to 8:2). Rt=0.80 min (UPLC-MS); ESI-MS=374.1 [M+1]$^+$ (UPLC-MS); $^1$H NMR (400 MHz, DMSO-d$_6$) δ ppm 1.41 (d, J=6.85 Hz, 6H) 2.64 (s, 3H) 3.45 (s, 3H) 3.62 (s, 2H) 5.13 (quin, J=6.76 Hz, 1H) 6.54 (d, J=9.41 Hz, 1H) 7.54 (s, 1H) 7.61 (s, 1H) 7.95 (dd, J=9.48, 2.63 Hz, 1H) 8.18 (d, J=1.96 Hz, 2H) 8.79 (t, J=2.26 Hz, 2H).

Examples 36 to 41

The compounds listed in Table 3 were prepared in analogy to the procedure described in Example using Intermediate 3 and the corresponding Intermediates B16 to B20 described above.

TABLE 3

| Example | Intermediate | Structure 1H NMR (solvent, δ) | UPLC-MS |
|---|---|---|---|
| 36 | B16 | 7-Fluoro-5-(1'-isopropyl-6'-oxo-1',6'-dihydro-[3,3'-bipyridin]-5-yl)-1-methylindolin-2-one<br><br>(400 MHz, DMSO-d$_6$) δ ppm 1.41 (d, J = 6.85 Hz, 6 H) 3.35 (br. s., 3 H) 3.73 (s, 2 H) 5.13 (quin, J = 6.85 Hz, 1 H) 6.54 (d, J = 9.41 Hz, 1H ) 7.67 (s, 1 H) 7.77 (d, | Rt = 0.81 min (UPLC-MS); ESI-MS = 378.0 [M + 1]$^+$ (UPLC-MS) |

TABLE 3-continued

| Example | Intermediate | Structure 1H NMR (solvent, δ) | UPLC-MS |
|---|---|---|---|
| | | J = 12.84 Hz, 1 H) 7.98 (dd, J = 9.48, 2.63 Hz, 1 H) 8.20 (d, J = 2.45 Hz, 1 H) 8.24 (t, J = 2.02 Hz, 1 H) 8.83 (d, J = 2.08 Hz, 2 H). | |
| 37 | B17 | 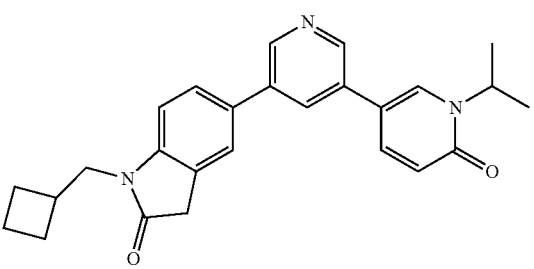<br>6-(1'-Isopropyl-6'-oxo-1',6'-dihydro-[3,3'-bipyridin]-5-yl)-1-methyl-3,4-dihydro-1,8-naphthyridin-2(1H)-one<br><br>(400 MHz, DMSO-d$_6$) δ ppm 1.41 (d, J = 6.85 Hz, 6 H) 2.65-2.74 (m, 2 H) 2.95-3.05 (m, 2 H) 3.38 (s, 3 H) 5.14 (quin, J = 6.85 Hz, 1 H) 6.55 (d, J = 9.41 Hz, 1 H) 7.97 (dd, J = 9.48, 2.63 Hz, 1 H) 8.17 (d, J = 2.20 Hz, 1 H) 8.21 (d, J = 2.57 Hz, 1 H) 8.31 (t, J = 2.14 Hz, 1 H) 8.75 (d, J = 2.32 Hz, 1 H) 8.87 (t, J = 1.90 Hz, 2 H). | Rt = 0.75 min (UPLC-MS); ESI-MS = 375.1 [M + 1]$^+$ (UPLC-MS) |
| 38 (Compound D) | B18 | 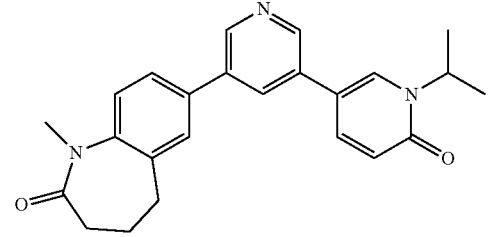<br>1-(cyclobutylmethyl)-5-(1'-isopropyl-6'-oxo-1',6'-dihydro-[3,3'-bipyridin]-5-yl)indolin-2-one<br><br>(400 MHz, DMSO-d$_6$) δ ppm 1.40 (d, J = 6.85 Hz, 6 H) 1.73-1.89 (m, 4 H) 1.91-2.04 (m, 2 H) 2.69-2.80 (m, 1 H) 3.67 (s, 2H) 3.77 (d, J = 7.21 Hz, 2H) 5.13 (quin, J = 6.85 Hz, 1 H) 6.53 (d, J = 9.41 Hz, 1 H) 7.18 (d, J = 8.19 Hz, 1 H) 7.67-7.80 (m, 2 H) 7.95 (dd, J = 9.41, 2.69 Hz, 1 H) 8.19 (d, J = 2.20 Hz, 2 H) 8.79 (dd, J = 7.21, 2.08 Hz, 2 H). | Rt = 0.99 min (UPLC-MS); ESI-MS = 414.1 [M + 1]$^+$ (UPLC-MS) |
| 39 | B19 | 7-1'-isopropyl-6'-oxo-1',6'-dihydro-[3,3'-bipyridin]-5-yl)-1-methyl-4,5-dihydro-1H-benzo[b]azepin-2(3H)-one<br><br>(400 MHz, DMSO-d$_6$) δ ppm 1.41 (d, J = 6.85 Hz, 6 H) 2.08-2.17 (m, 2 H) 2.18-2.25 (m, 2 H) 2.77 (t, J = 6.97 Hz, 2 H) 3.29 (s, 3 H) 5.13 (quin, J = 6.85 Hz, 1 H) 6.54 (d, J = 9.41 Hz, 1 H) 7.47 (d, J = 8.19 Hz, 1 H) 7.76-7.79 (m, 1 H) 7.81 (dd, J = 8.31, 2.08 Hz, 1 H) 7.97 (dd, J = 9.41, 2.57 Hz, 1 H) 8.21 (d, J = 2.44 Hz, 1 H) 8.26 (t, J = 2.02 Hz, 1 H) 8.84 (t, J = 2.02 Hz, 2 H). | Rt = 0.80 min (UPLC-MS); ESI-MS = 388.1 [M + 1]$^+$ (UPLC-MS) |

| Example | Intermediate | Structure 1H NMR (solvent, δ) | UPLC-MS |
|---|---|---|---|
| 40 | B20 | 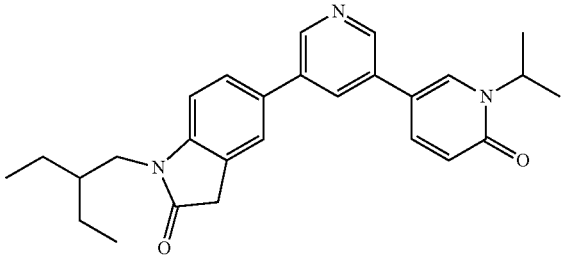<br>1-(2-ethylbutyl)-5-(1'-isopropyl-6'-oxo-1',6'-dihydro-[3,3'-bipyridin]-5-yl)indolin-1-one<br><br>(400 MHz, DMSO-$d_6$) δ ppm 0.98 (t, J = 7.40 Hz, 6 H) 1.36-1.46 (m, 4 H) 1.49 (d, J = 6.85 Hz, 6 H) 1.84 (dt, J = 12.72, 6.48 Hz, 1 H) 3.69 (d, J = 7.46 Hz, 2 H) 3.77 (s, 2 H) 5.22 (quin, J = 6.85 Hz, 1 H) 6.62 (d, J = 9.41 Hz, 1 H) 7.19 (d, J = 8.19 Hz, 1 H) 7.80-7.88 (m, 2 H) 8.04 (dd, J = 9.41, 2.57 Hz, 1 H) 8.25-8.31 (m, 2 H) 8.87 (dd, J = 7.58, 2.08 Hz, 2 H). | Rt = 1.09 min (UPLC-MS); ESI-MS = 430.1 [M + 1]$^+$ (UPLC-MS) |
| 41 | Commercial 5-Bromo-1H-pyrrolo[2,3-b]pyridin-2(3H)-one | 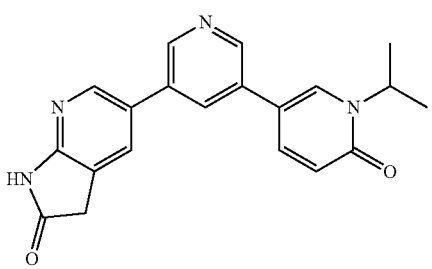<br>5-(1'-Isopropyl-6'-oxo-1',6'-dihydro-[3,3'-bipyridin]-5-yl)-1H-pyrrolo[2,3-b]pyridin-2(3H)-one<br><br>(400 MHz, DMSO-$d_6$) δ ppm 1.41 (d, J = 6.85 Hz, 6 H) 3.66 (s, 2 H) 5.13 (quin, J = 6.82 Hz, 1 H) 6.54 (d, J = 9.29 Hz, 1 H) 7.97 (dd, J = 9.41, 2.57 Hz, 1 H) 8.07 (s, 1 H) 8.20 (d, J = 2.57 Hz, 1 H) 8.26 (t, J = 2.14 Hz, 1 H) 8.56 (d, J = 1.83 Hz, 1 H) 8.84 (d, J = 2.20 Hz, 1 H) 8.81 (d, J = 2.08 Hz, 1H) 11.18 (s, 1 H). | Rt = 0.58 min (UPLC-MS); ESI-MS = 347.0 [M + 1]$^+$ (UPLC-MS) |

Example 42: 5-(2-amino-1'-isopropyl-6'-oxo-1',6'-dihydro-[3,3'-bipyridin]-5-yl)-1-methylindolin-2-one Step 42.1: 1-methyl-5-(4,4,5,5-tetramethyl-1,3,2-dioxaborolan-2-yl)indolin-2-one

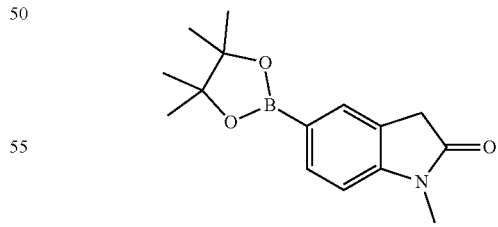

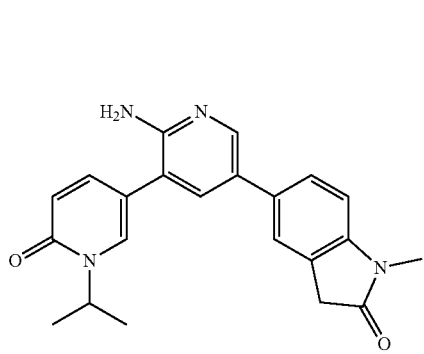 [SMILES: CC(C)n1cc(-c2cc(-c3ccc4c(c3)CC(=O)N4C)cnc2N)ccc1=O]

A mixture of 5-bromo-1-methyl-2-oxoindoline (500 mg, 2.212 mmol), Bis(pinacolato)diboron (730 mg, 2.88 mmol), KOAc (651 mg, 6.64 mmol) and PdCl$_2$(dppf).CH$_2$Cl$_2$ complex (81 mg, 0.111 mmol) in Dioxane (8.32 mL) was stirred at 115° C. for 20 min. The reaction mixture was cooled down to RT, filtered through a pad of Celite and the filtrate was concentrated under reduced pressure. EtOAc and saturated aqueous NaHCO$_3$ solution were added and both phases were separated. The organic phase was washed twice with brine, dried over MgSO$_4$, filtered and concentrated under reduced pressure to afford the title product (1.04 g, 2.208 mmol, quantitative yield) as brown solid. Rt=1.917 min (LC-MS); ESI-MS=274.1 [M+1]$^+$ (LC-MS).

Step 42.2

2'-amino-5'-bromo-1-isopropyl-[3,3'-bipyridin]-6(1H)-one

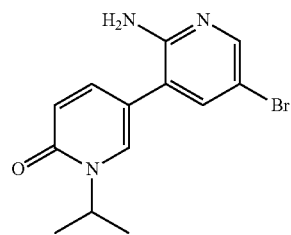 [SMILES: CC(C)n1cc(-c2cc(Br)cnc2N)ccc1=O]

The title compound was prepared in analogy to the procedure described for intermediate 2 using 1-isopropyl-5-(4,4,5,5-tetramethyl-1,3,2-dioxaborolan-2-yl)pyridin-2(1H)-one (intermediate A1) and 5-bromo-3-iodopyridine-2-amine. Rt=1.154 min (LC-MS); ESI-MS=310.0 [M+1]$^+$ (LC-MS).

5-(2-amino-1'-isopropyl-6'-oxo-1',6'-dihydro-[3,3'-bipyridin]-5-yl)-1-methylindolin-2-one A vial was charged with 2'-amino-5'-bromo-1-isopropyl-[3,3'-bipyridin]-6(1H)-one (Step 42.2) (150 mg, 0.341 mmol), 1-methyl-5-(4,4,5,5-tetramethyl-1,3,2-dioxaborolan-2-yl)indolin-2-one (Step 42.1) (102 mg, 0.375 mmol) in DMF (2 mL), EtOH (1.143 mL) and water (0.857 mL). K$_2$CO$_3$ (141 mg, 1.022 mmol) and Pd(PPh$_3$)$_2$Cl$_2$ (23.91 mg, 0.034 mmol) were added, the vial was sealed, flushed with nitrogen and the resulting mixture was heated up and stirred 10 min at 80° C. The reaction mixture was diluted with EtOAc (15 mL) and passed through a pad of Na$_2$SO$_4$ and the pad was washed with MeOH. The resulting filtrate was concentrated under reduced pressure. The crude product was purified by preparative HPLC (gradient 5% to 50% ACN in 20 min) followed by basic workup to afford the title product (27.4 mg, 0.072 mmol, 21.1% yield) as pale yellow solid. Rt=1.275 min (LC-MS); ESI-MS=375.1 [M+1]$^+$ (LC-MS). $^1$H NMR (400 MHz, DMSO-d$_6$) δ ppm 1.35 (d, J=6.85 Hz, 6H) 3.15 (s, 3H) 3.59 (s, 2H) 5.08 (quin, J=6.77 Hz, 1H) 5.77 (s, 2H) 6.47 (d, J=9.29 Hz, 1H) 7.03 (d, J=8.44 Hz, 1H) 7.51-7.58 (m, 4H) 7.82 (d, J=2.20 Hz, 1H) 8.23 (d, J=2.32 Hz, 1H).

Example 43: 5-(5-amino-6-(1-isopropyl-6-oxo-1,6-dihydropyridin-3-yl)pyrazin-2-yl)-1-methylindolin-2-one

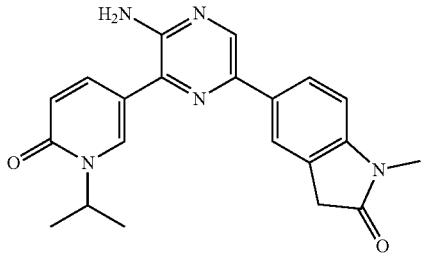 [SMILES: CC(C)n1cc(-c2nc(-c3ccc4c(c3)CC(=O)N4C)cnc2N)ccc1=O]

Step 43.1: 5-(5-amino-6-chloropyrazin-2-yl)-1-methylindolin-2-one

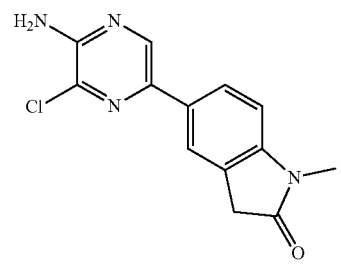 [SMILES: CN1C(=O)Cc2cc(-c3cnc(N)c(Cl)n3)ccc21]

The title compound was prepared in analogy to the procedure described for Example 42 using 5-bromo-3-chloropyrazin-2-amine and 1-methyl-5-(4,4,5,5-tetramethyl-1,3,2-dioxaborolan-2-yl)indolin-2-one (Step 1.1—intermediate 1—method A). The crude product obtained after workup was triturated with ACN and filtrated off to afford a solid. Rt=0.74 min (LC-MS); ESI-MS=275.0 [M+1]$^+$ (LC-MS).

5-(5-amino-6-(1-isopropyl-6-oxo-1,6-dihydropyridin-3-yl)pyrazin-2-yl)-1-methylindolin-2-one A flask was charged with 5-(5-amino-6-chloropyrazin-2-yl)-1-methylindolin-2-one (Step 43.1) (120 mg, 0.393 mmol), 1-isopropyl-5-(4,4,5,5-tetramethyl-1,3,2-dioxaborolan-2-yl)pyridin-2(1H)-one (Intermediate A1) (191 mg, 0.472 mmol) and Cs$_2$CO$_3$ (256 mg, 0.786 mmol) in DME (2 mL) and water (0.2 mL). PdCl$_2$(dppf).CH$_2$Cl$_2$ complex (32.1 mg, 0.039 mmol) was added and the resulting mixture was heated up and stirred at 80° C. for 2 hr. The reaction mixture was filtered. The resulting cake was dissolved in CH$_2$Cl$_2$ and washed with an aqueous NaHCO$_3$ solution and brine. The organic layer was dried over MgSO$_4$, filtered and concentrated under reduced pressure. The crude product was first triturated with ACN and the resulting solid was filtrated off and washed with ACN. The solid was triturated with MeOH, filtrated off and washed with MeOH. The cake was purified by silica gel column chromatography (CH$_2$Cl$_2$/MeOH 0-20% MeOH), triturated with ACN to afford the title product (22.5 mg, 0.057 mmol, 14.5% yield). Rt=0.71 min (LC-MS); ESI-MS=376.1 [M+1]$^+$ (LC-MS). $^1$H NMR (400 MHz, DMSO-d$_6$) δ ppm 1.37 (d, J=6.70 Hz, 6H) 3.15 (s, 3H) 3.62 (s, 2H) 5.05 (quin, J=6.77 Hz, 1H) 6.30 (s, 2H)

6.54 (d, J=9.4 Hz, 1H) 7.05 (d, J=8.2 Hz, 1H) 7.84 (dd, J=9.2, 2.4 Hz, 1H) 7.90-7.95 (m, 2H) 8.16 (d, J=2.16 Hz, 1H) 8.48 (s, 1H).

Example 44: 5-(5-(1-isopropyl-6-oxo-1,6-dihydropyridazin-3-yl)pyridin-3-yl)-1-methylindolin-2-one

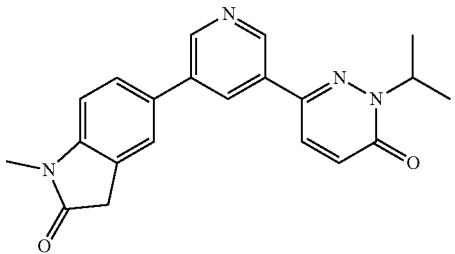 [SMILES: CC(C)n1nc(-c2cncc(-c3ccc4c(c3)CC(=O)N4C)c2)ccc1=O]

Step 44.1: 6-bromopyridazin-3(2H)-one

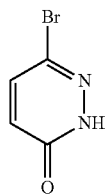

A MW vial was charged with 3,6-dibromopyridazine (383 mg, 1.610 mmol) and 4N NaOH (2.415 mL, 9.66 mmol). The MW vial was sealed and the resulting mixture was heated up and stirred at 100° C. for 2 hr. The mixture was cooled down to 0° C. and AcOH was added. The product was extracted 4 times with CH$_2$Cl$_2$. The combined organic layers were washed with water, 2N NaOH and 2N HCl, dried over MgSO$_4$, filtered and concentrated under reduced pressure to afford the title product (398 mg, 1.592 mmol, 99% yield) as colorless oil. Rt=0.39 min (LC-MS); ESI-MS=174.9/177.1 [M+1]$^+$ (LC-MS).

Step 44.2: 6-bromo-2-isopropylpyridazin-3(2H)-one

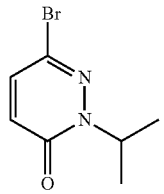

The title product was prepared in analogy to the procedure described in Step A1.1 (intermediate A1—method A) using 6-bromopyridazin-3(2H)-one (Step 44.1) at 80° C. for 2 hr to afford a yellow oil. Rt=0.81 min (LC-MS); ESI-MS=216.9/218.9 [M+1]$^+$ (LC-MS).

Step 44.3: (1-isopropyl-6-oxo-1,6-dihydropyridazin-3-yl)boronic acid

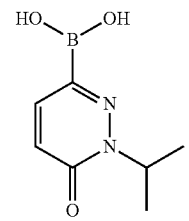

The title product was prepared in analogy to the procedure described in Intermediate A1 (method A) using 6-bromo-2-isopropylpyridazin-3(2H)-one (Step 44.2) to afford a dark solid. Rt=0.44 min (LC-MS); ESI-MS=183.1 [M+1]$^+$ (LC-MS).

Step 44.4: 5-(5-(1-isopropyl-6-oxo-1,6-dihydropyridazin-3-yl)pyridin-3-yl)-1-methylindolin-2-one The title product was prepared in analogy to the procedure described for Example 1 (method A) using 5-(5-bromopyridin-3-yl)-1-methylindolin-2-one (Intermediate 1—method A) and (1-isopropyl-6-oxo-1,6-dihydropyridazin-3-yl)boronic acid (Step 44.3) at 90° C. for 1 hr. No workup was done, the reaction mixture was diluted with MeOH, passed through a Silica-Thiol cartridge and the resulting filtrate was concentrated under reduced pressure. The crude product was purified by silica gel column chromatography (CH$_2$Cl$_2$/0-20% MeOH) followed by precipitation in MeOH to afford the title product as white solid. Rt=0.80 min (LC-MS); ESI-MS=361.2 [M+1]$^+$ (LC-MS). $^1$H NMR (400 MHz, DMSO-d$_6$) δ ppm 1.36 (d, J=6.60 Hz, 6H) 3.16 (s, 3H) 3.64 (s, 2H) 5.05 (quin, J=6.30 Hz, 1H) 7.07 (d, J=9.7 Hz, 1H) 7.12 (d, J=8.6 Hz, 1H) 7.76 (m, 2H) 8.21 (d, J=9.8 Hz, 1H) 8.43 (m, 1H) 8.91 (s, 1H) 9.04 (s, 1H).

Example 45: 1-(2-hydroxyethyl)-5-(1'-isopropyl-6'-oxo-1',6'-dihydro-[3,3'-bipyridin]-5-yl)indolin-2-one

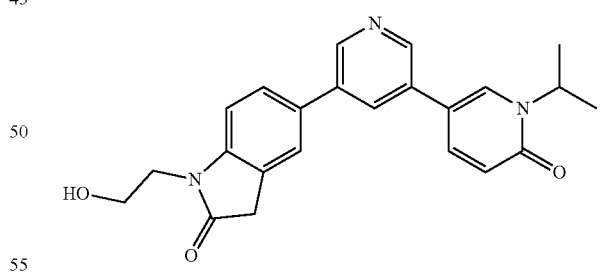

5-(1'-Isopropyl-6'-oxo-1',6'-dihydro-[3,3'-bipyridin]-5-yl)-1-(2-methoxyethyl)indolin-2-one (Example 29) (32 mg, 0.079 mmol) was dissolved in DCM (500 μL) and the resulting solution was cooled down to 5° C. with an ice bath. BBr$_3$ 1M in DCM (87 μL, 0.087 mmol) was added and the reaction mixture was allowed to warm up and stir at RT for 2 hr. The reaction mixture was quenched with MeOH and concentrated under reduced pressure. The crude product was purified by preparative HPLC (5-100% ACN in 20 min). The desired fractions were combined, basified with 10% NaHCO$_3$ solution and extracted three times with CH$_2$Cl$_2$/ iPrOH 9/1 using a Biotage Phase Separator cartridge. The filtrate was concentrated under reduced pressure to afford the title product (19 mg, 0.046 mmol, 58.4% yield) as off-white solid. Rt=0.64 min (LC-MS); ESI-MS=390.1 [M+1]+ (LC-MS). 1H NMR (400 MHz, DMSO-d6) δ ppm 1.41 (d, J=6.85 Hz, 6H) 3.49-3.56 (m, 2H) 3.62 (s, 2H) 3.75 (t, J=5.50 Hz, 2H) 4.86 (t, J=5.50 Hz, 1H) 5.13 (quin, J=6.85 Hz, 1H) 6.52 (d, J=9.41 Hz, 1H) 7.20 (d, J=8.07 Hz, 1H) 7.72-7.78 (m, 2H) 7.97 (dd, J=9.41, 2.57 Hz, 1H) 8.17-8.21 (m, 2H) 8.79 (dd, J=5.26, 2.08 Hz, 2H).

Example 46: 5-(6-(1-isopropyl-6-oxo-1,6-dihydro-pyridin-3-yl)pyrazin-2-yl)-1-methylindolin-2-one

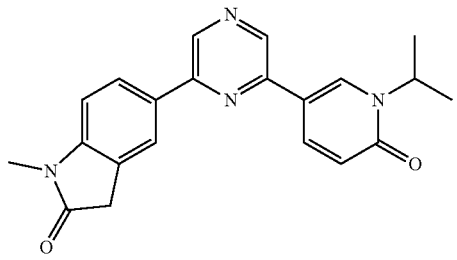 [SMILES: CC(C)n1cc(-c2cncc(-c3ccc4c(c3)CC(=O)N4C)n2)ccc1=O]

Step 46.1: 5-(6-bromopyrazin-2-yl)-1-isopropylpyridin-2(1H)-one

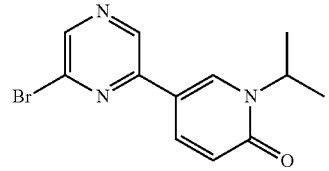 [SMILES: CC(C)n1cc(-c2cncc(Br)n2)ccc1=O]

In a MW vial under N2, 2,6-dibromopyrazine (300 mg, 1.261 mmol) was dissolved in DME (4 mL). 1-isopropyl-5-(4,4,5,5-tetramethyl-1,3,2-dioxaborolan-2-yl)pyridin-2(1H)-one (Intermediate A1—method A) (365 mg, 1.387 mmol), Cs2CO3 (822 mg, 2.52 mmol) and PdCl2(dppf) (46.1 mg, 0.063 mmol) were added at RT, followed by water (0.67 mL). The MW vial was sealed and the reaction mixture was heated up and stirred at 90° C. for 2 hr. The mixture was filtered through a pad of celite and the resulting filtrate was concentrated under reduced pressure. The mixture was partitioned between a saturated aqueous NaHCO3 solution and EtOAc and both phases separated. The aqueous layer was extracted with EtOAc. The combined organic layers were washed with brine, dried over MgSO4, filtered and concentrated under reduced pressure. The crude product was purified by silica gel column chromatography (CH2Cl2/0-20% MeOH) to afford the title product (182 mg, 0.619 mmol, 49.1% yield) as brown solid. Rt=0.86 min (LC-MS); ESI-MS=293.9/296.0 [M+1]+ (L C-MS).

5-(6-(1-isopropyl-6-oxo-1,6-dihydropyridin-3-yl)pyrazin-2-yl)-1-methylindolin-2-one The title product was prepared in analogy to the procedure described in Example 1 (method A) using 5-(6-bromopyrazin-2-yl)-1-isopropylpyridin-2(1H)-one (Step 46.1) and 1-methyl-5-(4,4,5,5-tetramethyl-1,3,2-dioxaborolan-2-yl)indolin-2-on (Step 1.1—intermediate 1—method A). The crude product was purified by silica gel column chromatography (CH2Cl2/0-20% MeOH) followed by precipitation in MeOH to afford a white solid. Rt=0.79 min (LC-MS); ESI-MS=361.2 [M+1]+ (LC-MS). 1H NMR (400 MHz, DMSO-d6) δ ppm 1.43 (d, J=6.70 Hz, 6H) 3.20 (s, 3H) 3.69 (s, 2H) 5.14 (quin, J=6.70 Hz, 1H) 6.60 (d, J=9.5 Hz, 1H) 7.16 (d, J=8.2 Hz, 1H) 8.21 (m, 2H) 8.31 (m, 1H) 8.58 (s, 1H) 9.09 (s, 1H) 9.13 (s, 1H).

Example 47: 1-(3-hydroxypropyl)-5-(1'-isopropyl-6'-oxo-1',6'-dihydro-[3,3'-bipyridin]-5-yl)indolin-2-one

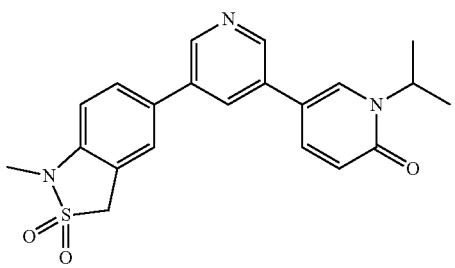 [SMILES: CC(C)n1cc(-c2cncc(-c3ccc4c(c3)CS(=O)(=O)N4C)c2)ccc1=O]

The title product was prepared in analogy to the procedure described in Example 45 using 5-(1'-isopropyl-6'-oxo-1',6'-dihydro-[3,3'-bipyridin]-5-yl)-1-(3-methoxypropyl)indolin-2-one (Example 30) to afford a colorless oil. Rt=0.70 min (UPLC-MS); ESI-MS=404.1 [M+1]+ (UPLC-MS). 1H NMR (400 MHz, DMSO-d6) δ ppm 1.41 (d, J=6.85 Hz, 6H) 1.74 (quin, J=5.50 Hz, 2H) 3.42-3.50 (m, 2H) 3.66 (s, 2H) 3.75 (t, J=5.50 Hz, 2H) 4.60 (t, J=5.50 Hz, 1H) 5.12 (quin, J=6.85 Hz, 1H) 6.53 (d, J=9.41 Hz, 1H) 7.18 (d, J=8.07 Hz, 1H) 7.74-7.78 (m, 2H) 7.95 (dd, J=9.41, 2.57 Hz, 1H) 8.17-8.23 (m, 2H) 8.79 (dd, J=5.26, 2.08 Hz, 2H).

Example 48: 1-isopropyl-5'-(1-methyl-2,2-dioxido-1,3-dihydrobenzo[c]isothiazol-5-yl)-[3,3'-bipyridin]-6(1H)-one The title compound was prepared in analogy to the procedure described in Example 20 using Intermediate 2 and Intermediate B21 described above.

Rt=0.83 min (UPLC-MS); ESI-MS=396.1 [M+1]+ (UPLC-MS); 1H NMR: (400 MHz, DMSO-d6) δ ppm 1.38 (d, J=6.6 Hz, 6H) 3.09 (s, 3H) 4.72 (s, 2H) 5.1 (m, 1H) 6.51 (d, J=9.4 Hz, 1H) 7.09 (d, J=8.2 Hz, 1H) 7.83 (m, 2H) 7.93 (dd, J=9.6 Hz, 2.5 Hz, 1H) 8.16-8.18 (m, 2H), 8.76 (d, J=2.3 Hz, 1H) 8.79 (d, J=2.3 Hz, 1H).

Example 49: 5'-(1-ethyl-2,2-dioxido-1,3-dihydrobenzo[c]isothiazol-5-yl)-1-isopropyl-[3,3'-bipyridin]-6(1H)-one

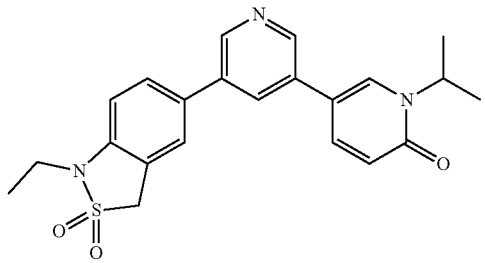 [SMILES: CCN1c2ccc(-c3cncc(-c4ccc(=O)n(C(C)C)c4)c3)cc2CS1(=O)=O]

The title compound was prepared in analogy to the procedure described in Example 35 using Intermediate 3 and Intermediate C1. Rt=0.88 min (UPLC-MS); ESI-MS=410.2 [M+1]⁺ (UPLC-MS); ¹H NMR (400 MHz, DMSO-d₆) δ ppm 1.32 (t, J=7.1 Hz, 3H) 1.41 (d, J=6.8 Hz, 6H) 3.80-3.67 (m, 2H) 4.74 (s, 2H) 5.14 (p, J=6.9 Hz, 1H) 6.56 (d, J=9.5 Hz, 1H) 7.17 (d, J=8.9 Hz, 1H) 7.92-7.84 (m, 2H) 7.99 (dd, J=9.5, 2.7 Hz, 1H) 8.26 (d, J=2.7 Hz, 1H) 8.44 (s, 1H) 8.90 (dd, J=14.1, 2.1 Hz, 2H)

Example 50: 5'-(1-isobutyl-2,2-dioxido-1,3-dihydrobenzo[c]isothiazol-5-yl)-1-isopropyl-[3,3'-bipyridin]-6(1H)-one

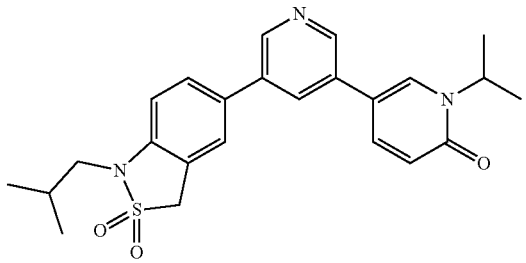 [SMILES: CC(C)CN1c2ccc(-c3cncc(-c4ccc(=O)n(C(C)C)c4)c3)cc2CS1(=O)=O]

The title compound was prepared in analogy to the procedure described in Example 35 using Intermediate 3 and Intermediate C2. Rt=1.02 min (UPLC-MS); ESI-MS=439.2 [M+1]⁺ (UPLC-MS); ¹H NMR (400 MHz, DMSO-d₆) δ ppm 1.01 (d, J=6.6 Hz, 6H) 1.41 (d, J=6.8 Hz, 6H) 2.15-2.03 (m, 1H) 3.40 (d, J=7.3 Hz, 2H) 4.76 (s, 2H) 5.13 (p, J=6.9 Hz, 1H) 6.56 (d, J=9.4 Hz, 1H) 7.15 (d, J=8.2 Hz, 1H) 7.87-7.82 (m, 2H) 7.98 (dd, J=9.5, 2.7 Hz, 1H) 8.24 (d, J=2.6 Hz, 1H) 8.37 (s, 1H) 8.87 (dd, J=16.6, 2.1 Hz, 2H).

Example 51: 5'-(1-(cyclobutylmethyl)-2,2-dioxido-1,3-dihydrobenzo[c]isothiazol-5-yl)-1-isopropyl-[3,3'-bipyridin]-6(1H)-one

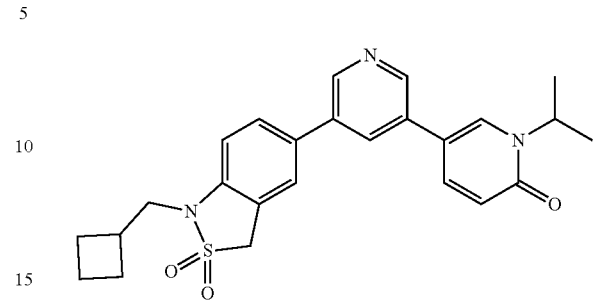

The title compound was prepared in analogy to the procedure described in Example 35 using Intermediate 3 and Intermediate C3. Rt=1.05 min (UPLC-MS); ESI-MS=450.2 [M+1]⁺ (UPLC-MS); ¹H NMR (400 MHz, DMSO-d₆) δ ppm 1.41 (d, J=6.8 Hz, 6H) 1.86 (q, J=4.1, 3.2 Hz, 4H) 2.04 (dd, J=9.4, 4.8 Hz, 2H) 2.77-2.79 (m, 1H) 3.63 (d, J=7.0 Hz, 2H) 4.75 (s, 2H) 5.13 (p, J=6.9 Hz, 1H) 6.56 (d, J=9.4 Hz, 1H) 7.14 (d, J=8.8 Hz, 1H) 7.86 (d, J=7.4 Hz, 2H) 7.99 (dd, J=9.5, 2.6 Hz, 1H) 8.25 (d, J=2.7 Hz, 1H) 8.41 (s, 1H) 8.88 (dd, J=16.6, 2.1 Hz, 2H)

Example 52: 5-(4-fluoro-1'-isopropyl-6'-oxo-1',6'-dihydro-[3,3'-bipyridin]-5-yl)-1-methylindolin-2-one

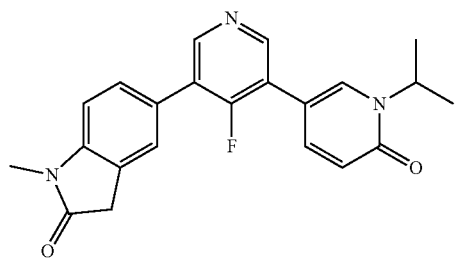 [SMILES: CC(C)n1cc(-c2cncc(-c3ccc4c(c3)CC(=O)N4C)c2F)ccc1=O]

Step 52.1: 5'-bromo-4'-fluoro-1-isopropyl-[3,3'-bipyridin]-6(1H)-one

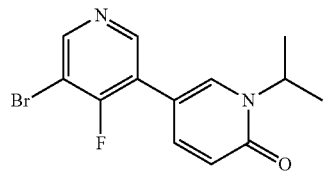 [SMILES: CC(C)n1cc(-c2cncc(Br)c2F)ccc1=O]

The title product was prepared in analogy to the procedure described in Step 46.1 using 3,5-dibromo-4-fluoropyridine and 1-isopropyl-5-(4,4,5,5-tetramethyl-1,3,2-dioxaborolan-2-yl)pyridin-2(1H)-one (Intermediate A1—method A). Rt=0.84 min (UPLC-MS); ESI-MS=311.0/313.0 [M+1]+ (UPLC-MS)

5-(4-fluoro-1'-isopropyl-6'-oxo-1',6'-dihydro-[3,3'-bipyridin]-5-yl)-1-methylindolin-2-one The title product was prepared in analogy to the procedure described in Example 46 using 5'-bromo-4'-fluoro-1-isopropyl-[3,3'-bipyridin]-6(1H)-one (Step 52.1) and 1-methyl-5-(4,4,5,5-tetramethyl-1,3,2-dioxaborolan-2-yl)indolin-2-one (Step 1.1—intermediate 1—method A). Rt=0.77 min (UPLC-MS); ESI-MS=378.2 [M+1]⁺ (UPLC-MS). $^1$H NMR (400 MHz, DMSO-d$_6$) δ ppm 1.37 (d, J=6.8 Hz, 6H) 3.18 (s, 3H) 3.65 (s, 2H) 5.12 (p, J=6.8 Hz, 1H) 6.53 (d, J=9.4 Hz, 1H) 7.15 (d, J=8.2 Hz, 1H) 7.59 (d, J=7.6 Hz, 2H) 7.77-7.68 (m, 1H) 8.08 (dd, J=5.6, 2.5 Hz, 1H) 8.66 (dd, J=14.6, 9.5 Hz, 2H).

Biochemical Assays (Examples 53 and 54)

For all biochemical assays, human recombinant proteins were expressed in and purified from baculo virus transfected insect cells. The constructs comprised the GS-domain and kinase domain of wild-type ALK2 (aa172-499), ALK2 FOP mutant (aa172-499 R206H), ALK3 (aa198-525), ALK5 (aa162-503) and ALK6 (aa168-495).

Example 53: In Vitro Enzyme Inhibition Using a Biochemical Autophosphorylation Assay (Luminescence-Based ADPGlo Kinase Activity Assay)—"ADPGlo Assay"

A kinase selectivity panel which measures autophosphorylation using the ADP-Glo™ Kinase Assay (Promega, V9101) was set-up for wild-type ALK2 (aa172-499) and ALK3 (aa198-525).

The assays were performed in 384-well, low volume microtiter assay plates in a final reaction volume of 6 ul. Dose-response curves were generated by incubating 10 nM of each kinase in 50 mM Hepes pH 7.5, 0.02% Tween 20, 0.02% BSA, 1 mM DTT, 10 uM Na$_3$VO$_4$, 10 mM ß-Glycerolphosphate, 1 mM MgCl$_2$, 12 mM MnCl$_2$ and 15 uM ATP for 60 min at 32° C. in the presence or absence of compound diluted in DMS. The amount of generated ADP is a measure of kinase activity and is quantified using the ADP-Glo™ Kinase Assay (Promega) according to manufacturer's instructions. ADP is converted to ATP by adding 3 ul of ADP-Glo™ Reagent and incubation at 32° C. for 60 min. ATP is subsequently converted into a bioluminescent signal by adding 6 ul luciferase assay reagents (Kinase detection buffer+Kinase Detection Substrate (Promega)) and further incubation at 32° C. for 60 min. For the measurement of luminescence a PHERAstar™ Multilabel Reader was used at a measurement interval time of 0.1 second (optical module for luminescence measurements in the 230 nm to 750 nm wavelength range). The luminescent signal positively correlates with kinase activity.

IC$_{50}$ values for a given antagonist correspond to the compound concentration needed to inhibit half of the maximum signal of the kinase reaction.

Specific activities are shown in the table below.

| Ex. | ALK2 ADPGlo IC$_{50}$ [umol l$^{-1}$] | ALK3 ADPGlo IC$_{50}$ [umol l$^{-1}$] |
|---|---|---|
| 1 | 0.11 | 0.52 |
| 2 | 0.087 | 0.52 |
| 3 | 0.097 | 0.5 |
| 4 | 1.3 | 13.7 |
| 5 | 0.14 | 1.5 |
| 6 | 0.23 | 3.6 |
| 7 | 0.23 | 2 |
| 8 | 0.2 | 2.4 |
| 9 | 0.49 | 2.5 |
| 10 | 0.71 | 2 |
| 11 | 0.6 | 7.9 |
| 12 | 1.5 | >15.1 |
| 13 | 0.68 | 8.5 |
| 14 | 0.74 | 9.9 |
| 15 | 0.88 | 9.9 |
| 16 | 1.1 | 15 |
| 17 | 1.1 | >15.1 |
| 18 | 1 | >15.1 |
| 19 | 2.2 | 5.4 |
| 20 | 0.11 | 0.62 |
| 21 | 0.064 | 0.57 |
| 22 | 0.725 | 4.2 |
| 23 | 1.2 | 5.8 |
| 24 | 0.067 | 0.3 |
| 25 | 0.1 | 0.49 |
| 26 | 0.71 | 4.3 |
| 27 | 1.7 | 9.6 |
| 28 | 0.031 | 0.18 |
| 29 | 0.14 | 2.5 |
| 30 | 0.13 | 0.45 |
| 31 | 0.12 | 0.52 |
| 32 | 0.075 | 0.51 |
| 33 | 0.18 | 0.92 |
| 34 | 0.3 | 1.8 |
| 35 | 0.11 | 0.7 |
| 36 | 0.35 | 2.4 |
| 37 | 0.29 | 2.5 |
| 38 | 0.13 | 0.54 |
| 39 | 0.089 | 0.4 |
| 40 | 0.094 | 0.8 |
| 41 | 0.49 | 6.3 |
| 42 | 0.46 | 3.4 |
| 43 | 0.09 | 0.6 |
| 44 | 0.11 | 1 |
| 45 | 0.16 | 1.1 |
| 46 | 0.15 | 0.93 |
| 47 | 0.175 | 1.12 |
| 48 | 0.071 | 0.283 |
| 49 | 0.13 | 0.67 |
| 50 | 0.11 | 0.93 |
| 51 | 0.16 | 0.88 |
| 52 | 0.69 | 8.7 |

The table above shows that the compounds of the invention are selective ALK-2 inhibitors over ALK-3.

Example 54: In Vitro Enzyme Inhibition Using a Biochemical Peptide Phosphorylation Assay—"Caliper Assay"

A kinase selectivity panel which measures substrate peptide phosphorylation was set-up for wild-type ALK2 (aa172-499), ALK2 FOP mutant (aa172-499 R206H), ALK1 (aa166-493), ALK5 (aa162-503) and ALK6 (aa168-495). The technology used for the described assay is based on the separation and quantification of substrate and product in an electrical field. In the course of the kinase reaction the peptide substrate is phosphorylated by a kinase. The transfer of a phosphate residue also causes the introduction of two additional negative charges and hence to a change in the net charge of the phospho-peptide compared to the unphosphorylated peptide. Due to this difference in charge the phosphorylated und unphosphorylated peptides migrate with different velocities in an electrical field.

In the applied method, this separation takes place inside a chip that contains a complex capillary system for simultaneous analysis of 12 samples ("LabChip EZ Reader 12-sipper chip", Caliper Technologies Corp., Mountain View, USA). In order to allow the detection and quantification of the peptides in the capillary system, the peptides carry a fluorescent label (fluorescein). With this label the peptides can be quantified by fluorescence intensity through the instruments laser and detection system (LC3000, Caliper Life Sciences).

The assays were performed in 384-well, low volume microtiter assay plates in a final reaction volume of 9 ul. Dose-response curves were generated by incubating 10 nM of each kinase together with 2 uM of the fluorescently labeled substrate peptide 5-Fluo-Ahx-KKYQAEEN-T-YDEYENKK-amid (10 mM stock solution in DMSO) in 50 mM Hepes pH 7.5, 0.02% Tween 20, 0.02% BSA, 1 mM DTT, 10 uM $Na_3VO_4$, 10 mM ß-Glycerolphosphate, 1 mM $MgCl_2$, 12 mM $MnCl_2$ (ALK1 and ALK6 7 mM) and 15 uM ATP for 60 min at 30° C. in the presence or absence of compound diluted in DMSO.

Kinase reactions were terminated by adding 15 ul STOP buffer (100 mM HEPES pH 7.5, 5% DMSO, 0.1% Caliper coating reagent, 10 mM EDTA, and 0.015% Brij35.

Plates with terminated kinase reactions were transferred to the Caliper LC3000 workstation (Caliper Technologies Corp., Mountain View, USA) for reading. The relative amount of phosphorylated peptide r, was calculated using the heights of the substrate peak, s, and the product peak, p:r=p/(p+s).

$IC_{50}$ values for a given antagonist correspond to the compound concentration needed to inhibit half of the maximum signal of the kinase reaction.

Specific activities are shown in the table below.

| Example | ALK2 ($IC_{50}$ [umol.l$^{-1}$]) | ALK2 FOP EPK ($IC_{50}$ [umol.l$^{-1}$]) | ALK1 ($IC_{50}$ [umol l$^{-1}$]) | ALK5 ($IC_{50}$ [umol.l$^{-1}$]) | ALK6 ($IC_{50}$ [umol.l$^{-1}$]) |
|---|---|---|---|---|---|
| 1 | 0.11 | 0.09 | 0.54 | 2.60 | 0.42 |
| 2 | 0.08 | 0.06 | 0.41 | 0.61 | 0.94 |
| 3 | 0.09 | 0.07 | 0.49 | 0.66 | 1.00 |
| 4 | 0.60 | 0.65 | 4.30 | >10 | 7.50 |
| 5 | 0.16 | 0.13 | 0.90 | 0.72 | 1.30 |
| 6 | 0.15 | 0.18 | 1.70 | 5.30 | 2.90 |
| 7 | 0.19 | 0.17 | 1.20 | 4.40 | 2.70 |
| 8 | 0.17 | 0.12 | 1.50 | 9.60 | 5.30 |
| 9 | 0.46 | 0.40 | 2.60 | >10 | 7.20 |
| 10 | 0.41 | 0.39 | 2.90 | >10 | 6.40 |
| 11 | 0.49 | 0.47 | 4.70 | >10 | >10 |
| 12 | 0.80 | 0.81 | 6.80 | >10 | 7.00 |
| 13 | 0.62 | 0.57 | 5.30 | >10 | >10 |
| 14 | 0.48 | 0.51 | 4.60 | 9.10 | 2.90 |
| 15 | 0.76 | 0.74 | 5.10 | >10 | >10 |
| 16 | 0.82 | 0.83 | 8.70 | >10 | >10 |
| 17 | 0.92 | 0.91 | 7.00 | >10 | >10 |
| 18 | 0.71 | 0.60 | 4.70 | >10 | >10 |
| 19 | 0.74 | 0.81 | 4.20 | >10 | 9.30 |
| 20 | 0.09 | 0.09 | 0.61 | 2.50 | 0.49 |
| 21 | 0.06 | 0.053 | 0.36 | 1.80 | 0.72 |
| 22 | 0.39 | 0.34 | 2.17 | >10 | 2.77 |
| 23 | 0.67 | 0.87 | 5.60 | >10 | 4.50 |
| 24 | 0.07 | 0.06 | 0.42 | 1.90 | 0.80 |
| 25 | 0.08 | 0.07 | 0.54 | 1.50 | 1.00 |
| 26 | 0.47 | 0.59 | 4.30 | >10 | 3.60 |
| 27 | 0.88 | 1.20 | >10 | >10 | >10 |
| 28 | 0.03 | 0.02 | 0.13 | 0.58 | 0.16 |
| 29 | 0.13 | 0.15 | 1.60 | 6.80 | 1.60 |
| 30 | 0.12 | 0.13 | 1.50 | 6.00 | 2.60 |
| 31 | 0.10 | 0.09 | 0.77 | 5.30 | 1.40 |
| 32 | 0.07 | 0.05 | 0.28 | 0.69 | 0.50 |
| 33 | 0.17 | 0.15 | 0.76 | 2.70 | 1.80 |
| 34 | 0.18 | 0.17 | 1.10 | 3.40 | 2.10 |
| 35 | 0.1 | 0.091 | 0.63 | 5.7 | 1.8 |
| 36 | 0.19 | 0.23 | 1.30 | 9.30 | 2.90 |
| 37 | 0.24 | 0.24 | 1.70 | >10 | 5.40 |
| 38 | 0.06 | 0.06 | 0.64 | 3.40 | 1.10 |
| 39 | 0.07 | 0.06 | 0.35 | 1.40 | 0.39 |
| 40 | 0.10 | 0.08 | 0.90 | 4.20 | 0.86 |
| 41 | 0.47 | 0.71 | 6.40 | >10 | >10 |
| 42 | 0.19 | 0.15 | 1.40 | 5.60 | 3.75 |
| 43 | 0.10 | 0.09 | 0.52 | 1.00 | 2.00 |
| 44 | 0.09 | 0.08 | 0.67 | 5.70 | 3.05 |
| 45 | 0.12 | 0.10 | 0.89 | 5.00 | 1.25 |
| 46 | 0.12 | 0.11 | 0.62 | 5.00 | 2.50 |
| 47 | 0.14 | 0.15 | 1.10 | 4.20 | 1.50 |
| 48 | 0.06 | 0.06 | 0.21 | 2.40 | 1.00 |
| 49 | 0.14 | 0.13 | 0.57 | 2.90 | 1.10 |
| 50 | 0.16 | 0.14 | 0.69 | 2.40 | 1.20 |
| 51 | 0.16 | 0.15 | 0.78 | 2.70 | 1.50 |
| 52 | 0.38 | 0.38 | 3.60 | >10 | 4.70 |

The table above shows that compounds of the invention selectively inhibit ALK-2 (wild-type) and ALK-2 FOP when compared to ALK-1, ALK-5 and ALK-6.

The compound 5-(1'-isopropyl-6'-oxo-1',6'-dihydro-[3,3'-bipyridin]-5-yl)-1,3,3-trimethyl-1H-pyrrolo[2,3-b]pyridin-2(3H)-one has an $IC_{50}$>1 µM in the ALK2 and ALK2-FOP assays described above.

In one embodiment, the invention relates to a compound of formula (I) as defined herein which is not 5-(1'-isopropyl-6'-oxo-1',6'-dihydro-[3,3'-bipyridin]-5-yl)-1,3,3-trimethyl-1H-pyrrolo[2,3-b]pyridin-2(3H)-one.

Example 55: BMP (Bone Morphogenic Protein) Signaling Reporter Gene Assay

A human liver hepatocellular carcinoma cell line (HuH7) stably transfected with a reporter plasmid consisting of the human BMP response element (BRE) from the Id1 promoter fused to a luciferase reporter gene was generated through lentiviral transduction.

Cells were maintained in DMEM (GIBCO #41965 high glucose plus L-Glutamine), 10% FCS (Amimed #2-01F10-I), 1% Pen/Strp (Amimed #4-01F00) and 5 ug/ml Blasticidin (InvivoGen #ant-bl-1) at 37° C., 5% $CO_2$. Assays were performed in 384-well flat bottom polystyrene microtiter plates (cell culture treated) with sterile lids. The cells were starved through medium exchange in Blasticidine- and FCS-free medium 16 h before the assay. Prior to the assay, cells were detached from the stock flask using trypsin/EDTA and counted. A cell suspension in the same medium without Blasticidin and FCS was prepared. $2 \times 10^4$ cells in a total volume of 40 ul were added to each well of a plate already containing serial dilutions of each compound in DMSO (final DMSO concentration 0.5%). Cells and compound are incubated for 1 h at 37° C., 5% $CO_2$ before stimulation with 5 ul/well recombinant BMP6 (R&D Systems #507-BP/CF) at a final concentration of 100 ng/ml. Assay plates are incubated for another 5 hours at 37° C., 5% $CO_2$ before luciferase levels are measured.

The amount of expressed luciferase is quantified using the Steady-Glo® Luciferase Assay System (Promega #E2520). 5 ul of the Steady-Glo® Reagent are added to each well, the samples were mixed through vigorous shaking of the plate before measuring the luminesecence in a PHERAstar™ Multilabel Reader for 1 second/well (optical module for luminescence measurements in the 230 nm to 750 nm wavelength range).

IC$_{50}$ values for a given antagonist correspond to the compound concentration needed to inhibit half of the maximum signal generated by the added agonist BMP6 (100 ng/ml). Further specific activities of the compounds of the invention are described in the table below.

| Ex. | MSD HuH7 cell BMP reporter IC$_{50}$ [umol l$^{-1}$] |
|---|---|
| 1 | 0.13 |
| 2 | 0.05 |
| 3 | 0.05 |
| 4 | 1.05 |
| 5 | 0.06 |
| 6 | 0.66 |
| 7 | 0.21 |
| 8 | 0.15 |
| 9 | 0.54 |
| 10 | 0.73 |
| 11 | 0.64 |
| 12 | 0.80 |
| 13 | 0.79 |
| 14 | 0.68 |
| 15 | 1.50 |
| 16 | 1.20 |
| 17 | 1.20 |
| 18 | 0.42 |
| 19 | 1.90 |
| 20 | 0.14 |
| 21 | 0.06 |
| 22 | 0.54 |
| 23 | 1.20 |
| 24 | 0.06 |
| 25 | 0.09 |
| 26 | 0.70 |
| 27 | 2.35 |
| 28 | 0.04 |
| 29 | 0.24 |
| 30 | 0.13 |
| 31 | 0.13 |
| 32 | 0.07 |
| 33 | 0.33 |
| 34 | 0.19 |
| 35 | 0.14 |
| 36 | 0.39 |
| 37 | 0.30 |
| 38 | 0.10 |
| 39 | 0.11 |
| 40 | 0.10 |
| 41 | 0.63 |
| 42 | 0.31 |
| 43 | 0.12 |
| 44 | 0.23 |
| 45 | 0.21 |
| 46 | 0.13 |
| 47 | 0.28 |
| 48 | 0.083 |

The table above shows that the compounds of the invention may be useful for the treatment of heterotopic ossification.

Example 56: Compound a (Compound of Example 1) Prevents Turpentine Oil-Induced Increase in Serum Hepcidin Concentration in Rats To determine whether compound A is able to prevent acute rising of serum hepcidin concentration during the acute-phase reaction elicited by a single subcutaneous (sc.) injection of turpentine oil (TO), compound A was applied (3 or 10 mg/kg) or vehicle (sodium carboxymethyl cellulose: water:Tween 80, 0.5:99:0.5) orally (p. o.) at 5 mL/kg to male Sprague Dawley rats (n=8 rats per group; body weight range: 300-360 g) one hour prior to sc. injection of 1 mL/kg TO. Rats were housed in groups of two animals per cage at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. Measurements of serum hepcidin concentration were performed using a custom-made LC-MRM assay.

Figure 4:
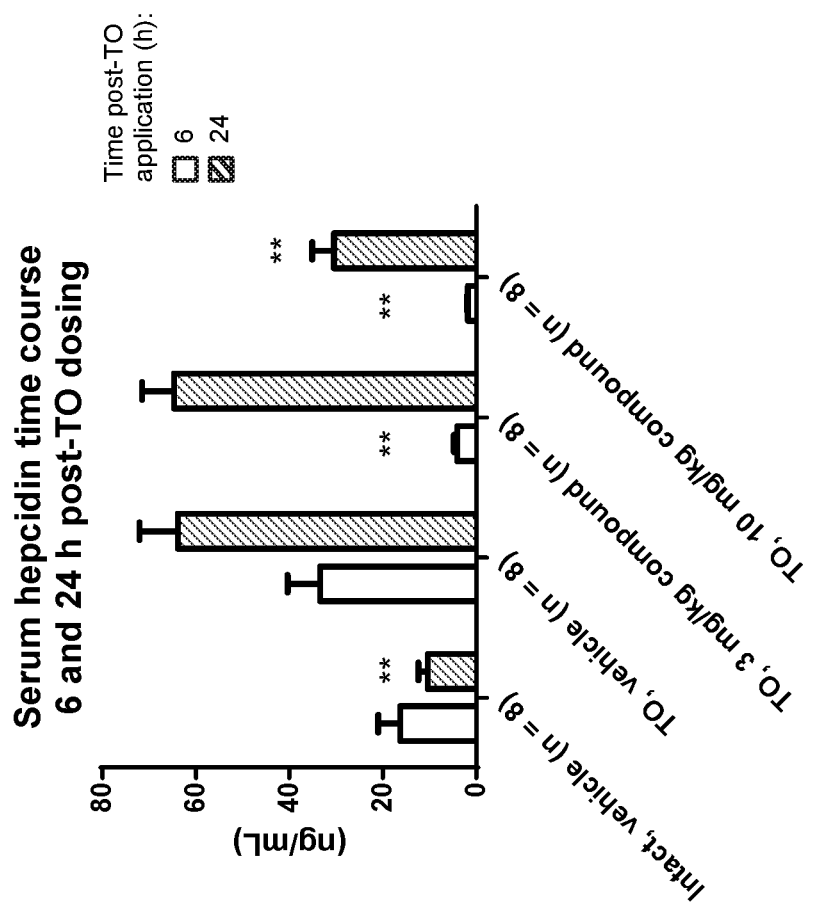
FIG. 4 shows the influence of 5-(1'-isopropyl-6'-oxo-1',6'-dihydro-[3,3'-bipyridin]-5-yl)-1-methylindolin-2-one on serum hepcidin concentration in rats.

6 hours post-TO application sublingual blood samples were taken and serum was prepared from whole blood using clot activator centrifugation tubes (Sarstedt). Serum hepcidin levels were strongly suppressed in compound A-treated rats at this time point. 24 h post-TO application rats were sacrificed by $CO_2$ overdosing and blood was isolated by venipuncture for serum preparation as described above. LC-MRM measurements of hepcidin demonstrated that in rats treated with 3 mg/kg compound A serum hepcidin concentration had returned to levels of vehicle-treated TO-challenged rats but still remained significantly reduced in rats treated with 10 mg/kg compound A (**$p<0.001$; FIG. 4; results are expressed as mean+SEM), compound A is referred to as "compound". Statistical analyses were performed using GraphPad Prism software (GraphPad Software, Inc., La Jolla, Calif.) by two-way repeated measurement analysis of variance followed by Dunnett's multiple comparisons post-hoc test comparing treatment groups to the vehicle control group.

These results suggest that compound of the invention is useful in the treatment of anaemia of chronic diseases.

Figure 5:
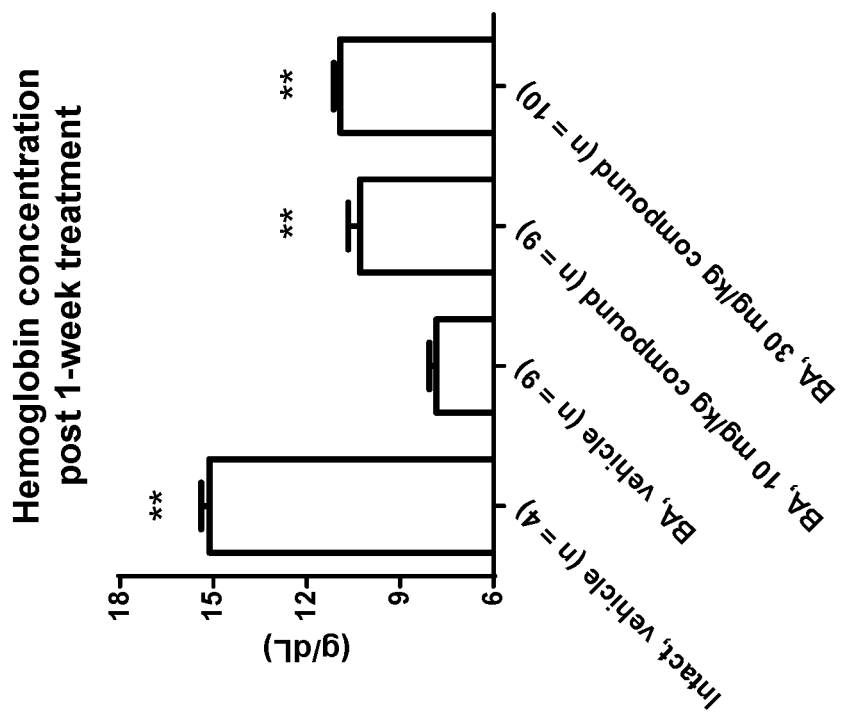
FIGS. 5 and 6 show the influence of 5-(1'-isopropyl-6'-oxo-1',6'-dihydro-[3,3'-bipyridin]-5-yl)-1-methylindolin-2-one on inflammation-induced anemia in mice.
Figure 6:
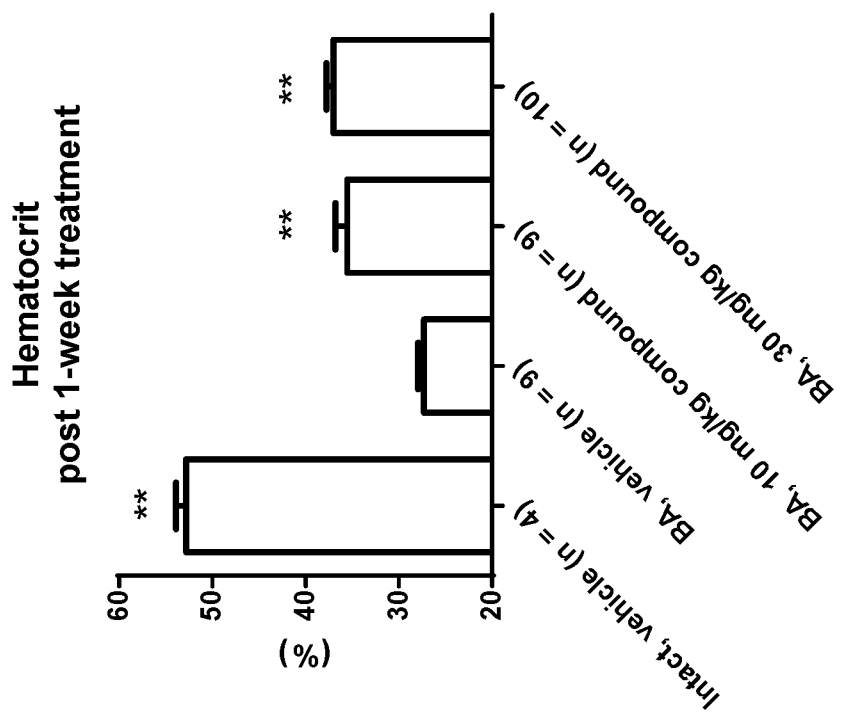

Example 57: Compound a (Compound of Example 1) Ameliorates Inflammation-Induced Anemia in Mice To assess whether compound A ameliorates anemia associated with chronic inflammation, we tested its therapeutic efficacy in a mouse model of anemia of inflammation/anemia of chronic disease (Sasu et al., Blood 115:3616-3624, 2010) induced by intraperitoneal (ip.) injection of heat-killed *Brucella abortus* (BA) particles dissolved in PBS into 10-week-old C57BL/6J male mice (body weight range: 23-30 g). Mice were housed in groups of up to five animals per cage at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. 6 days following a single ip. application of 1.2×10e9 BA particles/mL dosed at 10 mL/kg BA-injected mice were clearly anemic and showed significant reductions in hemoglobin concentration as determined in whole blood collected from the tail vein in EDTA-coated tubes and measured with an automatic hematology analyzer (VetABC, medical solution gmbh) compared to intact control C57BL/6J male mice treated with a single ip. injection of PBS (10 mL/kg). At this stage BA-injected mice were randomized into vehicle control and treatment groups according to equal decreases in hemoglobin and body weight as first and second rank parameters, respectively. BA-treated mice were then subjected to 1-week oral therapeutic treatment with compound A (10 or 30 mg/kg, b.i.d.) or vehicle (sodium carboxymethyl cellulose:water:Tween 80, 0.5:99:0.5). Animals were sacrificed by $CO_2$ overdosing and whole blood was collected in EDTA-coated tubes and measured with an automatic hematology analyzer as described before. Compound A treatment significantly improved blood hemoglobin and hematocrit values compared to vehicle-treated anemic animals (**$p<0.0001$; FIGS. 5 and 6; results are expressed as mean+SEM), compound A is referred to as "compound". Statistical analyses were performed using GraphPad Prism software (GraphPad Software, Inc., La Jolla, Calif.) by one-way analysis of variance followed by Dunnett's multiple comparisons post-hoc test comparing treatment groups to the vehicle control group.

These results suggest that compound of the invention may be useful in the treatment of anaemia of chronic diseases.

Figure 7:
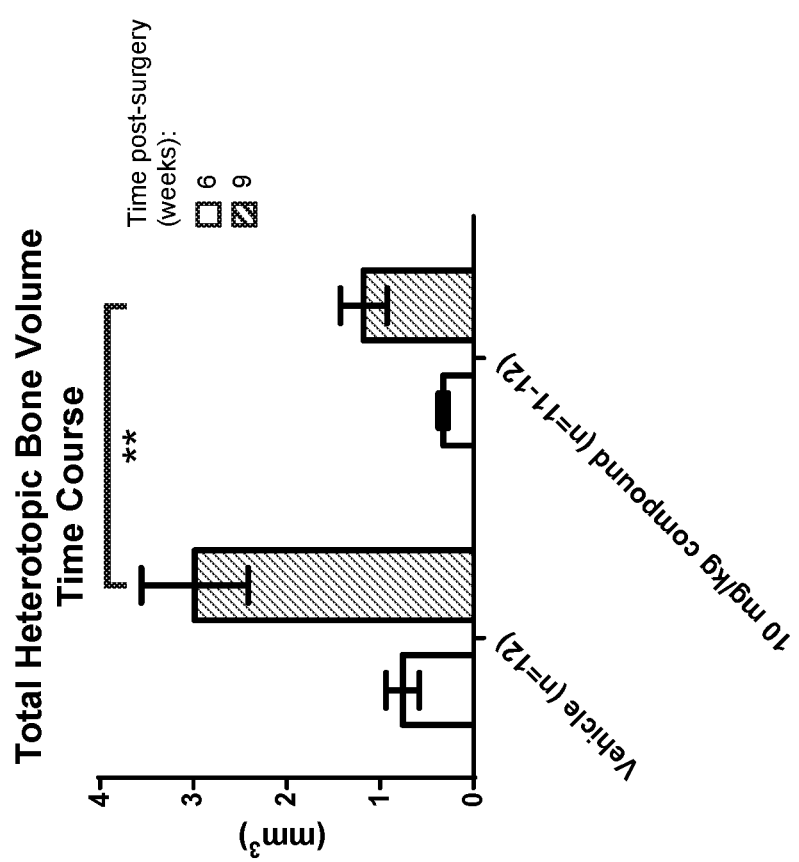
FIG. 7 shows the influence of 5-(1'-isopropyl-6'-oxo-1',6'-dihydro-[3,3'-bipyridin]-5-yl)-1-methylindolin-2-one on heterotopic bone volume in rats.

Example 58: Compound a (Compound of Example 1) Prevents Achilles Midpoint Tenotomy-Induced Heterotopic Ossification in Rats To test whether compound A was able to prevent trauma-induced heterotopic ossification (HO) of soft tissue, we tested its therapeutic efficacy in a rat model of unilateral Achilles midpoint tenotomy (Rooney et al., Matrix 12: 274-281, 1992). To this end, the left Achilles tendon of 8-week-old female Wistar rats (body weight between 190-265 g) was completely transected using a sterile scalpel (blade number 11) under isoflurane inhalation narcosis with concomitant analgesic treatment applying 0.03 mg/kg buprenorphine for 48 hours every 10-12 h subcutaneously. Preventive oral treatment with compound A (10 mg/kg q.d.) or vehicle (sodium carboxymethyl cellulose:water:Tween 80, 0.5:99:0.5) was given for 10 weeks starting on the day of surgery (n=11-12 rats per group). Rats were housed individual for 3-4 days following surgery and thereafter housed in groups of two animals per cage at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. Treatment efficacy was assessed longitudinally by taking radiographs of the operated distal leg (Faxitron LX-60 system) at 4 and 10 weeks post-tenotomy. Heterotopic bone volume was quantified in vivo by micro-computed tomography (micro-CT) under isoflurane inhalation narcosis (vivaCT40 instrument, Scanco Medical AG; 17.5 µm resolution) at 6 and 9 weeks post-surgery. 4 weeks post-tenotomy 67% of compound A-treated animals showed radiographic evidence of beginning HO compared to 100% of vehicle-treated operated rats indicating that compound A is able to significantly attenuate the HO process. Quantification of the total heterotopic bone volume at 6 and 9 weeks post-surgery confirmed a significant reduction of HO in compound A-versus vehicle-treated rats (**p<0.001; FIG. 7; results are expressed as mean+SEM), compound A is referred to as "compound"). Statistical analyses were performed using GraphPad Prism software (GraphPad Software, Inc., La Jolla, Calif.) by two-way analysis of variance followed by Bonferroni's multiple comparisons post-hoc test. These results suggest that compound of the invention is useful in the treatment of heterotopic ossification.

Figure 8:
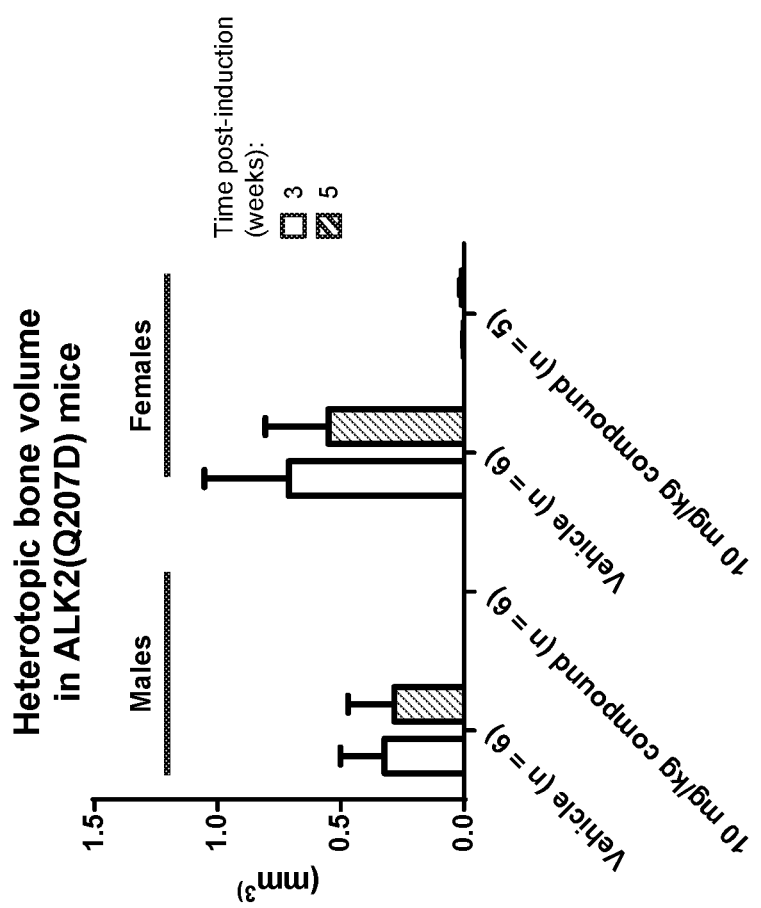
FIG. 8 shows the influence of 5-(1'-isopropyl-6'-oxo-1',6'-dihydro-[3,3'-bipyridin]-5-yl)-1-methylindolin-2-one (referred to as "compound") on heterotopic bone volume in ALK-2 transgenic mice.

Example 59 Compound a (Compound of Example 1) Prevents ALK2-Dependent Heterotopic Ossification in Mice Heterotopic ossification (HO) also occurs in certain genetic disorders such as fibrodysplasia ossificans progressiva (FOP), which is caused by gain-of-function mutations in the ALK2 gene. To determine whether compound A was able to prevent ALK2-dependent HO of soft tissue, we tested its therapeutic efficacy in a conditional ALK2(Q207D) transgenic overexpression mouse model (Fukuda et al., Genesis 44, 159-167, 2006). ALK2(Q207D) overexpression was induced locally in the left gastrocnemius muscle of 5-week-old male and female ALK2(Q207D) mice (mean body weight males: 19.5 g, females: 16.5 g) under isoflurane inhalation narcosis by intramuscular injection of adenovirus-Cre (Ad-Cre, 5×10$^8$ plaque-forming units) and 10 µM cardiotoxin to induce local skeletal muscle damage at the same time as transgene induction. Preventive oral treatment with compound A (10 mg/kg b.i.d.) or vehicle (sodium carboxymethyl cellulose:water:Tween 80, 0.5:99:0.5) was given for 5 weeks starting two days before transgene induction (n=5-6 mice per group). Mice were housed at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. Treatment efficacy was assessed longitudinally by taking radiographs of the left leg (Faxitron LX-60 system) at 3 and 5 weeks post-induction. Heterotopic bone volume was quantified in vivo by micro-computed tomography (micro-CT) under isoflurane inhalation narcosis (vivaCT40 instrument, Scanco Medical AG; 14 m resolution). At 3 and 5 weeks post-induction none of compound A-treated male mice and only one out of five female mice showed radiographic evidence of HO compared to 83% of vehicle-treated males and 67% of vehicle-treated female ALK2(Q207D) mice indicating that compound A is able to prevent ALK2-dependent HO. Quantification of the total heterotopic bone volume at the same time points confirmed that heterotopic bone was absent in compound A-treated males and four of five females, but was present in vehicle-treated ALK2(Q207D) mice of either gender (FIG. 8; results are expressed as mean+SEM). These results suggest that compound of the invention may be useful in the treatment of FOP.

Example 60: Compound a (Compound of Example 1) Induces Bone Gain in Aged Rats

To assess the bone anabolic potential of compound A, its therapeutic efficacy in aged female rats as a model of age-related human osteoporosis and other low bone mass conditions was tested. To this end, 18-month-old Wistar female rats (n=8-9 rats per group; body weight range: 330-460 g) were subjected to two-month once daily oral treatment with compound A (5 mg/kg q.d.) or vehicle (sodium carboxymethyl cellulose:water:Tween 80, 0.5:99:0.5). Rats were housed at 25° C. with a 12:12 h light-dark cycle and were fed a standard rodent diet containing 18.2% protein and 3.0% fat with an energy content of 15.8 MJ/kg (3890, Provimi Kliba SA) with food and water provided ad libitum. Treatment efficacy was determined by in vivo peripheral quantitative computed tomography (pQCT) and micro-computed tomography (micro-CT) in the left proximal tibia metaphysis under isoflurane inhalation narcosis (Stratec-Norland XCT-2000 pQCT; voxel size: 0.1 mm×0.1 mm×0.5 mm; vivaCT40 instrument, Scanco Medical AG; 12.5 µm resolution) after 8 weeks of treatment. Compound A-treated animals showed increases in total bone mineral content (BMC) and density (BMD), which was related to bone gain in both bone compartments as reflected by elevated cortical bone thickness and cancellous BMD. The latter was related to enhanced trabecular thickness, but not number. Thus, compound A is bone anabolic in the aged skeleton. Mean percent changes versus baseline in tibial bone structure indices are summarized in the table below.

| %-change versus baseline[1] | Vehicle (n = 8) | 5 mg/kg compound A (n = 9) |
|---|---|---|
| Total BMC[2] | −1.1 ± 0.8 | 4.3 ± 1.7* |
| Total BMD | −3.0 ± 0.9 | 5.6 ± 0.6*** |
| Cancellous BMD | −4.9 ± 1.1 | 5. 9 ± 2.0*** |
| Cancellous BV/TV[2] | −6.5 ± 1.7 | 8.9 ± 3.0*** |
| Cortical thickness | 0.1 ± 1.2 | 12.0 ± 2.2*** |
| Trabecular thickness | 0.6 ± 1.2 | 11.1 ± 2.9** |
| Trabecular number | −9.1 ± 3.5 | −0.6 ± 5.4 |

[1]Data represent means ± SEM. [2]Total BMC as measured by pQCT. All other parameters were determined by micro-CT. [3]BV/TV: bone per tissue volume. Statistical analyses were performed using GraphPad Prism software (GraphPad Software, Inc., La Jolla, CA) by unpaired Student's t-test. Statistical significance is designated as follows: *, $p < 0.05$; , $p < 0.01$; *, $p < 0.001$ versus vehicle-treated rats.

These results suggest that compound of the invention may be useful in the treatment of human osteoporosis.

The invention claimed is:

1. A compound of formula (I), or a pharmaceutically acceptable salt thereof,

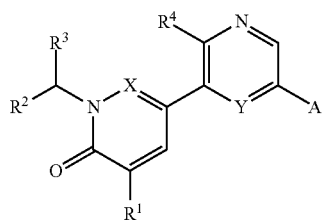

(I)

wherein
A represents

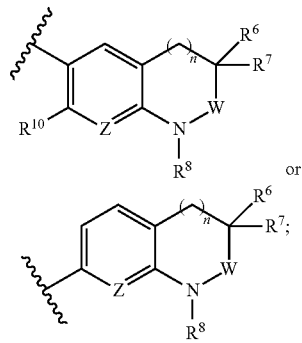

or $R^1$ represents hydrogen, $C_{1-4}$alkyl or $C_{1-4}$alkoxy;
$R^2$ and $R^3$ independently represent hydrogen, $C_{1-6}$alkyl, $C_{1-6}$haloalkyl, $C_{1-6}$alkoxy or $C_{3-6}$cycloalkyl or $R^2$ and $R^3$ together with the carbon atom to which they are attached form a 3- to 6-membered ring which may contain one heteroatom;
X is N or —CH;
$R^4$ represents hydrogen or amino;
Y is N or —$CR^5$;
$R^5$ is hydrogen or fluorine;
Z is N or —$CR^9$;
n is 0, 1 or 2;
W is —C(=O)— or —S(O)$_2$—;
$R^6$ and $R^7$ independently represent hydrogen, fluorine or $C_{1-4}$alkyl;
$R^8$ represents hydrogen, $C_{1-6}$alkyl, $C_{3-6}$cycloalkyl$C_{1-6}$alkyl, $C_{1-4}$alkoxy$C_{1-6}$alkyl or hydroxy$C_{1-6}$alkyl;
$R^9$ represents hydrogen, halogen or $C_{1-4}$alkyl; and
$R^{10}$ represents hydrogen or halogen.

2. A compound of formula (Ia) or a pharmaceutically acceptable salt thereof,

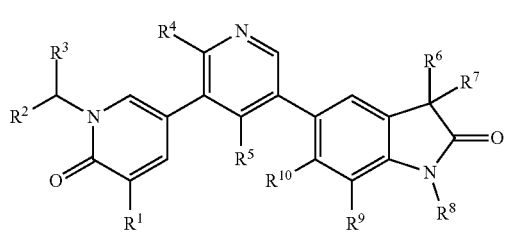

(Ia)

wherein
$R^1$ represents hydrogen, $C_{1-4}$alkyl or $C_{1-4}$alkoxy;
$R^2$ and $R^3$ independently represent hydrogen, $C_{1-6}$alkyl, $C_{1-6}$haloalkyl, $C_{1-6}$alkoxy or $C_{3-6}$cycloalkyl or $R^2$ and $R^3$ together with the carbon atom to which they are attached form a 3- to 6-membered ring which may contain one heteroatom;
$R^4$ represents hydrogen or amino;
$R^5$ is hydrogen or fluorine;
$R^6$ and $R^7$ independently represent hydrogen, fluorine or $C_{1-4}$alkyl;
$R^8$ represents hydrogen, $C_{1-6}$alkyl, $C_{3-6}$cycloalkyl$C_{1-6}$alkyl, $C_{1-4}$alkoxy$C_{1-6}$alkyl or hydroxy$C_{1-6}$alkyl;
$R^9$ represents hydrogen, halogen or $C_{1-4}$alkyl; and
$R^{10}$ represents hydrogen or halogen.

3. A compound of formula (Ib) or a pharmaceutically acceptable salt thereof,

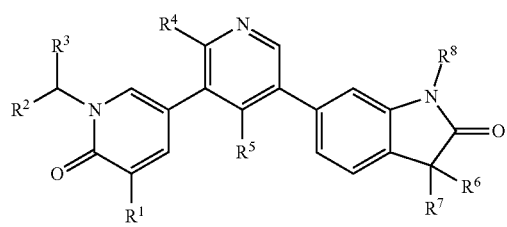

(Ib)

wherein
$R^1$ represents hydrogen, $C_{1-4}$alkyl or $C_{1-4}$alkoxy;
$R^2$ and $R^3$ independently represent hydrogen, $C_{1-6}$alkyl, $C_{1-6}$haloalkyl, $C_{1-6}$alkoxy or $C_{3-6}$cycloalkyl or $R^2$ and $R^3$ together with the carbon atom to which they are attached form a 3- to 6-membered ring which may contain one heteroatom;
$R^4$ represents hydrogen or amino;
$R^5$ is hydrogen or fluorine;
$R^6$ and $R^7$ independently represent hydrogen, fluorine or $C_{1-4}$alkyl;
$R^8$ represents hydrogen, $C_{1-6}$alkyl, $C_{3-6}$cycloalkyl$C_{1-6}$alkyl, $C_{1-4}$alkoxy$C_{1-6}$alkyl or hydroxy$C_{1-6}$alkyl.

4. The compound according to claim 1 or a pharmaceutically acceptable salt thereof, wherein
$R^1$ is hydrogen.

5. The compound according to claim 1 or a pharmaceutically acceptable salt thereof wherein
$R^2$ and $R^3$ independently represent hydrogen or $C_{1-6}$alkyl.

6. The compound according to claim 1 or a pharmaceutically acceptable salt thereof wherein
$R^2$ and $R^3$ are both methyl.

7. The compound according to claim 1 or a pharmaceutically acceptable salt thereof wherein
$R^4$ is hydrogen.

8. The compound according to claim 1 or a pharmaceutically acceptable salt thereof wherein
X is —CH.

9. The compound according to claim 1 or a pharmaceutically acceptable salt thereof wherein
$R^6$ and $R^7$ independently represent hydrogen or fluorine.

10. The compound according to claim 1 or a pharmaceutically acceptable salt thereof wherein
$R^8$ is hydrogen or $C_{1-6}$alkyl.

11. The compound according to claim 1 or a pharmaceutically acceptable salt thereof wherein
Y is —CH.

12. The compound according to claim 1 or a pharmaceutically acceptable salt thereof wherein
W is —C(=O)—.

13. The compound of the formula (I) according to claim 1, or a pharmaceutically acceptable salt thereof, wherein
A represents

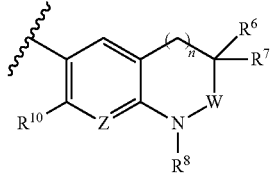

$R^1$ represents hydrogen;
$R^2$ and $R^3$ represent $C_{1-6}$alkyl;
X is —CH;
$R^4$ represents hydrogen;
Y is —$CR^5$;
$R^5$ is hydrogen;
Z is —$CR^9$;
n is 0;
W is —C(=O)—;
$R^6$ and $R^7$ represent hydrogen;
$R^8$ represents $C_{1-6}$alkyl, $C_{3-6}$cycloalkyl$C_{1-6}$alkyl or $C_{1-4}$alkoxy$C_{1-6}$alkyl;
$R^9$ represents hydrogen; and
$R^{10}$ represents hydrogen.

14. The compound according to claim 1 or a pharmaceutically acceptable salt thereof which is selected from the group consisting of
5-(5-(1-isopropyl-6-oxo-1,6-dihydropyridin-3-yl)pyridin-3-yl)-1-methylindolin-2-one;
5-(1'-Isopropyl-5'-methoxy-6'-oxo-1',6'-dihydro-[3,3'-bipyridin]-5-yl)-1-methylindolin-2-one;
5-(5-(1-Isopropyl-5-methyl-6-oxo-1,6-dihydropyridin-3-yl)pyridin-3-yl)-1-methylindolin-2-one;
1-methyl-5-(6'-oxo-1'-(pentan-3-yl)-1',6'-dihydro-[3,3'-bipyridin]-5-yl)indolin-2-one;
5-(5'-Ethyl-1'-isopropyl-6'-oxo-1',6'-dihydro-[3,3'-bipyridin]-5-yl)-1-methylindolin-2-one;
5-(1'-Cyclobutyl-6'-oxo-1',6'-dihydro-[3,3'-bipyridin]-5-yl)-1-methylindolin-2-one;
5-(1'-(sec-butyl)-6'-oxo-1',6'-dihydro-[3,3'-bipyridin]-5-yl)-1-methylindolin-2-one;
5-(1'-cyclopentyl-6'-oxo-1',6'-dihydro-[3,3'-bipyridin]-5-yl)-1-methylindolin-2-one;
5-(1'-ethyl-6'-oxo-1',6'-dihydro-[3,3'-bipyridin]-5-yl)-1-methylindolin-2-one;
5-(1'-cyclopropyl-6'-oxo-1',6'-dihydro-[3,3'-bipyridin]-5-yl)-1-methylindolin-2-one;
5-(1'-(cyclobutylmethyl)-6'-oxo-1',6'-dihydro-[3,3'-bipyridin]-5-yl)-1-methylindolin-2-one;
1-methyl-5-(6'-oxo-1'-(2,2,2-trifluoroethyl)-1',6'-dihydro-[3,3'-bipyridin]-5-yl)indolin-2-one;
5-(1'-(2-ethylbutyl)-6'-oxo-1',6'-dihydro-[3,3'-bipyridin]-5-yl)-1-methylindolin-2-one;
5-(1'-isobutyl-6'-oxo-1',6'-dihydro-[3,3'-bipyridin]-5-yl)-1-methylindolin-2-one;
5-(1'-(methoxymethyl)-6'-oxo-1',6'-dihydro-[3,3'-bipyridin]-5-yl)-1-methylindolin-2-one;
1-methyl-5-(6'-oxo-1'-(3,3,3-trifluoropropyl)-1',6'-dihydro-[3,3'-bipyridin]-5-yl)indolin-2-one;
5-(1'-isopentyl-6'-oxo-1',6'-dihydro-[3,3'-bipyridin]-5-yl)-1-methylindolin-2-one;
1-methyl-5-(6'-oxo-1'-(tetrahydro-2H-pyran-2-yl)-1',6'-dihydro-[3,3'-bipyridin]-5-yl)indolin-2-one;
1-methyl-5-(1'-methyl-6'-oxo-1',6'-dihydro-[3,3'-bipyridin]-5-yl)indolin-2-one;
1-ethyl-5-(1'-isopropyl-6'-oxo-1,6'-dihydro-[3,3'-bipyridin]-5-yl)indolin-2-one;
1-Isopropyl-5-(1'-isopropyl-6'-oxo-1',6'-dihydro-[3,3'-bipyridin]-5-yl)indolin-2-one;
3-Ethyl-5-(1'-isopropyl-6'-oxo-1',6'-dihydro-[3,3'-bipyridin]-5-yl)-1-methylindolin-2-one;
3,3-Difluoro-5-(1'-isopropyl-6'-oxo-1',6'-dihydro-[3,3'-bipyridin]-5-yl)-1-methylindolin-2-one;
1-Isobutyl-5-(1'-isopropyl-6'-oxo-1',6'-dihydro-[3,3'-bipyridin]-5-yl)indolin-2-one;
5-(1'-Isopropyl-6'-oxo-1',6'-dihydro-[3,3'-bipyridin]-5-yl)-1-propylindolin-2-one;
6-(1'-Isopropyl-6'-oxo-1',6'-dihydro-[3,3'-bipyridin]-5-yl)-1-methylindolin-2-one;
5-(1'-Isopropyl-6'-oxo-1',6'-dihydro-[3,3'-bipyridin]-5-yl)-1-(2-methoxyethyl)-1H-pyrrolo[2,3-b]pyridin-2(3H)-one;
6-(1'-Isopropyl-6'-oxo-1',6'-dihydro-[3,3'-bipyridin]-5-yl)-1-methyl-3,4-dihydroquinolin-2(1H)-one;
5-(1'-Isopropyl-6'-oxo-1',6'-dihydro-[3,3'-bipyridin]-5-yl)-1-(2-methoxyethyl)indolin-2-one;
5-(1'-Isopropyl-6'-oxo-1',6'-dihydro-[3,3'-bipyridin]-5-yl)-1-(3-methoxypropyl)indolin-2-one;
5-(1'-Isopropyl-6'-oxo-1',6'-dihydro-[3,3'-bipyridin]-5-yl)-1,3,3-trimethyl-1H-pyrrolo[2,3-b]pyridin-2(3H)-one;
6-(1'-isopropyl-6'-oxo-1',6'-dihydro-[3,3'-bipyridin]-5-yl)-3,3-dimethylindolin-2-one;
6-(1'-isopropyl-6'-oxo-1',6'-dihydro-[3,3'-bipyridin]-5-yl)-3-methylindolin-2-one;
5-(5-(1-Isopropyl-6-oxo-1,6-dihydropyridin-3-yl)pyridin-3-yl)indolin-2-one;
5-(1'-isopropyl-6'-oxo-1',6'-dihydro-[3,3'-bipyridin]-5-yl)-1,7-dimethylindolin-2-one;
7-Fluoro-5-(1'-isopropyl-6'-oxo-1',6'-dihydro-[3,3'-bipyridin]-5-yl)-1-methylindolin-2-one;
6-(1'-Isopropyl-6'-oxo-1',6'-dihydro-[3,3'-bipyridin]-5-yl)-1-methyl-3,4-dihydro-1,8-naphthyridin-2(1H)-one;
1-(cyclobutylmethyl)-5-(1'-isopropyl-6'-oxo-1',6'-dihydro-[3,3'-bipyridin]-5-yl)indolin-2-one;
7-(1'-isopropyl-6'-oxo-1',6'-dihydro-[3,3'-bipyridin]-5-yl)-1-methyl-4,5-dihydro-1H-benzo[b]azepin-2(3H)-one;

1-(2-ethylbutyl)-5-(1'-isopropyl-6'-oxo-1',6'-dihydro-[3,3'-bipyridin]-5-yl)indolin-2-one;
5-(1'-Isopropyl-6'-oxo-1',6'-dihydro-[3,3'-bipyridin]-5-yl)-1H-pyrrolo[2,3-b]pyridin-2(3H)-one;
5-(2-amino-1'-isopropyl-6'-oxo-1',6'-dihydro-[3,3'-bipyridin]-5-yl)-1-methylindolin-2-one;
5-(5-amino-6-(1-isopropyl-6-oxo-1,6-dihydropyridin-3-yl)pyrazin-2-yl)-1-methylindolin-2-one;
5-(5-(1-isopropyl-6-oxo-1,6-dihydropyridazin-3-yl)pyridin-3-yl)-1-methylindolin-2-one;
1-(2-hydroxyethyl)-5-(1'-isopropyl-6'-oxo-1',6'-dihydro-[3,3'-bipyridin]-5-yl)indolin-2-one;
5-(6-(1-isopropyl-6-oxo-1,6-dihydropyridin-3-yl)pyrazin-2-yl)-1-methylindolin-2-one;
1-(3-hydroxypropyl)-5-(1'-isopropyl-6'-oxo-1',6'-dihydro-[3,3'-bipyridin]-5-yl)indolin-2-one and
1-isopropyl-5'-(1-methyl-2,2-dioxido-1,3-dihydrobenzo[c]isothiazol-5-yl)-[3,3'-bipyridin]-6(1H)-one.

15. A pharmaceutical composition comprising a therapeutically effective amount of the compound according to claim 1 or a pharmaceutically acceptable salt thereof and one or more pharmaceutically acceptable carriers.

16. A combination comprising a therapeutically effective amount of the compound according to claim 1 or a pharmaceutically acceptable salt thereof and one or more therapeutically active agents.

17. A method of inhibiting ALK-2 receptor activity in a subject, wherein the method comprises administering to the subject a therapeutically effective amount of the compound according to claim 1 or a pharmaceutically acceptable salt thereof.

18. A method of treating a disorder or disease selected from anaemia of chronic disease, heterotopic ossification, and fibrodysplasia ossificans progressiva, comprising administering to the subject a therapeutically effective amount of the compound according to claim 1 or a pharmaceutically acceptable salt thereof.

* * * * *